(12) United States Patent
Scharenberg

(10) Patent No.: US 12,358,970 B2
(45) Date of Patent: *Jul. 15, 2025

(54) METHODS OF EXOGENOUS DRUG ACTIVATION OF CHEMICAL-INDUCED SIGNALING COMPLEXES EXPRESSED IN ENGINEERED CELLS IN VITRO AND IN VIVO

(71) Applicant: Seattle Children's Hospital, Seattle, WA (US)

(72) Inventor: Andrew M. Scharenberg, Seattle, WA (US)

(73) Assignee: Seattle Children's Hospital, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/446,018

(22) Filed: Aug. 8, 2023

(65) Prior Publication Data
US 2024/0117008 A1    Apr. 11, 2024

Related U.S. Application Data

(63) Continuation of application No. 16/467,013, filed as application No. PCT/US2017/065746 on Dec. 12, 2017, now Pat. No. 11,753,460.

(60) Provisional application No. 62/433,540, filed on Dec. 13, 2016.

(51) Int. Cl.
| | | |
|---|---|---|
| *C12N 15/62* | (2006.01) | |
| *C07K 14/71* | (2006.01) | |
| *C07K 14/715* | (2006.01) | |
| *C12N 15/63* | (2006.01) | |

(52) U.S. Cl.
CPC ......... *C07K 14/7155* (2013.01); *C12N 15/62* (2013.01); *C07K 2317/53* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,587,044 A | 5/1986 | Miller |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,166,315 A | 11/1992 | Summerton et al. |
| 5,173,414 A | 12/1992 | Lebkowski et al. |
| 5,175,273 A | 12/1992 | Bischofberger et al. |
| 5,177,196 A | 1/1993 | Meyer et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,235,033 A | 8/1993 | Summerton et al. |
| 5,245,022 A | 9/1993 | Weis et al. |
| 5,254,469 A | 10/1993 | Warren et al. |
| 5,258,506 A | 11/1993 | Urdea et al. |
| 5,262,536 A | 11/1993 | Hornes et al. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |

(Continued)

FOREIGN PATENT DOCUMENTS

| | | |
|---|---|---|
| WO | WO 93/07883 | 4/1993 |
| WO | WO 94/018317 | 8/1994 |

(Continued)

OTHER PUBLICATIONS

Altschul et al., 1996, [27] Local alignment statistics, Methods in Enzymology, 266:460-480.
Angart et al., 2013, Design of siNRA therapeutics from the molecular scale, Pharmaceuticals, 6(4):440-468.
Ausubel et al., ed., 1987, Current Protocols in Molecular Biology New York, NY: Wiley (TOC).
Ayuso et al., 2010, Production, purification and characterization of adeno-associated vectors, Curr. Gene Ther., 10(6):423-436.
Banaszynski et al., Apr. 2005, Characterization of the FKBP-rapamycin-FRB ternary complex, Journal of the American Chemical Society, 127(13):4715-4721.

(Continued)

*Primary Examiner* — Christine J Saoud
*Assistant Examiner* — Jon M Lockard
(74) *Attorney, Agent, or Firm* — Knobbe, Martens, Olson & Bear LLP

(57) ABSTRACT

The present application relates to compositions comprising fusion proteins and cells expressing the proteins. The application further relates to methods of using the fusion proteins, cells, and compositions for modulating cell signaling and for selective expansion of cells.

20 Claims, 36 Drawing Sheets

Specification includes a Sequence Listing.

(56) References Cited

U.S. PATENT DOCUMENTS

| | | |
|---|---|---|
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger et al. |
| 5,432,272 A | 7/1995 | Benner et al. |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr et al. |
| 5,489,677 A | 2/1996 | Sanghvi et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Cook et al. |
| 5,623,070 A | 4/1997 | Cook et al. |
| 5,625,050 A | 4/1997 | Beaton et al. |
| 5,633,360 A | 5/1997 | Bischofberger et al. |
| 5,658,776 A | 8/1997 | Flotte et al. |
| 5,663,312 A | 9/1997 | Chaturvedula et al. |
| 5,677,437 A | 10/1997 | Teng et al. |
| 5,677,439 A | 10/1997 | Weis et al. |
| 5,688,941 A | 11/1997 | Cook et al. |
| 5,714,331 A | 2/1998 | Buchardt et al. |
| 5,719,262 A | 2/1998 | Buchardt et al. |
| 5,750,692 A | 5/1998 | Cook et al. |
| 5,763,588 A | 6/1998 | Matteucci et al. |
| 5,786,211 A | 7/1998 | Johnson et al. |
| 5,830,653 A | 11/1998 | Froehler et al. |
| 5,871,982 A | 2/1999 | Wilson et al. |
| 6,005,096 A | 12/1999 | Matteucci et al. |
| 6,103,521 A | 8/2000 | Capon et al. |
| 6,165,787 A | 12/2000 | Crabtree et al. |
| 6,258,595 B1 | 7/2001 | Gao et al. |
| 6,287,860 B1 | 9/2001 | Monia et al. |
| 11,753,460 B2 | 12/2023 | Scharenberg |
| 2003/0158403 A1 | 8/2003 | Manoharan |
| 2003/0206891 A1 | 11/2003 | Clackson et al. |
| 2010/0034777 A1 | 2/2010 | Wandless et al. |
| 2014/0068797 A1 | 3/2014 | Doudna |
| 2015/0038684 A1 | 2/2015 | Jensen |
| 2015/0266973 A1 | 9/2015 | Jarjour et al. |
| 2016/0311901 A1 | 10/2016 | Jarjour |
| 2017/0166877 A1 | 6/2017 | Bayle et al. |
| 2017/0175128 A1 | 6/2017 | McPherson |
| 2018/0037630 A1 | 2/2018 | Tanaka et al. |
| 2018/0244797 A1 | 8/2018 | Pule et al. |
| 2021/0340573 A1 | 11/2021 | Scharenberg et al. |

FOREIGN PATENT DOCUMENTS

| | | |
|---|---|---|
| WO | WO 95/13365 | 5/1995 |
| WO | WO 95/13392 | 5/1995 |
| WO | WO 96/17947 | 6/1996 |
| WO | WO 96/24671 | 8/1996 |
| WO | WO 96/41865 | 12/1996 |
| WO | WO 97/06243 | 2/1997 |
| WO | WO 97/08298 | 3/1997 |
| WO | WO 97/09441 | 3/1997 |
| WO | WO 97/21825 | 6/1997 |
| WO | WO 98/02558 | 1/1998 |
| WO | WO 99/11764 | 3/1999 |
| WO | WO 99/36553 | 7/1999 |
| WO | WO 08/006588 | 1/2008 |
| WO | WO 08/097875 | 8/2008 |
| WO | WO 13/123061 | 8/2013 |
| WO | WO 13/176772 | 11/2013 |
| WO | WO 14/127261 | 8/2014 |
| WO | WO 15/017214 | 2/2015 |
| WO | WO 15/090229 | 6/2015 |
| WO | WO 16/098078 | 6/2016 |
| WO | WO 16/127257 | 8/2016 |
| WO | WO 16/135470 | 9/2016 |
| WO | WO 16/201047 | 12/2016 |
| WO | WO 17/029512 | 2/2017 |
| WO | WO 17/068360 | 4/2017 |
| WO | WO 18/111834 | 6/2018 |
| WO | WO 18/161038 | 9/2018 |
| WO | WO 19/210281 | 10/2019 |
| WO | WO 20/097582 | 5/2020 |

OTHER PUBLICATIONS

Banaszynski et al., Sep. 8, 2006, A rapid, reversible, and tunable method to regulate protein function in living cells using synthetic small molecules, Cell, 126(5):995-1004.

Bayle et al., 2006, Rapamycin analogs with differential binding specificity permit orthogonal control of protein activity, Chem. Biol., 13(1):99-107.

Behlke, 2008, Chemical modification of siRNAs for in vivo use, Oligonucleotides, 18(4):305-319.

Braasch et al., Apr. 9, 2002, Novel antisense and peptide nucleic acid strategies for controlling gene expression, Biochemistry, 41(14):4503-4510.

Bramsen et al., Aug. 2012, Development of therapeutic-grade small interfering RNAs by chemical engineering, Front. Genet., 3(154):1-22.

Burnett et al., Sep. 2011, Current progress of siRNA/shRNA therapeutics in clinical trials, Biotechnol. J., 6(9):1130-1146.

(56) References Cited

OTHER PUBLICATIONS

Chen et al., May 1995, Identification of an 11-kDa FKBP12-rapamycin-binding domain within the 289-kDa FKBP12-rapamycin-associated protein and characterization of a critical serine residue, Proc. Natl. Acad. Sci. U.S.A., 92(11):4947-4951.
Chernolovskaya et al., 2010, Chemical modification of siRNA, Curr. Opin. Mol Ther., 12(2):158-167.
Choi et al., "Structure of the FKBP12-rapamycin complex interacting with the binding domain of human FRAP" Science. 1996. 273(5272):239-242.
Choi et al., 1996, Structure of the FKBP12-rapamycin complex interacting with the binding domain of the human FRAP, Science, 273(5272):239-242.
DeRose et al., Mar. 2013, Manipulating signaling at will: chemically-inducible dimerization (CID) techniques resolve problems in cell biology, Pflugers Arch. 465(3):409-417.
Fonfara et al., 2014, Phylogeny of Cas9 determines functional exchangeability of dual-RNA and Cas9 among orthologous type II CRISPR-Cas systems, Nucl. Acids Res., 42(4):2577-2590.
Fucini et al., 2012, Adenosine modification may be preferred for reducing siRNA immune stimulation, Nucleic Acid Ther., 22(3):205-210.
Gaglione et al., 2010, Recent progress in chemically modified siRNAs, Mini Rev. Med. Chem., 10(7):578-595.
Gebeyehu et al., 1987, Novel biotinylated nucleotide—analogs for labeling and colorimetric detection of DNA, Nucl Acids Res., 15(11):4513-4534.
Genesis, 2001, 30(3), TOC.
Graef et al., 1997, Proximity and orientation underlie signaling by the non-receptor tyrosine kinase ZAP70, EMBO J. 16(18):5618-5628.
Grupp et al., 2013, Chimeric antigen receptor-modified T cells for acute lymphoid leukemia. N Engl J Med 368:1509-1518.
Heasman, 2002, Morpholine oligos: making sense of antisense? Dev. Biol., 243(2):209-214.
Hermonat et al., Oct. 1984, Use of adeno-associated virus as a mammalian DNA cloning vector: transduction of neomycin resistance into mammalian tissue culture cells, Proc. Natl. Acad. Sci. U.S.A., 81(2):6466-6470.
Jinek et al., Aug. 17, 2012, A programmable dual-RNA-guided DNA endonuclease in adaptive bacterial immunity, Science, 337(6096):816-821.
Judge et al., 2006, Design of noninflammatory synthetic siRNA medicating potent gene silencing in vivo, Mol. Ther., 13:494-505.
Judge et al., Feb. 2008, Hum. Gene Ther., Overcoming the innate immune response to small interfering RNA, 19(2):111-124.
Kabanov et al., Jan. 1990, A new class of antivirals; antisense oligonucleotides combined with a hydrophobic substituent effectively inhibit influenza virus reproduction and synthesis of virus-specific proteins in MDCK cells, FEBS Lett., 259(2):327-330.
Kalos et al., 2011, T cells with chimeric antigen receptors have potent antitumor effects and can establish memory in patients with advanced leukemia, Sci. Transl. Med. 3(95):95ra73.
Kanamori et al., Nov. 2016, Induced regulatory T cells; their development, stability, and applications, Trends in Immunology, 37(11):803-811.
Kanasty et al., 2012, Action and reaction: the biological response to siRNA And its delivery vehicles, Mol. Ther., 20(3):513-524.
Kapp et al., 2009, Post-Targeting Functions of Signal Peptides. In: Madame Curie BioScience Database. Landes Bioscience, Austin, TX, 22 pp.
Kariko et al., Aug. 2005, Suppression of RNA recognition by toll-like receptors; the impact of nucleoside modification and the evolutionary origin of NRA, Immunity, 23(2):165-175.
Kim, et al., May 11, 2007, NMR Structural Studies of Interaction of a Small, Nonpeptidyl Tpo Mimic with the Thrombopoietin Receptor Extracellular Juxtamembrane and Transmembrane Domains, J Biol Chem, 282(19):14253-14261.
Kole et al., 2012, RNA therapeutics; beyond RNA interference and antisense oligonucleotides, Nat. Rev. Drug Disc., 11(2):125-140.

Kormann et al., 2011, Expression of therapeutic proteins after delivery of chemically modified mRNA in mice, Nat. Biotechnol., 29:154-157.
Lacerra et al., Aug. 15, 2000, Restoration of hemoglobin A synthesis in erythroid cells from peripheral blood of thalassemic patients, Proc. Natl. Acad. Sci. U.S.A., 97(17):9591-9596.
Lebkowski, et al., Oct. 1988, Adeno-associated virus: a vector system for efficient introduction and integration of DNA into a variety of mammalian cell types, Mol. Cell. Biol., 8(10):3988-3996.
Letsinger et al., Sep. 1989, Cholesteryl-conjugated oligonucleotides: synthesis, properties, and activity as inhibitors of replication of human immunodeficiency virus in cell culture, Proc. Natl. Acad. Sci. U.S.A., 86(17):6553-6556.
Li et al., 2002, A novel conditional Akt 'survival switch' reversibly protects cells from apoptosis, Gene Therapy. 9(4):233-244.
Liang et al., "1NSG. The Structure of the Immunophilin-Immunosuppressant FKBP12-Rapamycin Complex Interacting With Human FRAP", PDB DOI: 10.2210/pdb1NSG/pdb, Mar. 18, 1998.
Liang et al., 1999, Refined structure of the FKBP12-rapamycin-FRB ternary complex at 2.2 A resolution, Acta Crystallogr D Biol Crystallogr. 55(4):736-744.
Love et al., 2010, Lipid-like materials for low-dose, in vivo gene silencing, Proc. Nat. Acad. Sci. U.S.A., 107(5):1864-1869.
Ma et al., 2014, Pol III promoters to express small RNAs: delineation of transcription initiation, Mol. Ther.—Nucleic Acids 3:e161, doi:10.1038/mtna.2014.12.
McLaughlin et al., Jun. 1988, Adeno-associated virus general transduction vectors: analysis of proviral structures, J. Virol., 62(6):1963-1973.
Mietzsch et al., 2014, OneBac: platform for scalable and high-titer production of adeno-associated virus serotype 1-12 vectors for gene therapy, Hum. Gene Ther., 25(3):212-222.
Mietzsch et al., 2015, OncBac 2.0: Sf9 cell lines for production f AAV5 vectors with enhanced infectivity and minimal encapsidation of foreign DNA, Hum. Gene Ther., 26(10):688-697.
Mietzsch et al., 2017, OneBac 2.0: Sf9 cell lines for production of AAV1, AAV2, and AAV8 vectors with minimal encapsidation of foreign DNA, Hum. Gene Ther. Method, 28(1):15-22.
Nasevicius et al., Oct. 2000, Effective targeted gene 'knockdown' in zebrafish, Nat. Genet., 26(2):216-220.
Nielsen et al., 1991, Sequence-selective recognition of DNA by strand displacement with a thymine- substitute polyamide, Science, 254(5037):1497-1500.
Oberhauser et al., 1992, Effective incorporation of 2'-O-methyl-oligoribonucelotides into liposomes and enhanced cell association through modification with thiocholesterol, Nucl. Acids Res., 20(3):533-538.
Ogawa et al., Aug. 29, 2013, Construction of unnatural heterodimeric receptor based on IL-2 and IL-t receptor subunits, Biotechnol Prog. 29(6):1512-1518, 2013.
Peer et al., 2011, Special delivery: targeted therapy with small RNAs, Gene Ther., 18:1127-1133.
Restifo et al., 2012, Adoptive immunotherapy for cancer: harnessing the T cell response, Nat. Rev. Immunol. 12(4):269-281.
Ruiz-Medina et al., Interleukin-2 Receptor B Thr-450 Phosphorylation Is a Positive Regulator for Receptor Complex Stability and Activation of Signaling Molecules, J Biol Chem. 2015. 290(34):20972-20983.
Sambrook et al., 2012, Molecular Cloning: A Laboratory Manual (4th ed.), Cold Spring Harbor, NY: Cold Spring Harbor Laboratory (TOC).
Samulski et al., 1982, Cloning of adeno-associated virus into pBR322: rescue of intact virus from the recombinant plasmid in human cells, Proc. Natl. Acad. Sci. U.S.A., 79(6):2077-2081.
Samulski et al., 1989, Helper-free stocks of recombinant adeno-associated viruses: normal integration does not require viral gene expression, J. Virol., 63(9):3822-3828.
Sander et al., Apr. 2014, CRPSPR-Cas systems for genome editing, regulation and targeting, Nat. Biotechnol., 32(4):347-355.
Sapranauskas et al., 2011, The streptococcus thermo[hilus CRISPR/Cas system provides immunity in *Escherichia coli*, Nucl. Acids Res., 39(21):9275-9282.

(56) References Cited

OTHER PUBLICATIONS

Schlessinger et al., Sep. 20, 2002, Ligand-induced, receptor-mediated dimerization and activation of EGF receptor, Cell, 110(6):669-672.
Senapathy et al., Apr. 10, 1984, Molecular cloning of adeno-associate virus variant genomes and generation of infectious virus by recombination in mammalian cells, J. Biol. Chem., 259(7):4661-4666.
Shea et al., 1990, Synthesis, hybridization properties and antiviral activity of lipid-oligodeoxynucleotide conjugates, Nucl. Acids Res., 18(13):3777-3783.
Sogo et al., 2008, Selective expansion of genetically modified T cells using an antibody/interleukin-2 receptor chimera, J Immunol Methods. 337(1):16-23.
Soutschek et al., Nov. 11, 2004, Therapeutic silencing of an endogenous gene by systemic administration of modified siRNAs, Nature, 432:173-178.
Stankunas et al., Dec. 2003, Conditional protein alleles using knockin mice and a chemical inducer of dimerization, Mol. Cell., 12(6):1615-1624.
Tratschin et al., 1984, A human parvovirus, adeno-associated virus, as a eucaryotic vector: transient expression and encapsidation of the procaryotic gene for chloramphenicol acetyltransferase, Mol. Cell. Biol., 4(10):2072-2081.
Tratschin et al., Nov. 1985, Adeno-associated virus vector for high-frequency integration, expression, and rescue of genes in mammalian cells, Mol. Cell. Biol., 5(11):3251-3260.
Veverka et al., Structural Characterization of the interaction of mTOR with phosphatidic acid and a novel classs of inhibitor: compelling evidence for a central role of the FRB domain in small molecule-mediated regulation of mTOR, Oncogene, 27(5):585-595, (2008).
Vilella-Bach et al., Feb. 12, 1999, The FKBP12-reapamycin-binding domain is required for FSBP12-rapamycin-associated protein kinase activity and $G_1$ progression, J. Biol. Chem., 274(7):4266-4272.
Vivien et al., Mar. 31, 1995, Signaling activity of homologous and heterologous transforming growth factor-β receptor kinase complexes, J Biol Chem. 270(13):7134-7141.
Volkov et al., 2009, Selective protection of nuclease-sensitive sites in siRNA prolongs silencing effect, Oligonucleotides, 19(2):191-202.
Warren et al., 2010, Highly efficient reprogramming to pluripotency and directed differentiation of human cells with synthetic modified mRNA, Cell Stem Cell, 7(5):618-630.
Wells et al., Feb. 26, 1999, Transforming growth factor-β induces formation of dithiothreitol- resistant type I/type II receptor complex in live cells, J Biol Chem. 274(9):5716-5722.
Winkler, 2013, Oligonucleotide conjugates for therapeutic applications, Ther. Deliv., 4(7):791-809.
Wrana et al. Dec. 11, 1992, TGFβ signals through a heteromeric protein kinase receptor complex, Cell. 71(6):1003-1014.
International Search Report for PCT/US2017/065746 dated May 23, 2018.
Hu, Weihong, Aug. 31, 1989, Immunobiology, Xiamen University Press, 1st edition, p. 215.
Watanabe et al., 2017, Genetic visualization of protein interactions harnessing liquid phase transitions, Scientific Reports, 7:46380, 32 pp.
Zhao, Fuxi et al., Apr. 30, 2013, People's Military Medical Press, 1st edition, p. 119.

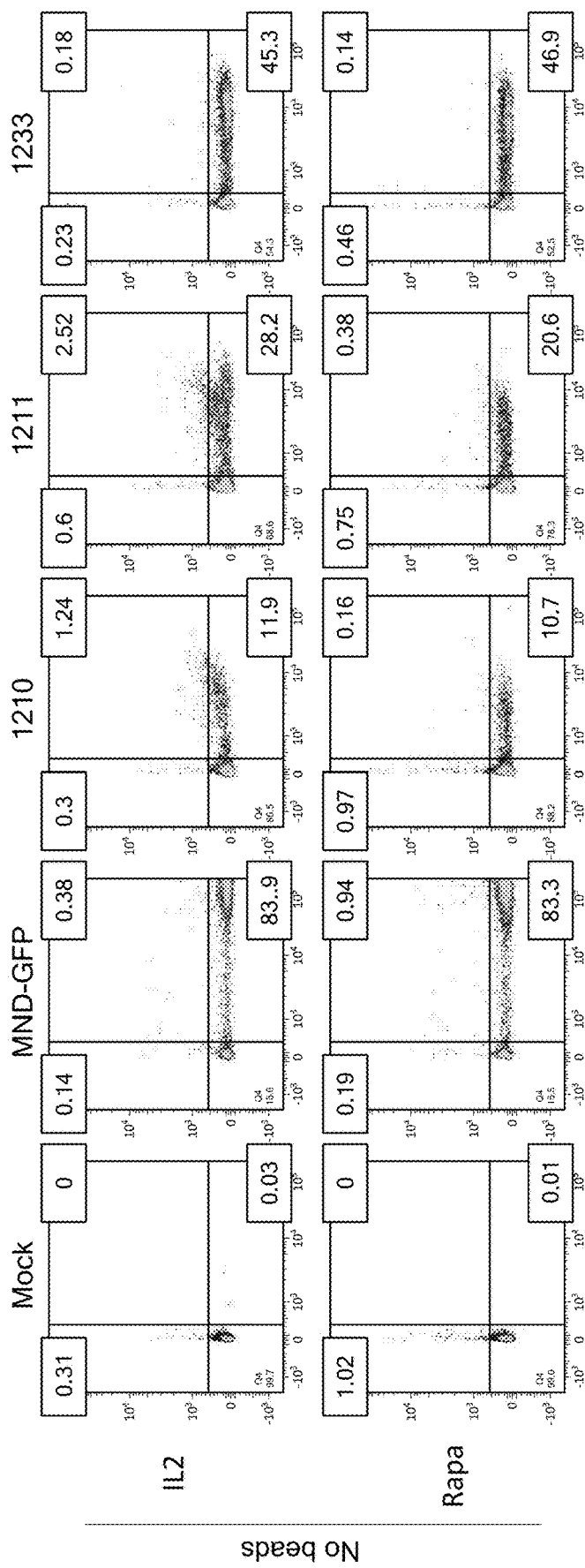
FIGURE 8 (Con'd)

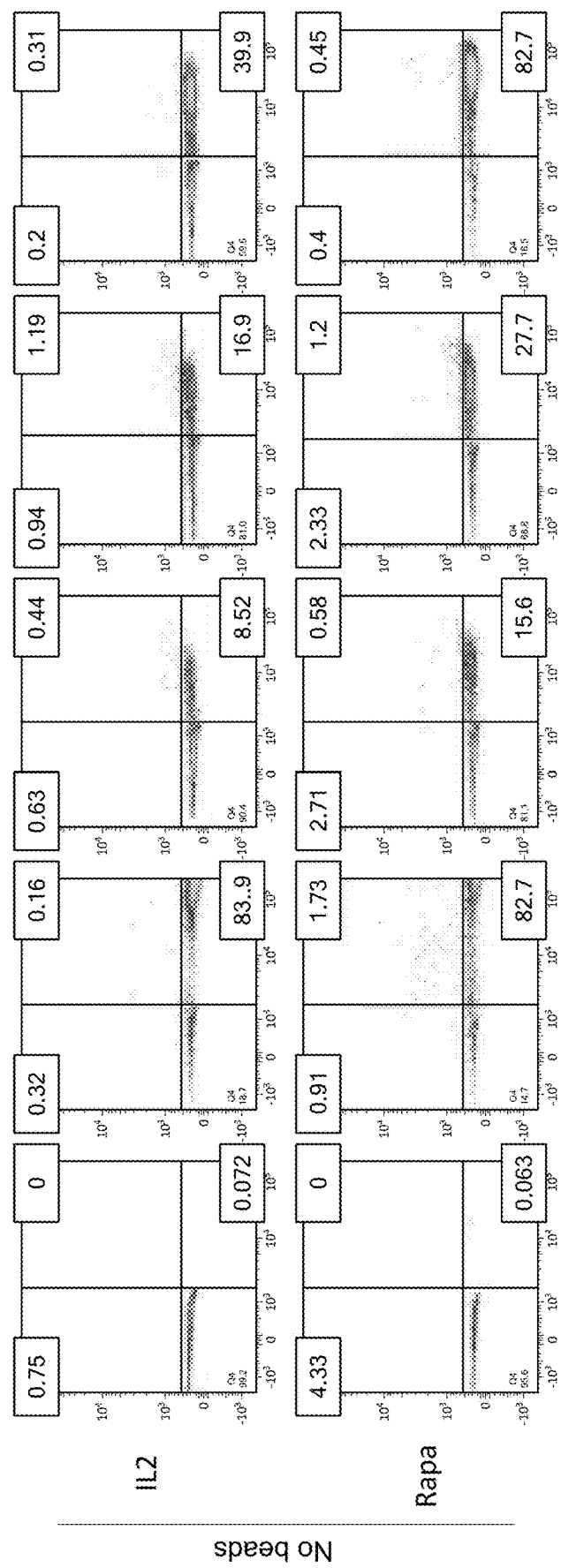
FIGURE 9 (Con'd)

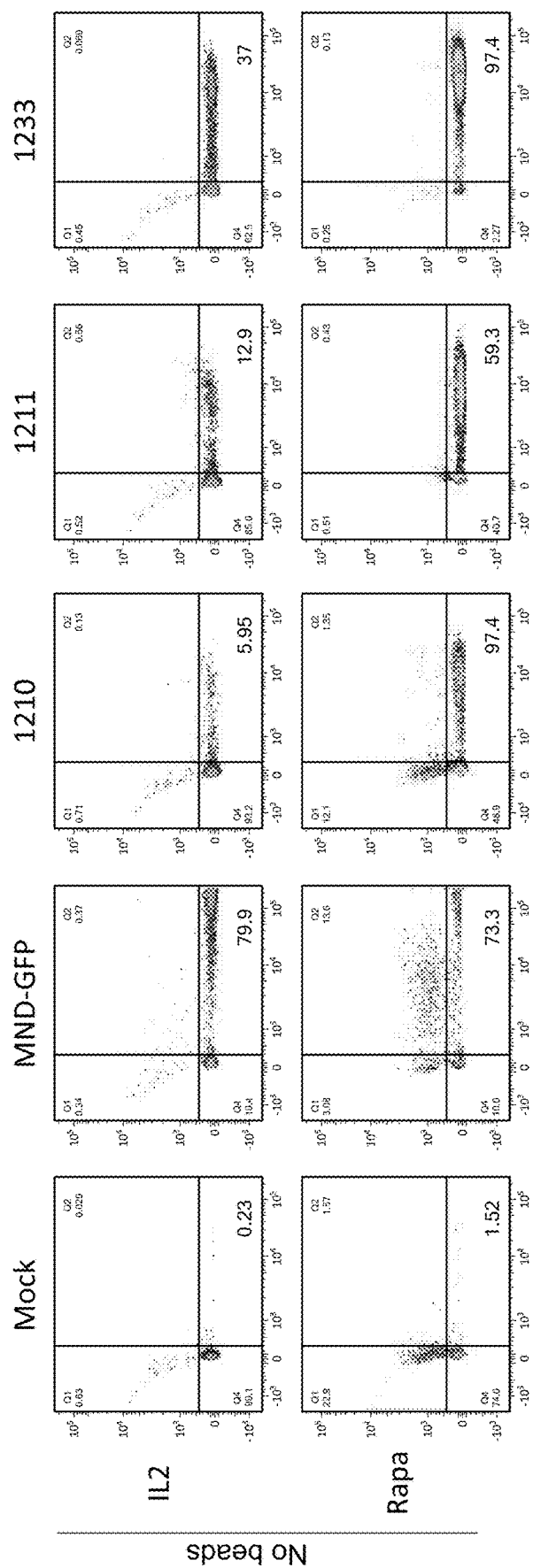
FIGURE 10 (Con'd)

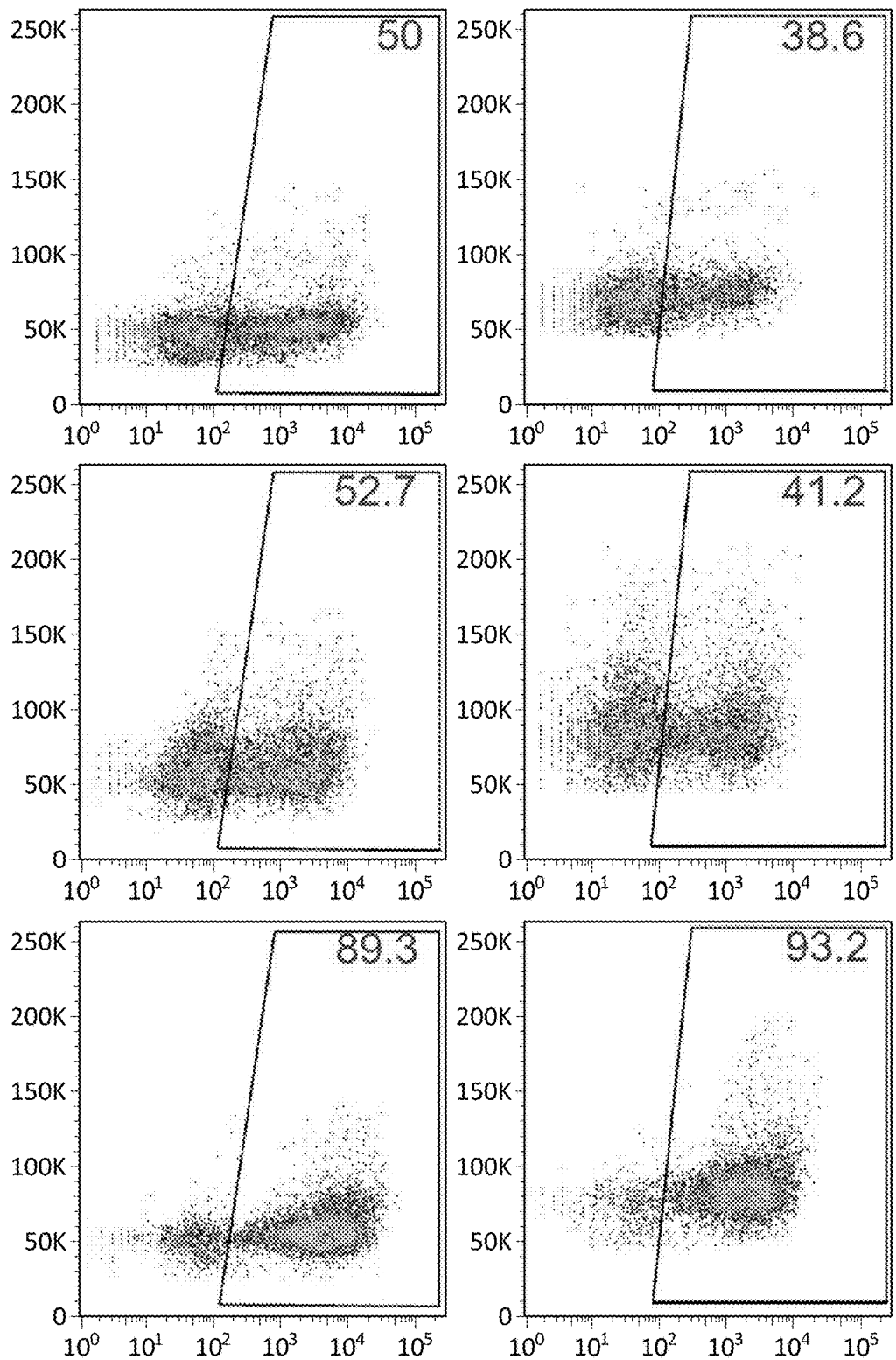
FIGURE 11 (Con'd)

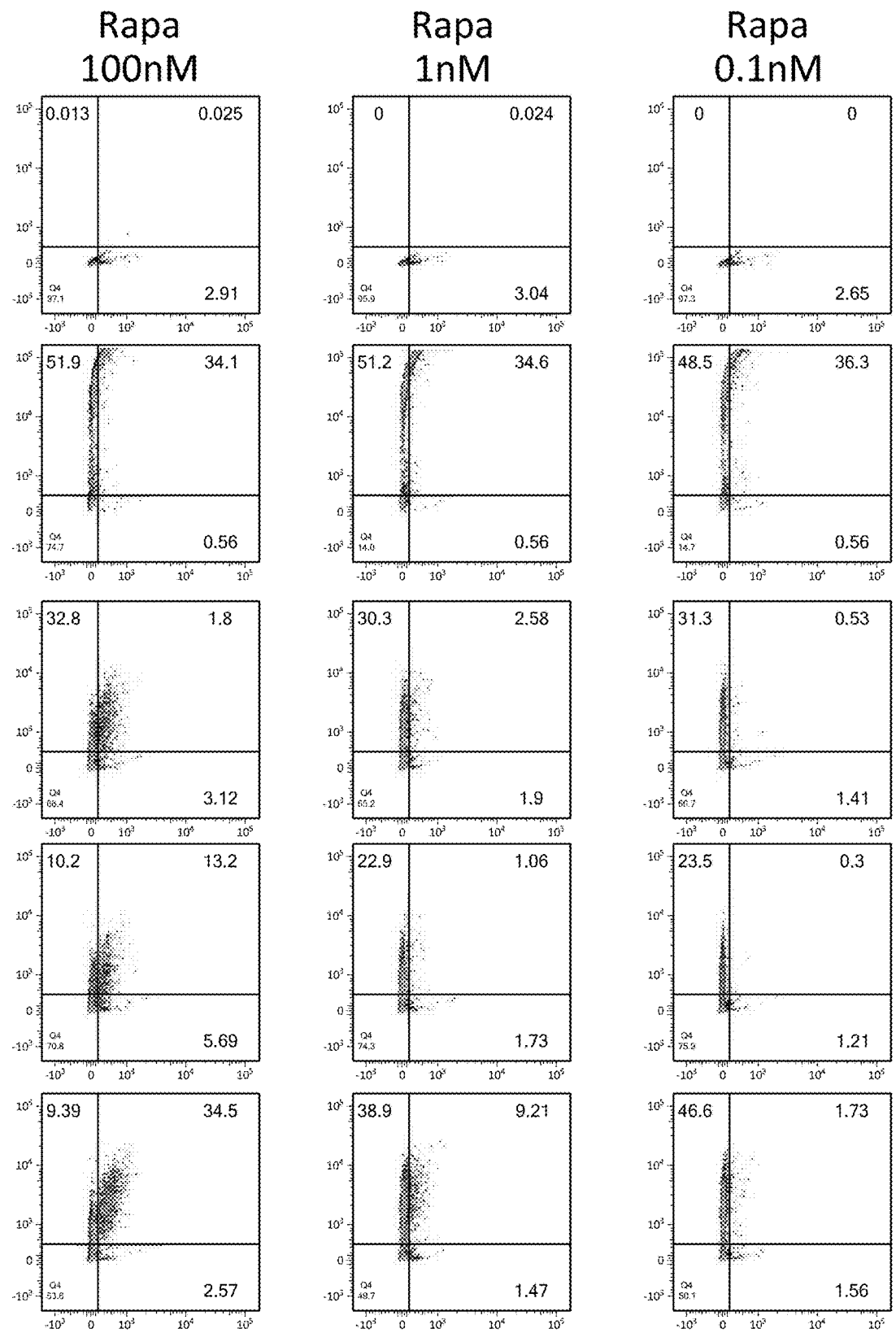
FIGURE 14 (Con'd)

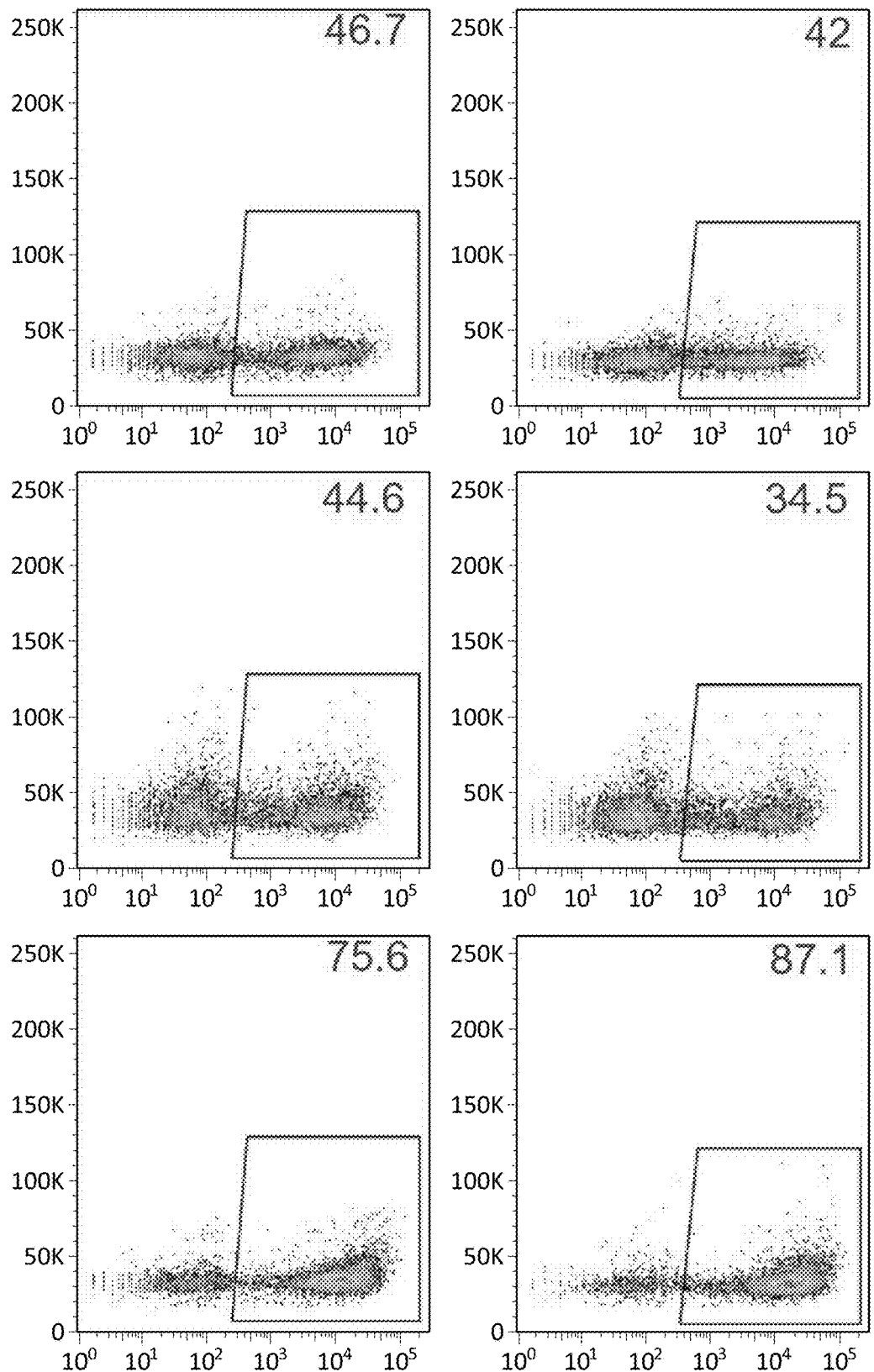
FIGURE 15 (Con'd)

SEQUENCE LISTING

```
Sequence total quantity: 20
SEQ ID NO: 1                moltype = AA   length = 251
FEATURE                     Location/Qualifiers
REGION                      1..251
                            note = IL2R-CISC - gamma component
source                      1..251
                            mol_type = protein
                            organism = synthetic construct
SEQUENCE: 1
MPLGLLWLGL ALLGALHAQA GVQVETISPG DGRTFPKRGQ TCVVHYTGML EDGKKFDSSR    60
DRNKPFKFML GKQEVIRGWE EGVAQMSVGQ RAKLTISPDY AYGATGHPGI IPPHATLVFD   120
VELLKLGEGS NTSKENPFLF ALEAVVISVG SMGLIISLLC VYFWLERTMP RIPTLKNLED   180
LVTEYHGNFS AWSGVSKGLA ESLQPDYSER LCLVSEIPPK GGALGEGPGA SPCNQHSPYW   240
APPCYTLKPE T                                                       251

SEQ ID NO: 2                moltype = AA   length = 429
FEATURE                     Location/Qualifiers
REGION                      1..429
                            note = IL2R-CISC - beta component
source                      1..429
                            mol_type = protein
                            organism = synthetic construct
SEQUENCE: 2
MALPVTALLL PLALLLHAAR PILWHEMWHE GLEEASRLYF GERNVKGMFE VLEPLHAMME    60
RGPQTLKETS FNQAYGRDLM EAQEWCRKYM KSGNVKDLLQ AWDLYYHVFR RISKGKDTIP   120
WLGHLLVGLS GAFGFIILVY LLINCRNTGP WLKKVLKCNT PDPSKFFSQL SSEHGGDVQK   180
WLSSPFPSSS FSPGGLAPEI SPLEVLERDK VTQLLLQQDK VPEPASLSSN HSLTSCFTNQ   240
GYFFPHLPDA LEIEACQVYF TYDPYSEEDP DEGVAGAPTG SSPQPLQPLS GEDDAYCTFP   300
SRDDLLLFSP SLLGGPSPPS TAPGGSGAGE ERMPPSLQER VPRDWDPQPL GPPTPGVPDL   360
VDFQPPPELV LREAGEEVPD AGPREGVSFP WSRPPGQGEF RALNARLPLN TDAYLSLQEL   420
QGQDPTHLV                                                          429

SEQ ID NO: 3                moltype = AA   length = 352
FEATURE                     Location/Qualifiers
REGION                      1..352
                            note = FKBP IL2Rg CISC 1210
source                      1..352
                            mol_type = protein
                            organism = synthetic construct
SEQUENCE: 3
MPLGLLWLGL ALLGALHAQA GVQVETISPG DGRTFPKRGQ TCVVHYTGML EDGKKFDSSR    60
DRNKPFKFML GKQEVIRGWE EGVAQMSVGQ RAKLTISPDY AYGATGHPGI IPPHATLVFD   120
VELLKLEGGS QNLVIPWAP ENLTLHKLSE SQLELNWNNR FLNHCLEHLV QYRTDWDHSW    180
TEQSVDYRHK FSLPSVDGQK RYTFRVRSRF NPLCGSAQHW SEWSHPIHWG SNTSKENPFL   240
FALEAVVISV GSMGLIISLL CVYFWLERTM PRIPTLKNLE DLVTEYHGNF SAWSGVSKGL   300
AESLQPDYSE RLCLVSEIPP KGGALGEGPG ASPCNQHSPY WAPPCYTLKP ET           352

SEQ ID NO: 4                moltype = AA   length = 544
FEATURE                     Location/Qualifiers
REGION                      1..544
                            note = FRB IL2Rb CISC 1210
source                      1..544
                            mol_type = protein
                            organism = synthetic construct
SEQUENCE: 4
MALPVTALLL PLALLLHAAR PILWHEMWHE GLEEASRLYF GERNVKGMFE VLEPLHAMME    60
RGPQTLKETS FNQAYGRDLM EAQEWCRKYM KSGNVKDLLQ AWDLYYHVFR RISKGGSKPF   120
ENLRLMAPIS LQVVHVETHR CNISWEISQA SHYFERHLEF EARTLSPGHT WEEAPLLTLK   180
QKQEWICLET LTPDTQYEFQ VRVKPLQGEF TTWSPWSQPL AFRTKPAALG KDTIPWLGHL   240
LVGLSGAFGF IILVYLLINC RNTGPWLKKV LKCNTPDPSK FFSQLSSEHG GDVQKWLSSP   300
FPSSSFSPGG LAPEISPLEV LERDKVTQLL LQQDKVPEPA SLSSNHSLTS CFTNQGYFFF   360
HLPDALEIEA CQVYFTYDPY SEEDPDEGVA GAPTGSSPQP LQPLSGEDDA YCTFPSRDDL   420
LLFSPSLLGG PSPPSTAPGG SGAGEERMPP SLQERVPRDW DPQPLGPPTP GVPDLVDFQP   480
PPELVLREAG EEVPDAGPRE GVSFPWSRPP GQGEFRALNA RLPLNTDAYL SLQELQGQDP   540
THLV                                                               544

SEQ ID NO: 5                moltype = AA   length = 349
FEATURE                     Location/Qualifiers
REGION                      1..349
                            note = FKBP IL2Rg CISC 1211
source                      1..349
                            mol_type = protein
                            organism = synthetic construct
SEQUENCE: 5
MPLGLLWLGL ALLGALHAQA GVQVETISPG DGRTFPKRGQ TCVVHYTGML EDGKKFDSSR    60
DRNKPFKFML GKQEVIRGWE EGVAQMSVGQ RAKLTISPDY AYGATGHPGI IPPHATLVFD   120
VELLKLEGQN LVIPWAPENL TLHKLSESQL ELNWNNRFLN HCLEHLVQYR TDWDHSWTEQ   180
SVDYRHKFSL PSVDGQKRYT FRVRSRFNPL CGSAQHWSEW SHPIHWGSNT SKENPFLFAL   240
```

```
EAVVISVGSM GLIISLLCVY FWLERTMPRI PTLKNLEDLV TEYHGNFSAW SGVSKGLAES     300
LQPDYSERLC LVSEIPPKGG ALGEGPGASP CNQHSPYWAP PCYTLKPET                349

SEQ ID NO: 6            moltype = AA  length = 541
FEATURE                 Location/Qualifiers
REGION                  1..541
                        note = FRB IL2Rb CISC 1211
source                  1..541
                        mol_type = protein
                        organism = synthetic construct
SEQUENCE: 6
MALPVTALLL PLALLLHAAR PILWHEMWHE GLEEASRLYF GERNVKGMFE VLEPLHAMME     60
RGPQTLKETS FNQAYGRDLM EAQEWCRKYM KSGNVKDLLQ AWDLYYHVFR RISKKPFENL     120
RLMAPISLQV VHVETHRCNI SWEISQASHY FERHLEFEAR TLSPGHTWEE APLLTLKQKQ     180
EWICLETLTP DTQYEFQVRV KPLQGEFTTW SPWSQPLAFR TKPAALGKDT IPWLGHLLVG     240
LSGAFGFIIL VYLLINCRNT GPWLKKVLKC NTPDPSKFFS QLSSEHGGDV QKWLSSPFPS     300
SSFSPGGLAP EISPLEVLER DKVTQLLLQQ DKVPEPASLS SNHSLTSCFT NQGYFFFHLP     360
DALEIEACQV YFTYDPYSEE DPDEGVAGAP TGSSPQPLQP LSGEDDAYCT FPSRDDLLLF     420
SPSLLGGPSP PSTAPGGSGA GEERMPPSLQ ERVPRDWDPQ PLGPPTPGVP DLVDFQPPPE     480
LVLREAGEEV PDAGPREGVS FPWSRPPGQG EFRALNARLP LNTDAYLSLQ ELQGQDPTHL     540
V                                                                   541

SEQ ID NO: 7            moltype = AA  length = 251
FEATURE                 Location/Qualifiers
REGION                  1..251
                        note = FKBP IL2Rg CISC 1233
source                  1..251
                        mol_type = protein
                        organism = synthetic construct
SEQUENCE: 7
MPLGLLWLGL ALLGALHAQA GVQVETISPG DGRTFPKRGQ TCVVHYTGML EDGKKFDSSR     60
DRNKPFKFML GKQEVIRGWE EGVAQMSVGQ RAKLTISPDY AYGATGHPGI IPPHATLVFD     120
VELLKLEGGS NTSKENPFLF ALEAVVISVG SMGLIISLLC VYFWLERTMP RIPTLKNLED     180
LVTEYHGNFS AWSGVSKGLA ESLQPDYSER LCLVSEIPPK GGALGEGPGA SPCNQHSPYW     240
APPCYTLKPE T                                                        251

SEQ ID NO: 8            moltype = AA  length = 379
FEATURE                 Location/Qualifiers
REGION                  1..379
                        note = FRB IL2Rb CISC 1233
source                  1..379
                        mol_type = protein
                        organism = synthetic construct
SEQUENCE: 8
MALPVTALLL PLALLLHAAR PILWHEMWHE GLEEASRLYF GERNVKGMFE VLEPLHAMME     60
RGPQTLKETS WLGHLLVGLS GAFGFIILVY LLINCRNTGP WLKKVLKCNT PDPSKFFSQL     120
SSEHGGDVQK WLSSPFPSSS FSPGGLAPEI SPLEVLERDK VTQLLLQQDK VPEPASLSSN     180
HSLTSCFTNQ GYFFFHLPDA LEIEACQYVF TYDPYSEEDP DEGVAGAPTG SSPQPLQPLS     240
GEDDAYCTFP SRDDLLLFSP SLLGGPSPPS TAPGGSGAGE ERMPPSLQER VPRDWDPQPL     300
GPPTPGVPDL VDFQPPPELV LREAGEEVPD AGPREGVSFP WSRPPGQGEF RALNARLPLN     360
TDAYLSLQEL QGQDPTHLV                                                379

SEQ ID NO: 9            moltype = AA  length = 345
FEATURE                 Location/Qualifiers
REGION                  1..345
                        note = FRB IL7Ra CISC
source                  1..345
                        mol_type = protein
                        organism = synthetic construct
SEQUENCE: 9
MALPVTALLL PLALLLHAAR PILWHEMWHE GLEEASRLYF GERNVKGMFE VLEPLHAMME     60
RGPQTLKETS FNQAYGRDLM EAQEWCRKYM KSGNVKDLLQ AWDLYYHVFR RISKGEINNS     120
SGEMDPILLT ISILSFFSVA LLVILACVLW KKRIKPIVWP SLPDHKKTLE HLCKKPRKNL     180
NVSFNPESFL DCQIHRVDDI QARDEVEGFL QDTFPQQLEE SEKQRLGGDV QSPNCPSEDV     240
VITPESFGRD SSLTCLAGNV SACDAPILSS SRSLDCRESG KNGPHVYQDL LLSLGTTNST     300
LPPPFSLQSG ILTLNPVAQG QPILTSLGSN QEEAYVTMSS FYQNQ                    345

SEQ ID NO: 10           moltype = AA  length = 443
FEATURE                 Location/Qualifiers
REGION                  1..443
                        note = FKBP-F36V IL2Rb CISC
source                  1..443
                        mol_type = protein
                        organism = synthetic construct
SEQUENCE: 10
MPLGLLWLGL ALLGALHAQA GVQVETISPG DGRTFPKRGQ TCVVHYTGML EDGKKVDSSR     60
DRNKPFKFML GKQEVIRGWE EGVAQMSVGQ RAKLTISPDY AYGATGHPGI IPPHATLVFD     120
VELLKLEGGK DTIPWLGHLL VGLSGAFGFI ILVYLLINCN NTGPWLKKVL KCNTPDPSKF     180
FSQLSSEHGG DVQKWLSSPF PSSSFSPGGL APEISPLEVL ERDKVTQLLL QQDKVPEPAS    240
```

```
LSSNHSLTSC FTNQGYFFFH LPDALEIEAC QVYFTYDPYS EEDPDEGVAG APTGSSPQPL    300
QPLSGEDDAY CTFPSRDDLL LFSPSLLGGP SPPSTAPGGS GAGEERMPPS LQERVPRDWD    360
PQPLGPPTPG VPDLVDFQPP PELVLREAGE EVPDAGPREG VSFPWSRPPG QGEFRALNAR    420
LPLNTDAYLS LQELQGQDPT HLV                                           443

SEQ ID NO: 11            moltype = AA   length = 251
FEATURE                  Location/Qualifiers
REGION                   1..251
                         note = FKBP-F36V IL2Rg CISC 1233
source                   1..251
                         mol_type = protein
                         organism = synthetic construct
SEQUENCE: 11
MPLGLLWLGL ALLGALHAQA GVQVETISPG DGRTFPKRGQ TCVVHYTGML EDGKKVDSSR     60
DRNKPFKFML GKQEVIRGWE EGVAQMSVGQ RAKLTISPDY AYGATGHPGI IPPHATLVFD    120
VELLKLEGGS NTSKENPFLF ALEAVVISVG SMGLIISLLC VYFWLERTMP RIPTLKNLED    180
LVTEYHGNFS AWSGVSKGLA ESLQPDYSER LCLVSEIPPK GGALGEGPGA SPCNQHSPYW    240
APPCYTLKPE T                                                        251

SEQ ID NO: 12            moltype = AA   length = 358
FEATURE                  Location/Qualifiers
REGION                   1..358
                         note = FKBP-F36V IL7Ra CISC 1
source                   1..358
                         mol_type = protein
                         organism = synthetic construct
SEQUENCE: 12
MPLGLLWLGL ALLGALHAQA GVQVETISPG DGRTFPKRGQ TCVVHYTGML EDGKKVDSSR     60
DRNKPFKFML GKQEVIRGWE EGVAQMSVGQ RAKLTISPDY AYGATGHPGI IPPHATLVFD    120
VELLKLEGEI NNSSGEMDPI LLTISILSFF SVALLVILAC VLWKKRIKPI VWPSLPDHKK    180
TLEHLCKKPR KNLNVSFNPE SFLDCQIHRV DDIQARDEVE GFLQDTFPQQ LEESEKQRLG    240
GDVQSPNCPS EDVVITPESF GRDSSLTCLA GNVSACDAPI LSSSRSLDCR ESGKNGPHVY    300
QDLLLSLGTT NSTLPPPFSL QSGILTLNPV AQGQPILTSL GSNQEEAYVT MSSFYQNQ     358

SEQ ID NO: 13            moltype = AA   length = 358
FEATURE                  Location/Qualifiers
REGION                   1..358
                         note = FKBP-F36V IL7Ra CISC 2
source                   1..358
                         mol_type = protein
                         organism = synthetic construct
SEQUENCE: 13
MPLGLLWLGL ALLGALHAQA GVQVETISPG DGRTFPKRGQ TCVVHYTGML EDGKKVDSSR     60
DRNKPFKFML GKQEVIRGWE EGVAQMSVGQ RAKLTISPDY AYGATGHPGI IPPHATLVFD    120
VELLKLEGEI NNSSGEMDPI LLTISILSFF SVALLVILAC VLWKKRIKPI VWPSLPDHKK    180
TLEHLCKKPR KNLNVSFNPE SFLDCQIHRV DDIQARDEVE GFLQDTFPQQ LEESEKQRLG    240
GDVQSPNCPS EDVVITPESF GRDSSLTCLA GNVSACDAPI LSSSRSLDCR ESGKNGPHVY    300
QDLLLSLGTT NSTLPPPFSL QSGILTLNPV AQGQPILTSL GSNQEEAYVT MSSFYQNQ     358

SEQ ID NO: 14            moltype = AA   length = 276
FEATURE                  Location/Qualifiers
REGION                   1..276
                         note = FKBP-F36V MPL
source                   1..276
                         mol_type = protein
                         organism = synthetic construct
SEQUENCE: 14
MPLGLLWLGL ALLGALHAQA GVQVETISPG DGRTFPKRGQ TCVVHYTGML EDGKKVDSSR     60
DRNKPFKFML GKQEVIRGWE EGVAQMSVGQ RAKLTISPDY AYGATGHPGI IPPHATLVFD    120
VELLKLGEET AWISLVTALH LVLGLSAVLL LLLRWQFPA HYRRLRHALW PSLPDLHRVL     180
GQYLRDTAAL SPPKATVSDT CEEVEPSLLE ILPKSSERTP LPLCSSQAQM DYRRLQPSCL    240
GTMPLSVCPP MAESGSCCTT HIANHSYLPL SYWQQP                              276

SEQ ID NO: 15            moltype = AA   length = 4
FEATURE                  Location/Qualifiers
REGION                   1..4
                         note = Glycine spacer 1
source                   1..4
                         mol_type = protein
                         organism = synthetic construct
SEQUENCE: 15
GGGS                                                                   4

SEQ ID NO: 16            moltype = AA   length = 7
FEATURE                  Location/Qualifiers
REGION                   1..7
                         note = Glycine spacer 2
source                   1..7
                         mol_type = protein
```

|  |  |  |  |  |  |
|---|---|---|---|---|---|
| | | organism = synthetic construct | | | |
| SEQUENCE: 16 | | | | | |
| GGGSGGG | | | | | 7 |

SEQ ID NO: 17           moltype =     length =
SEQUENCE: 17
000

SEQ ID NO: 18           moltype = DNA  length = 10035
FEATURE                 Location/Qualifiers
misc_feature            1..10035
                        note = IL2Rg upstream of IL2Rb
source                  1..10035
                        mol_type = other DNA
                        organism = synthetic construct
SEQUENCE: 18

| | | | | | |
|---|---|---|---|---|---|
| agcttaatgt | agtcttatgc | aatactcttg | tagtcttgca | acatggtaac | gatgagttag | 60 |
| caacatgcct | tacaaggaga | gaaaaagcac | cgtgcatgcc | gattggtgga | agtaaggtgg | 120 |
| tacgatcgtg | ccttattagg | aaggcaacag | acgggtctga | catggattgg | acgaaccact | 180 |
| gaattgccgc | attgcagaga | tatttgtattt | aagtgcctag | ctcgatacaa | taaacgggtc | 240 |
| tctctggtta | gaccagatct | gagcctggga | gctctctggc | taactaggga | acccactgct | 300 |
| taagcctcaa | taaagcttgc | cttgagtgct | tcaagtagtg | tgtgcccgtc | tgttgtgtga | 360 |
| ctctggtaac | tagagatccc | tcagacccct | ttagtcagtg | tggaaaatct | ctagcagtgg | 420 |
| cgcccgaaca | gggacttgaa | agcgaaaggg | aaaccagagg | agctctctcg | acgcaggact | 480 |
| cggcttgctg | aagcgcgcac | ggcaagaggc | gaggggcggc | gactggtgag | tacgccaaaa | 540 |
| attttgacta | gcggaggcta | gaaggagaga | gatgggtgcg | agagcgtcag | tattaagcgg | 600 |
| gggagaatta | gatcgcgatg | ggaaaaaatt | cggttaaggc | caggggggaaa | gaaaaaatat | 660 |
| aaattaaaac | atatagtatg | ggcaagcagg | gagctagaac | gattcgcagt | taatcctggc | 720 |
| ctgttagaaa | catcagaagg | ctgtagacaa | atactgggac | agctacaacc | atcccttcag | 780 |
| acaggatcag | aagaacttag | atcattatat | aatacagtag | caaccctcta | ttgtgtgcat | 840 |
| caaaggatag | agataaaaga | caccaaggaa | gctttagaca | agatagagga | agagcaaaac | 900 |
| aaaagtaaga | ccaccgcaca | gcaagcggcc | gctgatcttc | agacctggag | gaggagatat | 960 |
| gagggacaat | tggagaagtg | aattatataa | atataaagta | gtaaaattg | aaccattagg | 1020 |
| agtagcaccc | accaaggcaa | agagaagagt | ggtgcagaga | gaaaaaagag | cagtgggaat | 1080 |
| aggagctttg | ttccttgggt | tcttgggagc | agcaggaagc | actatgggcg | cagcctcaat | 1140 |
| gacgctgacg | gtacaggcca | gacaattatt | gtctggtata | gtgcagcagc | agaacaattt | 1200 |
| gctgagggct | attgaggcgc | aacagcatct | gttgcaactc | acagtctggg | gcatcaagca | 1260 |
| gctccaggca | agaatcctgg | ctgtggaaag | atacctaaag | gatcaacagc | tcctggggat | 1320 |
| ttggggttgc | tctggaaaac | tcatttgcac | cactgctgtg | ccttgaatg | ctagttggag | 1380 |
| taataaatct | ctggaacaga | tttgaatca | cacgacctgg | atggagtggg | acagagaaat | 1440 |
| taacaattac | acaagcttaa | tacactcctt | aattgaagaa | tcgcaaaacc | agcaagaaaa | 1500 |
| gaatgaacaa | gaattattgg | aattagataa | atgggcaagt | ttgtggaatt | ggtttaacat | 1560 |
| aacaaattgg | ctgtggtata | taaaaattatt | cataatgata | gtaggaggct | tggtaggttt | 1620 |
| aagaatagtt | tttgctgtac | tttctatagt | gaatagagtt | aggcagggat | attcaccatt | 1680 |
| atcgtttcag | acccacctcc | caaccccgag | gggacccgac | aggcccgaag | gaatagaaga | 1740 |
| agaaggtgga | gagagagaca | gagacagatc | cattcgatta | gtgaacggat | ctcgacggta | 1800 |
| tcggttaact | tttaaaagaa | aaggggggat | tggggggtac | agtgcagggg | aaagaatagt | 1860 |
| agacataata | gcaacagaca | tacaaactaa | agaattacaa | aaacaaatta | caaaaattca | 1920 |
| aaattttatc | gatcacgaga | ctagcctcga | agcttgat | atcgaattcc | cacggggttg | 1980 |
| gacgcgtagg | aacagagaaa | caggagaata | tgggccaaac | aggatatctg | tggtaagcag | 2040 |
| ttcctgcccc | ggctcagggc | caagaacagt | tggaacagca | gaatatggcc | caaacaggat | 2100 |
| atctgtggta | agcagttcct | gccccggctc | agggccaaga | acagatggtc | cccagatgcc | 2160 |
| gtcccgccct | cagcagtttc | tagagaacca | tcagatgttt | ccagggtgcc | ccaaggacct | 2220 |
| gaaatgaccc | tgtgccttat | ttgaactaac | caatcagttc | gcttctcgct | tctgttcgcg | 2280 |
| cgcttctgct | ccccgagctc | tatataagca | gagctcgttt | agtgaaccgt | cagatcgcta | 2340 |
| gcaccggtgc | cgccaccatg | cctctgggcc | tgctgtggct | gggcctggcc | ctgctgggcg | 2400 |
| ccctgcacgc | ccaggccggc | gtgcaggtgg | agacaatctc | cccaggcgac | ggacgcacat | 2460 |
| tccctaagcg | ggggccagacc | tgcgtggtgc | actatacagg | catgctggag | gatgccaaga | 2520 |
| agtttgacag | ctcccgggat | agaaacaagc | cattcaagtt | tatgctgggc | aagcaggaag | 2580 |
| tgatcagagg | ctgggaggag | ggcgtggccc | agatgtctgt | gggccagagg | gccaagctga | 2640 |
| ccatcagccc | agactacgcc | tatggagcaa | caggccaccc | aggaatcatc | ccacctcacg | 2700 |
| ccaccctggt | gttcgatgtg | gagctgctga | agctgggcga | gcaaaacttg | gtgattcctt | 2760 |
| gggcccccaga | aaatctcacg | cttcacaagt | tgtccgaatc | ccagctcgag | ctcaactgga | 2820 |
| ataatagatt | tcttaatcat | tgtttggaac | acctggttca | atatagaacg | gattggacc | 2880 |
| actcatggac | cgagcagtca | gttgactacc | gccacaaatt | tcacttccc | agcgtagatg | 2940 |
| ggcagaagag | gtacacattt | agggtcagat | ccagtttaa | tcctctgtgt | ggttctgctc | 3000 |
| aacactggtc | tgagtggagc | catccgatcc | actgggctc | aaataccctct | aaagaaatc | 3060 |
| cgttcctctt | tgcgctcgaa | gccgttgtta | tcagcgtcgg | aagcatggga | cttatcattt | 3120 |
| ccccttctctg | cgtgtacttc | tggctggagc | ggacgatgcc | gcggattccg | acgctcaaaa | 3180 |
| acctggagga | ccttgtaaca | gaatatcacg | gtaatttctc | cgcttggagt | ggcgtatcaa | 3240 |
| aggggcttgc | tgagtccctt | caaccggatt | actctgagcg | cctctgcttg | gtgtccgaga | 3300 |
| tacctcccaa | aggaggtgca | cttgggggagg | ggccaggcgc | gtcccttgc | aatcagcata | 3360 |
| gtccgtattg | gcgcccccc | tgttataccc | tcaaaccgga | aacgggaagc | ggagctacta | 3420 |
| acttcagcct | gctgaagcag | gctgagacg | tggaaggaga | ccctgagacc | atggcactga | 3480 |
| ccgtgaccgc | cctgctgctg | cctctggcc | tgctgctgca | cgcagccgg | cctatcctgt | 3540 |
| ggcacgagat | gtggcacgag | ggcctggagg | aggccagcag | gctgtattt | ggcgagcgca | 3600 |
| acgtgaaggg | catgttcgag | gtgctggagc | ctcgcacgc | catgatggag | agaggccac | 3660 |
| agaccctgaa | ggagacatcc | tttaaccagg | cctatgacg | ggacctgatg | gaggcacagg | 3720 |
| agtggtgcag | aaagtacatg | aagtctggca | atgtgaagga | cctgctgcag | gcctgggatc | 3780 |

```
tgtactatca cgtgtttcgg agaatctcca agaaaccttt tgagaacctt agactgatgg   3840
cgcccatctc tctgcaggta gttcacgttg agcccatag atgcaatata agctgggaaa   3900
tctcacaagc cagccattac tttgaacggc atttggaatt cgaggcccga acactttccc   3960
ccggtcatac gtgggaagaa gctcctctct tgacgctgaa gcagaagcag gagtggattt   4020
gtctggagac tttgactcct gatactcagt atgagttcca agttcgggtg aaaccactcc   4080
aaggcgagtt cacgacgtgg tctccgtgga gtcaaccgtt ggcgttccgc acgaagcccg   4140
ctgcccttgg caaagacacg attccgtggc ttgggcatct gctcgttggg ctgagtggtg   4200
cgtttggttt catcatcttg gtctatctct tgatcaattg cagaaataca ggcccttggc   4260
tgaaaaaagt gctcaagtgt aataccccg acccaagcaa gttcttctcc cagcttcctt   4320
cagagcatgg aggcgatgtg cagaaatggc tctcttcacc tttccctcc tcaagcttct   4380
ccccgggagg gctggcgccc gagatttcac ctcttgaggt acttgaacga gacaaggtta   4440
cccaacttct ccttcaacag gataaggtac ccgaacctgc gagccttagc tccaaccact   4500
ctcttacgag ctgcttcacc aatcagggat acttcttttt ccaccttccc gatgcgctgg   4560
aaatcgaagc ttgtcaagtt tactttacct atgatccata tagcgaggaa gatcccgacg   4620
aaggagtcgc cggtgcgccc acgggttcct caccccaacc tctccagcct ctctcaggag   4680
aagatgatgc ttattgcact tttcccagta gagacgatct cctcctcttt tctccatctc   4740
ttttgggggg accttccccc ccttctacgg cacctggcgg gtctggtgct ggcgaggagc   4800
ggatgccgcc gtccctccag gagcgagtac cacgagattg ggatcccccag ccacttggac   4860
cccccacccc cggcgtacct gaccttgtcg attttcaacc tccccctgaa ttggtgctgc   4920
gagaggctgg ggaggaagtt ccggacgctg gccgaggga gggcgtgtcc tttccatgga   4980
gtaggcctcc aggtcaaggc gagtttaggg ctctcaacgc gcggctgccg ttgaatacag   5040
acgcttatct ctcactgcag gaactgcaag gtcaggaccc aacacatctt ataggatctg   5100
gtgctactaa ttttttctctt ttgaagcaag ctggagatgt tgaagagaac cctggtccga   5160
tgagcaaggg cgaggagctg ttcaccgggg tggtgcccat cctggtcgag ctggacggcg   5220
acgtaaacgc ccacaagttc agcgtgtccg gcgagggcga gggcgatgcc acctacggca   5280
agctgaccct gaagttcatc tgcaccaccg gcaagctgcc cgtgccctgc ccacccttg   5340
tgaccaccct gacctacggc gtgcagtgct tcagccgcta ccccgaccac atgaagcagc   5400
acgacttctt caagtccgcc atgcccgaag gctacgtcca ggagcgcacc atcttcttca   5460
aggacgacgg caactacaag acccgcgccg aggtgaagtt cgaggcgac accctggtga   5520
accgcatcga gctgaagggc atcgacttca aggaggacgg caacatcctg gggcacaagc   5580
tggagtacaa ctacaacagc cacaacgtct atatcatggc cgacaagcag aagaacggca   5640
tcaaggtgaa cttcaagatc cgccacaaca tcgaggacgg cagcgtgcag ctcgccgacc   5700
actaccagca gaacaccccc atcggcgacg gccccgtgct gctgcccgac aaccactacc   5760
tgagcaccca gtccgccctg agcaaagacc ccaacgagaa gcgcgatcac atggtcctgc   5820
tggagttcgt gaccgccgcc gggatcactc tcggcatgga cgagctgtac aagtaaaacta   5880
gtgtcgacaa tcaacctctg gattacaaaa tttgtgaaag attgactggt attcttaact   5940
atgttgctcc ttttacgcta tgtggatacg ctgctttaat gcctttgtat catgctattg   6000
cttccgtat ggctttcatt ttctcctcct tgtataaatc ctggttgctg tctctttatg   6060
aggagttgtg gcccgttgtc aggcaacgtg gcgtggtgtg cactgtgttt gctgacgcaa   6120
ccccccactgg ttggggcatt gccaccacct gtcagctcct ttccgggact ttcgctttcc   6180
ccctccctat tgccacggcg gaactcatcg ccgcctgcct tgcccgctgc tggacagggg   6240
ctcggctgtt gggcactgac aattccgtgg tgttgtcggg gaagctgacg tccttttccat   6300
ggctgctcgc ctgtgttgcc acctggattc tgcgcgggac ttgtgcctt tacgtccctt   6360
cggccctcaa tccagcggac cttcttccc gcggcctgct gccggctctg cggcctcttc   6420
cgcgtcttcg ccttcgccct cagacgagtc ggatctcccct ttgggccgcc tccccgcctg   6480
gaattcgagc tcggtacctt taagaccaat gacttacaag gcagctgtag atcttagcca   6540
cttttttaaaa gaaaaggggg gactggaagg gctaattcac tcccaacgaa gacaagatct   6600
gctttttgct tgtactgggt ctctctggtt agaccagatc tgagcctggg agctctctgg   6660
ctaactaggg aacccactgc ttaagcctca ataaagcttg ccttgagtgc ttcaagtagt   6720
gtgtgcccgt ctgttgtgtg actctggtaa ctagagatcc ctcagaccct tttagtcagt   6780
gtggaaaatc tctagcagta gtagttcatg tcatcttatt attcagtatt tataacttgc   6840
aaagaaatga atatcagaga gtgagaggaa cttgtttatt gcagcttata atggttacaa   6900
ataaagcaat agcatcacaa atttcacaaa taaagcatt ttttcactgc attctagttg   6960
tggtttgtcc aaactcatca atgtatctta tcatgtctgg ctctagctat cccgccccta   7020
actccgccca gttccgccca ttctccgccc catggctgac taatttttttt tatttatgca   7080
gaggccgagg ccgcctcggc ctctgagcta ttccagaagt agtgaggagg cttttttgga   7140
ggcctaggct tttgcgtcga cgtaccca attcgcccta tagtgagtcg tattacgcgc   7200
gctcactggc cgtcgtttta caacgtcgtg actgggaaaa ccctggcgtt acccaactta   7260
atcgccttgc agcacatccc cctttcgcca gctggcgtaa tagcgaagag gcccgcaccg   7320
atcgcccttc ccaacagttg cgcagcctga atggcgaatg gcgcacgcg ccctagcgc    7380
gcgcattaag cgcggcgggt gtggtggtta cgcgcagcgt gaccgctaca cttgccagcg   7440
ccctagcgcc cgctcctttc gctttcttcc cttcctttct cgccacgttc gccggctttc   7500
cccgtcaagc tctaaatcgg gggctccctt tagggttccg atttagtgct ttacggcacc   7560
tcgaccccaa aaaacttgat tagggtgatg gttcacgtag cgggccatcg cccctgataga   7620
cggttttcg ccctttgacg ttggagtcca cgttctttaa tagtggactc ttgttccaaa    7680
ctggaacaac actcaaccct atctcggtct attctttga tttataaggg attttgccga   7740
tttcggccta ttggttaaaa aatgagctga tttaacaaaa atttaacgcg aattttaaca   7800
aaatattaac gtttacaatt tcccaggtgg cacttttcgg ggaaatgtgc gcggaacccc   7860
tatttgttta tttttctaaa tacattcaaa tatgtatccg ctcatgagac aataaccctg   7920
ataaatgctt caataatatt gaaaaggaa gagtatgagt attcaacatt tccgtgtcgc   7980
ccttattccc ttttttgcgg cattttgcct tcctgttttt gctcacccag aaacgctggt   8040
gaaagtaaaa gatgctgaag atcagttggg tgcacgagtg ggttacatcg aactggatct   8100
caacagcggt aagatccttg agagttttcg ccccgaagaa cgttttccaa tgatgagcac   8160
ttttaaagtt ctgctatgtg gcgcggtatt atcccgtatt gacgccgggc aagagcaact   8220
cggtcgccgc atacactatt ctcagaatga cttggttgag tactcaccag tcacagaaaa   8280
gcatcttacg gatggcatga cagtaagaga attatgcagt gctgccataa ccatgagtga   8340
taacactgcg gccaacttac ttctgacaac gatcggagga ccgaaggagc taaccgcttt   8400
tttgcacaac atgggggatc atgtaactcg ccttgatcgt tgggaaccgg agctgaatga   8460
agccatacca aacgacgagc gtgacaccac gatgcctgta gcaatggcaa caacgttgcg   8520
```

```
caaactatta actggcgaac tacttactct agcttcccgg caacaattaa tagactggat   8580
ggaggcggat aaagttgcag gaccacttct gcgctcggcc cttccggctg ctggtttat   8640
tgctgataaa tctggagccg gtgagcgtgg gtctcgcgt atcattgcag cactggggcc   8700
agatggtaag ccctcccgta tcgtagttat ctacacgacg gggagtcagg caactatgga   8760
tgaacgaaat agacagatcg ctgagatagg tgcctcactg attaagcatt ggtaactgtc   8820
agaccaagtt tactcatata tactttagat tgatttaaaa cttcatttt aatttaaaag   8880
gatctaggtg aagatccttt ttgataatct catgaccaaa atcccttaac gtgagttttc   8940
gttccactga gcgtcagacc ccgtagaaaa gatcaaagga tcttcttgag atcctttttt   9000
tctgcgcgta atctgctgct tgcaaacaaa aaaaccaccg ctaccagcgg tggtttgttt   9060
gccggatcaa gagctaccaa ctcttttcc gaaggtaact ggcttcagca gagcgcagat   9120
accaaatact gtccttctag tgtagccgta gttaggccac cacttcaaga actctgtagc   9180
accgcctaca tacctcgctc tgctaatcct gttaccagtg gctgctgcca gtggcgataa   9240
gtcgtgtctt accgggttgg actcaagacg atagttaccg gataaggcgc agcggtcggg   9300
ctgaacgggg ggttcgtgca cacagcccag cttggagcga acgacctaca ccgaactgag   9360
atacctacag cgtgagctat gagaaagcgc cacgcttccc gaaggagaa aggcggacag   9420
gtatccgta agcggcaggg tcggaacagg agagcgcacg agggagcttc caggggaaa   9480
cgcctggtat ctttatagtc ctgtcgggtt tcgccacctc tgacttgagc gtcgatttt   9540
gtgatgctcg tcagggggc ggagcctatg gaaaaacgcc agcaacgcgg ccttttacg   9600
gttcctggcc ttttgctggc cttttgctca catgttcttt cctgcgttat cccctgattc   9660
tgtgataac cgtattaccg cctttgagtg agctgatacc gctcgccgca gccgaacgac   9720
cgagcgcagc gagtcagtga gcgaggaagc ggaagagcgc ccaatacgca aaccgcctct   9780
ccccgcgcgt tggccgattc attaatgcag ctggcacgac aggtttcccg actggaaagc   9840
gggcagtgag cgcaacgcaa ttaatgtgag ttagctcact cattaggcac cccaggcttt   9900
acactttatg cttccggctc gtatgttgtg tggaattgtg agcggataac aatttcacac   9960
aggaaacagc tatgaccatg attacgccaa gcgcgcaatt aaccctcact aaagggaaca  10020
aaagctggag ctgca                                                   10035

SEQ ID NO: 19          moltype = DNA  length = 10053
FEATURE                Location/Qualifiers
misc_feature           1..10053
                       note = IL2Rg upstream of IL2Rb
source                 1..10053
                       mol_type = other DNA
                       organism = synthetic construct
SEQUENCE: 19
agcttaatgt agtcttatgc aatactcttg tagtcttgca acatggtaac gatgagttag     60
caacatgcct tacaaggaga gaaaagcac cgtgcatgcc gattggtgga agtaaggtgg    120
tacgatcgtg ccttattagg aaggcaacag acgggtctga catggattgg acgaaccact    180
gaattgccgc attgcagaga tattgtattt aagtgcctag ctcgatacaa taaacgggct    240
tctctggtta gaccagatct gagcctggga gctctctggc taactaggga acccactgct    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gagggggcggc gactggtgag tacgccaaaa    540
attttgacta gcggaggcta aaggagaga gatgggtgcg agagcgtcag tattaagcgg    600
gggagaatta gatcgcgatg ggaaaaaatt cggttaaggc cagggggaaa gaaaaaatat    660
aaattaaaac atatagtatg ggcaagcagg gagctagaac gattcgcagt taatcctggc    720
ctgttagaaa catcagaagg ctgtagacaa atactgggac agctacaacc atcccttcag    780
acaggatcag aagaacttag atcattatat aatacagtag caaccctcta ttgtgtgcat    840
caaaggatag agataaaaga caccaaggaa gctttagaca atagagga agagcaaaac    900
aaaagtaaga ccaccgcaca gcaagcggcc gctgatcttc agacctggag gaggagatat    960
gagggacaat tggagaagtg aattatataa atataaagta gtaaaattg aaccattagg   1020
agtagcaccc accaaggcaa agagaagagt ggtgcagaga gaaaaaagag cagtgggaat   1080
aggagctttg ttccttgggt tcttgggagc agcaggaagc actatgggcg cagcctcaat   1140
gacgctgacg gtacaggcca gacaattatt gtctggtata gtgcagcagc agaacaattt   1200
gctgagggct attgaggcgc aacagcatct gttgcaactc acagtctggg gcatcaagca   1260
gctccaggca agaatcctgg ctgtggaaag atacctaaag gatcaacagc tcctggggat   1320
ttggggttgc tctggaaaac tcatttgcac cactgctgtg ccttggaatg ctagttggag   1380
taataaatct ctggaacaga tttggaatca cacgacctgg atggagtggg acagagaaat   1440
taacaattac acaagcttaa tacactcctt aattgaagaa tcgcaaaacc agcaagaaaa   1500
gaatgaacaa gaattattgg aattagataa atgggcaagt ttgtggaatt ggtttaacat   1560
aacaaattgg ctgtggtata taaaattatt cataatgata gtaggaggct tggtaggttt   1620
aagaatagtt tttgctgtac tttctatagt gaatagagtt aggcagggat attcaccatt   1680
atcgtttcag acccacctcc caaccccgag gggacccgac aggcccgaag gaatagaaga   1740
agaaggtgga gagagagaca gagacagatc cattcgatta gtgaacggat ctcgacggta   1800
tcggttaact tttaaaagaa aagggggat tgggggtac agtgcagggg aaagaatagt   1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagg aacagagaaa caggagaata tgggccaaac aggatatctg tggtaagcag   2040
ttcctgcccc ggctcagggc caagaacagt tggaacagca gaatatgggc caaacaggat   2100
atctgtggta agcagttcct gccccggctc agggccaaga acagatgtc ccagatgcg   2160
gtcccgccct cagcagtttc tagagaacca tcagatgttt ccaggtgccc caaggacct   2220
gaaatgaccc tgtgccttat ttgaactaac caatcagttc gcttctcgct tctgttcgcg   2280
cgcttctgct ccccgagctc tatataagca gagctcgttt agtgaaccgt cagatccgcta   2340
gcaccggtgc cgccaccatg cctctggccc tgctgtggct gggcctggcc ctgctgggca   2400
ccctgcacgc ccaggccggc gtgcaggtgg agacaatctc cccaggcgac ggacgcacat   2460
tcctaagcg ggccagacc tgcgtggtgc actatacagg catgctggag gatgcaaga   2520
agtttgcag ctcccgggat agaaacaagc cattcaagtt tatgctgggc aagcaggaag   2580
tgatcagagg ctgggagggag gcgtggcc agatgtctgt gggccagagg gccaagctga   2640
```

```
ccatcagccc agactacgcc tatggagcaa caggccaccc aggaatcatc ccacctcacg    2700
ccaccctggt gttcgatgtg gagctgctga agctgggcga gggcggtagt cagaaccttg    2760
tgataccatg ggccccagaa aatctcacac ttcataaact ttccgaatca caactcgaac    2820
tcaactggaa taaccggttc ctgaatcact gtcttgaaca cctggtacaa tatcggaccg    2880
actggatca ctcatggaca gaacaatctg tggactatag gcacaaattc tcactcccaa    2940
gcgtagacgg ccaaaaaaga tacacttttc gcgtacgatc ccgctttaat cctctctgcg    3000
gctctgctca gcactggagt gaatggtccc atcccattca ttggggatcc aacacatcaa    3060
aagagaaccc ctttctgttc gcattggagg ccgtagtcat atctgttgga tccatgggac    3120
ttattatctc cctgttgtgt gtgtacttct ggctggaacg gactatgccc aggatcccca    3180
cgctcaagaa tctggaagat ctcgtcacag aataccatgg taatttcagc gcctggagcg    3240
gagtctctaa gggtctggcc gaatccctcc aacccgatta ttctgaacgg ttgtgcctcg    3300
tatccgaaat accaccaaaa ggcggggctc tgggtgaggg cccaggggcg agtccgtgca    3360
atcaacacag cccgtattgg gcccctcctt gttatacgtt gaagcccgaa actggaagcg    3420
gagctactaa cttcagcctg ctgaagcagg ctggagagaa cctggaccta    3480
tggcactgcc cgtgaccgcc ctgctgctgc ctctggccct gctgctgcac cagcccggc    3540
ctatcctgtg gcacgagatg tggcacgagg gcctggagga ggccagcagg ctgtattttg    3600
gcgagcgcaa cgtgaagggc atgttcgagg tgctggagcc tctgcacgcc atgatggaga    3660
gaggcccaca gaccctgaag gagacatcct ttaaccaggc ctatgacgg gacctgatgcg    3720
aggcacagga gtggtgcaga aagtacatga agtctggcaa tgtgaaggac ctgctgcagg    3780
cctgggatct gtactatcac gtgtttcgga gaatctccaa gggaggttca aaaccttttg    3840
agaaccttag actgatggcg cccatctctc tgcaggtagt tcacgttgag acccatagat    3900
gcaatataag ctgggaaatc tcacaagcca gccattactt tgaacggcat ttggaattcg    3960
aggcccgaac acttccccc ggtcatacgt gggaagaagc tcctctcttg acgctgaagc    4020
agaagcagga gtggatttgt ctggagactt tgactcctga tactcagtat gagttccaag    4080
ttcgggtgaa accactccaa ggcgagttca cgacgtggtc tccgtggagt caaccgttgg    4140
cgttccgcac gaagcccgcc gcccttggca aagacacgat tccgtggctt gggcatctgc    4200
tcgttgggct gagtggtgcg tttggtttca tcatcttggt ctatctcttg atcaattgca    4260
gaaatacagg cccttggctg aaaaaagtgc tcaagtgtaa taccccccgac ccaagcaagt    4320
tcttctccca gctttcttca gagcatggag gcgatgtgca gaaatggctc tcttcacctt    4380
ttccctctcc aagcttctcc ccgggagggc tggcgcccga gatttcacct cttgaggtac    4440
ttgaacgaga caaggttacc caacttctcc ttcaacagga taaggtaccc gaacctgcga    4500
gccttagctc caaccactct cttacgagct gcttcaccaa tcagggatac ttcttttcc    4560
accttcccga tgcgctggaa atcgaagctt gtcaagtttta cttttaccat gatccatata    4620
gcgaggaaga tcccgacgaa ggagtcgccg gtgcgcccac gggttcctca ccccaacctc    4680
tccagcctct ctcaggagaa gatgatgctt attgcactt tcccagtaga gacgatctcc    4740
tcctctttc tccatctctt ttgggggac cttccccccc ttctacggca cctggcgggt    4800
ctggtgctgg cgaggagcgg atgccgccgt ccctccagga gcgagtacca cgagattggg    4860
atccccagcc acttggaccc cccaccccg gcgtacctga ccttgtcgat tttcaacctc    4920
cccctgaatt ggtgctgcga gaggctgggg aggaagttcc gcagctgggg ccgagggagg    4980
gcgtgtcctt tccatggagt aggcctccag gtcaaggcga gtttagggct ctcaacgcgc    5040
ggctgccgtt gaatacagac gcttatctct cactgcagga actgcaaggt caggacccaa    5100
cacatcttgt aggatctggt gctactaatt tttctctttt gaagcaagct ggagatgttg    5160
aagagaccc tggtccagtg agcaagggcg aggagctgtt caccgggtg gtgcccatcc    5220
tggtcgagct ggacgcgac gtaaacggcc acaagttcag cgtgtccggc gagggcgagg    5280
gcgatgccac ctacggcaag ctgacccctga agttcatctg caccaccggc aagctgcccg    5340
tgccctggcc caccctcgtg accaccctga cctacggcgt gcagtgcttc agccgctacc    5400
ccgaccacat gaagcagcac gacttcttca agtccgccat gcccgaaggc tacgtccagg    5460
agcgcaccat cttcttcaag gacgacggca actacaagac ccgcgccgag gtgaagttcg    5520
agggcgacac cctggtgaac cgcatcgagc tgaagggcat cgacttcaag gaggacggca    5580
acatcctggg gcacaagctg gagtacaact acaacagcca caacgtctat atcatggccg    5640
acaagcagaa gaacggcatc aaggtgaact tcaagatccg ccacaacatc gaggacggca    5700
gcgtgcagct cgccgaccac taccagcaga cacccccat cggcgacggc cccgtgctgc    5760
tgcccgacaa ccactacctg agcacccagt ccgccctgag caaagacccc aacgagaagc    5820
gcgatcacat ggtcctgctg gagttcgtga ccgccgccgg gatcactctc ggcatggacg    5880
agctgtacaa gtaaactagt gtcgacaatc aacctctgga ttacaaaatt tgtgaaagat    5940
tgactggtat tcttaactat gttgctcctt ttacgctatg tggatacgct gctttaatgc    6000
ctttgtatca tgctattgct tcccgtatgg ctttcatttt ctcctccttg tataaatcct    6060
ggttgctgtc tctttatgag gagttgtggc ccgttgtcag gcaacgtggc gtggtgtgca    6120
ctgtgtttgc tgacgcaacc cccactggtt ggggcattgc caccacctgt cagctccttt    6180
ccgggacttt cgcttttccc ctccctattg ccacggcgga actcatcgcc gcctgccttg    6240
cccgctgctg gacaggggct cggctgttgg gcactgacaa ttccgtggtg ttgtcgggga    6300
agctgacgtc ctttccatgg ctgctcgcct gtgttgccac ctggattctg cgcgggacgt    6360
ccttctgcta cgtcccttcg gccctcaatc cagcggacct tccttcccgc ggcctgctgc    6420
cggctctgcg gcctcttccg cgtcttcgcc ttcgccctca gacgagtcgg atctccctt    6480
gggccgcctc cccgcctgga attcgagctc ggtacctta agaccaatga cttacaaggc    6540
agctgtagat cttagccact ttttaaaaga aaaggggga ctgaagggc taattcactc    6600
ccaacgaaga caagatctgc tttttgcttg tactgggtct ctctggttag accagatctg    6660
agcctgggag ctctctggct aactagggaa cccactgctt aagcctcaat aaagcttgcc    6720
ttgagtgctt caagtagtgt gtgcccgtct gttgtgtgac tctggtaact agagatcctc    6780
cagacccttt tagtcagtgt ggaaaatctc tagcagtagt agttcatgtc atcttattat    6840
tcagtattta taacttgcaa agaaatgaat atcagagagt gagaggaact tgtttattgc    6900
agcttataat ggttacaaat aaagcaatag catcacaaat ttcacaaata aagcatttt    6960
ttcactgcat tctagttgtg gtttgtccaa actcatcaat gtatcttatc atgtctggct    7020
ctagctatcc cgcccctaac tccgcccagt tccgcccatt ctccgcccca tggctgacta    7080
attttttta tttatgcaga ggccgaggcc gcctcggcct ctgagctatt ccagaagtag    7140
tgaggaggct tttttggagg cctaggcttt tgcgtcgaga cgtacccaat cgccctata    7200
gtgagtcgta ttacgcgcgc tcactggccg tcgttttaca acgtcgtgac tgggaaaacc    7260
ctggcgttac ccaacttaat cgccttgcag cacatcccc tttcgccagc tggcgtaata    7320
gcgaagaggc ccgcaccgat cgcccttccc aacagttgcg cagcctgaat ggcgaatggc    7380
```

```
gcgacgcgcc ctgtagcggc gcattaagcg cggcgggtgt ggtggttacg cgcagcgtga   7440
ccgctacact tgccagcgcc ctagcgcccg ctccttttcgc tttcttccct tcctttctcg   7500
ccacgttcgc cggctttccc cgtcaagctc taaatcgggg gctcccttta gggttccgat   7560
ttagtgcttt acggcacctc gaccccaaaa aacttgatta gggtgatggt tcacgtagtg   7620
ggcatcgcc ctgatagacg gttttttcgcc ctttgacgtt ggagtccacg ttctttaata   7680
gtggactctt gttccaaact ggaacaacac tcaaccctat ctcggtctat tcttttgatt   7740
tataagggat tttgccgatt tcggcctatt ggttaaaaaa tgagctgatt taacaaaaat   7800
ttaacgcgaa ttttaacaaa atattaacgt ttacaatttc ccaggtggca cttttcgggg   7860
aaatgtgcgc ggaacccctta tttgtttatt tttctaaata cattcaaata tgtatccgct   7920
catgagacaa taaccctgat aaatgcttca ataattattga aaaggaaga gtatgagtat   7980
tcaacatttc cgtgtcgccc ttattccctt ttttgcggca ttttgccttc ctgtttttgc   8040
tcacccagaa acgctggtga agtaaaaga tgctgaagat cagttgggtg cacgagtggg   8100
ttacatcgaa ctggatctca acagcggtaa gatcctgag agttttcgcc ccgaagaacg   8160
ttttccaatg atgagcactt ttaaagttct gctatgtggc gcggtattat cccgtattga   8220
cgccgggcaa gagcaactcg gtcgccgcat acactattct cagaatgact tggttgagta   8280
ctcaccagtc acagaaaagc atcttacgga tggcatgaca gtaagagaat tatgcagtgc   8340
tgccataacc atgagtgata acactgcggc caacttactt ctgacaacga tcggaggacc   8400
gaaggagcta accgcttttt tgcacaacat ggggggatcat gtaactcgcc ttgatcgttg   8460
ggaaccggag ctgaatgaag ccataccaaa cgacgagcgt gacaccacga tgcctgtagc   8520
aatggcaaca acgttgcgca aactattaac tggcgaacta cttactctag cttcccggca   8580
acaattaata gactggatgg aggcggataa agttgcagga ccacttctgc gctcggccct   8640
tccggctggc tggtttattg ctgataaatc tggagccggt gagcgtgggt ctcgcggtat   8700
cattgcagca ctggggccag atggtaagcc ctcccgtatc gtagttatct acacgacggg   8760
gagtcaggca actatggatg aacgaaatag acagatcgct gagataggtg cctcactgat   8820
taagcattgg taactgtcag accaagttta ctcatatata ctttagattg atttaaaact   8880
tcatttttaa tttaaaagga tctaggtgaa gatcctttttt gataatctca tgaccaaaat   8940
cccttaacgt gagttttcgt tccactgagc gtcagacccc gtagaaaaga tcaaaggatc   9000
ttcttgagat cctttttttc tgcgcgtaat ctgctgcttg caaacaaaaa aaccaccgct   9060
accagcggtg gtttgtttgc cggatcaaga gctaccaact cttttttccga aggtaactgg   9120
cttcagcaga gcgcagatac caaatactgt ccttctagtg tagccgtagt taggccacca   9180
cttcaagaac tctgtagcac cgcctacata cctcgctctg ctaatcctgt taccagtgg   9240
tgctgccagt ggcgataagt cgtgtcttac cgggttggac tcaagacgat agttaccgga   9300
taaggcgcag cggtcgggct gaacggggggg ttcgtgcaca cagcccagct tggagcgaac   9360
gacctacacc gaactgagat acctacagcg tgagctatga gaaagcgcca cgcttcccga   9420
agggagaaag gcggacaggt atccggtaag cggcagggtc ggaacaggag agcgcacgag   9480
ggagcttcca gggggaaacg cctggtatct ttatagtcct gtcgggtttc gccacctctg   9540
acttgagcgt cgatttttgt gatgctcgtc agggggggcgg agcctatgga aaaacgccag   9600
caacgcggcc ttttttacggt tcctggcctt ttgctggcct tttgctcaca tgttctttcc   9660
tgcgttatcc cctgattctg tggataaccg tattaccgcc tttgagtgag ctgataccgc   9720
tcgccgcagc cgaacgaccg agcgcagcga gtcagtgagc gaggaagcgg aagagcgccc   9780
aatacgcaaa ccgcctctcc ccgcgcgttg gccgattcat taatgcagct ggcacgacag   9840
gtttcccgac tggaaagcgg gcagtgagcg caacgcaatt aatgtgagtt agctcactca   9900
ttaggcaccc caggctttac actttatgct tccggctcgt atgttgtgtg gaattgtgag   9960
cggataacaa tttcacacag gaaacagcta tgaccatgat tacgccaagc gcgcaattaa  10020
ccctcactaa agggaacaaa agctggagct gca                              10053

SEQ ID NO: 20           moltype = DNA   length = 9405
FEATURE                 Location/Qualifiers
misc_feature            1..9405
                        note = IL2Rg upstream of IL2Rb
source                  1..9405
                        mol_type = other DNA
                        organism = synthetic construct
SEQUENCE: 20
agcttaatgt agtcttatgc aatactcttg tagtcttgca acatggtaac gatgagttag     60
caacatgcct tacaaggaga gaaaagcac cgtgcatgcc gattggtgga agtaaggtgg    120
tacgatcgtg cctattagg aaggcaacag acgggtctga catggattgg acgaaccact    180
gaattgccgc attgcagaga tattgtattt aagtgcctag ctcgatacaa taaacgggtc    240
tctctggtta gaccagatct gagcctggga gctctctggc taactaggga acccactgtt    300
taagcctcaa taaagcttgc cttgagtgct tcaagtagtg tgtgcccgtc tgttgtgtga    360
ctctggtaac tagagatccc tcagaccctt ttagtcagtg tggaaaatct ctagcagtgg    420
cgcccgaaca gggacttgaa agcgaaaggg aaaccagagg agctctctcg acgcaggact    480
cggcttgctg aagcgcgcac ggcaagaggc gaggggcggc gactggtgag tacgccaaaa    540
attttgacta gcggaggcta aaggagaga gatgggtgcg agagcgtcag tattaagcgg    600
gggagaatta gatcgcgatg ggaaaaaatt cggttaagcc agggggggaaa gaaaaaatat    660
aaattaaaac atatagtatg ggcaagcagg gagctagaac gattcgcagt taatcctggc    720
ctgttagaaa catcagaagg ctgtagacaa atactggaca agctacaacc atcccttcag    780
acaggatcag aagaacttag atcattatat aatacagtaa caaccctcta ttgtgtgcat    840
caaaggatag agataaaaga caccaaggaa gctttagaca agatagagga agagcaaaac    900
aaaagtaaga ccaccgcaca gcaagcggcc gctgatcttc agacctggag gaggagatat    960
gagggacaat tggagaagtg aattatataa atataaagta gtaaaattg aaccattagg   1020
agtagcaccc accaaggcaa agagaagagt ggtgcagaga gaaaaaagag cagtgggaat   1080
aggagctttg ttccttgggt tcttgggagc agcaggaagc actatgggcg cagcctcaat   1140
gacgctgacg gtacaggcca gacaattatt gtctggtata gtgcagcagc agaacaattt   1200
gctgagggct attgaggcgc aacagcatct gttgcaactc acagtctggg gcatcaagca   1260
gctccaggca agaatcctgg ctgtggaaag atacctaaag gatcaacagc tcctggggat   1320
ttggggttgc tctggaaaac tcatttgcac cactgctgtg ccttggaatg ctagttggag   1380
taataaatct ctggaacaga tttggaatca cacgacctgg atggagtggg acagagaaat   1440
taacaattac acaagcttaa tacactcctt aattgaagaa tcgcaaaacc agcaagaaaa   1500
```

```
gaatgaacaa gaattattgg aattagataa atgggcaagt ttgtggaatt ggtttaacat   1560
aacaaattgg ctgtggtata taaaattatt cataatgata gtaggaggct tggtaggttt   1620
aagaatagtt tttgctgtac tttctatagt gaatagagtt aggcaggat attcaccatt   1680
atcgtttcag acccacctcc caaccccgag ggaccagac aggcccgaag gaatagaaga   1740
agaaggtgga gagagagaca gagacagatc cattcgatta gtgaacggat ctcgacggta   1800
tcggttaact tttaaaagaa aagggggat tgggggtac agtgcagggg aaagaatagt   1860
agacataata gcaacagaca tacaaactaa agaattacaa aaacaaatta caaaaattca   1920
aaattttatc gatcacgaga ctagcctcga gaagcttgat atcgaattcc cacggggttg   1980
gacgcgtagg aacagagaaa caggagaata tgggccaaag aggatatctg tggtaagcag   2040
ttcctgcccc ggctcagggc caagaacagt tggaacagca gaatatgggc caaacaggat   2100
atctgtggta agcagttcct gcccccggctc agggccaaga acagatggtc cccagatgcg   2160
gtcccgccct cagcagtttc tagagaacca tcagatgttt ccagggtgcc caaggacct    2220
gaaatgaccc tgtgccttat ttgaactaac caatcagttc gcttctcgct tctgttcgcg   2280
cgcttctgct ccccgagctc tatataagca gagctcgttt agtgaaccgt cagatcgcta   2340
gcaccggtgc cgccaccatg cctctggccc tgctgtggcc gggcctggcc ctgctgggcg   2400
ccctgcacgc ccaggccggc gtgcaggtgg agacaatctc cccaggcgac ggacgcacat   2460
tccctaagcg gggccagacc tgcgtggtgc actatacagg catgctggag gatggcaaga   2520
agtttgacag ctcccgggat agaaacaagc cattcaagtt tatgctgggc aagcaggaag   2580
tgatcagagg ctgggaggag ggcgtggccc agatgtctgt gggccagagg gccaagctga   2640
ccatcagccc agactacgcc tatggagcaa caggccaccc aggaatcatc ccacctcacg   2700
ccaccctggt gttcgatgtg gagctgctga agctgggcga gggatccaac acatcaaaag   2760
agaaccccctt tctgttcgca ttggaaggccg tagtcatatc tgttggatcc atgggactta   2820
ttatctccct gttgtgtgtg tacttctggc tggaacggaa tatgcccagg atccccacgc   2880
tcaagaatct ggaagatctc gtcacagaat accatggtaa tttcagcgcc tggagcggag   2940
tctctaaggg tctggccgaa tccctccaac ccgattattc tgaacggttg tgcctcgtat   3000
ccgaaatacc accaaaaggc ggggctctgg tgagggccga gtgaggccgt ccgtgcaatc   3060
aacacagccc gtattgggcc cctccttgtt atacgttgaa gcccgaaact ggaagcggag   3120
ctactaactt cagcctgctg aagcaggctg gagacgtgga ggagaaccct ggacctatgg   3180
cactgccccgt gaccgccctg ctgctgcctc tggccctgct gctgcacgca gcccggccta   3240
tcctgtggca cgagatgtgg cacgagggcc tggagggagc cagcagggtg tattttgggg   3300
agcgcaacgt gaagggcatg ttcgaggtgc tggagcctct gcacgccatg atggagagag   3360
gcccacagac cctgaaggag acatcctta accaggccta tggacgggac ctgatggagg   3420
cacaggagtg gtgcagaaag tacatgaagt ctggcaatgt gaaggacctg ctgcaggcct   3480
gggatctgta ctatcacgtg tttcggagaa tctccaaggg caaagacacag attccgtggc   3540
ttgggcatct gctcgttggg ctgagtggtg cgtttggttt catcatcctg gtctatctct   3600
tgatcaattg cagaaataca ggcccttggc tgaaaaaagt gctcaagtgt aatacccccg   3660
acccaagcaa gttcttctcc cagctttctt cagagcatgg aggcgatgtg cagaaatggc   3720
tctcttcacc ttttccctcc tcaagcttct ccccgggagg gctggcgccc gagatttcac   3780
ctcttgaggt acttgaacga gacaaggtta cccaacttct ccttcaacag gataaggtac   3840
ccgaacctgc gagccttagc tccaaccact ctcttacgag ctgcttcacc aatcagggat   3900
acttcttttt ccaccttccc gatgcgctgg aaatcgaagc ttgtcaagtt tactttacct   3960
atgatccata tagcgaggaa gatcccgacg aaggagtcgc cggtgcgccc acgggttcct   4020
caccccaacc tctccaggag aagtgatgc ttattgcact tttcccagta   4080
gagacgatct cctcctcttt tctccatctc ttttgggggg accttcccccc ccttctacgg   4140
cacctggcgg gtctggtgct ggcgaggagc ggatgccgcc gtcctccag gagcgagtac   4200
cacgagattg ggatccccag ccacttggac cccccacccc cggcgtacct gaccttgtcg   4260
attttcaacc tccccctgaa ttggtgctgc gagaggctgg ggaggaagtt ccggacgctg   4320
ggccgaggga gggcgtgtcc tttcatgga gtaggcctcc aggtcaaggc gagtttaggg   4380
ctctcaacgc cgcgctgccg ttgaatacag acgcttatct ctcactgcag gaactgcaag   4440
gtcaggaccc aacacatctt gtaggatctg gtgctactaa ttttttctctt ttgaagcaag   4500
ctggagatgt tgaagagaac cctggtccag tgagcaaggg cgaggagctg ttcaccgggg   4560
tggtgcccat cctggtcgag ctggacggcg acgtaaacgg ccacaagttc agcgtgtccg   4620
gcgagggcga gggcgatgcc acctacggca agctgaccct gaagttcatc tgcaccaccg   4680
gcaagctgcc cgtgccctgg cccaccctcg tgaccaccct gacctacggc gtgcagtgct   4740
tcagccgcta ccccgaccac atgaagcagc acgacttctt caagtccgcc atgcccgaag   4800
gctacgtcca ggagcgcacc atcttcttca aggacgacgg caactacaag acccgcgccc   4860
aggtgaagtt cgagggcgac accctggtga accgcatcga gctgaagggc atcgacttca   4920
aggaggacgg caacatcctg ggcacaagc tggagtacaa ctacaacagc cacaacgtct   4980
atatcatggc cgacaagcag aagaacggca tcaaggtgaa cttcaagatc cgccacaaca   5040
tcgaggacgg cagcgtgcag ctcgccgacc actaccagca gaacaccccc atcggcgacg   5100
gccccgtgct gctgcccgac aaccactacc tgagcaccca gtccgccctg agcaaagacc   5160
ccaacgagaa gcgcgatcac atggtcctgc tggagttcgt gaccgccgcc gggatcactc   5220
tcggcatgga cgagctgtac aagtaaacta gtgtcgacaa tcaacctctg gattacaaaa   5280
tttgtgaaag attgactggt attcttaact atgttgctcc ttttacgcta tgtggatacg   5340
ctgctttaat gcctttgtat catgctattg cttcccgtat ggctttcatt ttctcctcct   5400
tgtataaatc ctggttgctg tctctttatg aggagttgtg gcccgttgtc aggcaacgtg   5460
gcgtggtgtg cactgtgttt gctgacgcaa ccccactggt tggggcatt gccaccacct   5520
gtcagctcct ttccgggact ttcgctttcc cctccccctat tgccacgcgc gaactcatcg   5580
ccgcctgcct tgcccgctgc tggacagggg ctcggctgtt gggcactgac aattccgtgg   5640
tgttgtcggg gaagctgacg tccttttccat ggctgctcgc ctgtgttgcc acctggattc   5700
tgcgcgggac gtccttctgc tacgtcccctt cggccctcaa tccagcggac cttccttccc   5760
gcggcctgct gccggtctg cggcctcttc cgcgtcttcg ccttcgccct cagacgagtc   5820
ggatctcccct ttgggccgcc tccccgcctg gaattcgagc tcggtacctt taagaccaat   5880
gacttacaag gcagctgtag atcttagcca ctttttaaaa gaaaaggggg gactggaagg   5940
gctaattcac tcccaacgaa gacaagatct gcttttttgct tgtactgggt ctctctggtt   6000
agaccagatc tgagcctggg agctctctgg ctaactaggg aacccactgc ttaagcctca   6060
ataaagcttg ccttgagtgc ttcaagtagt gtgtgcccgt ctgttgtgtg actctggtaa   6120
ctagagatcc ctcagaccct tttagtcagt gtggaaaatc tctagcagta gtagttcatg   6180
tcatcttatt attcagtatt tataacttgc aaagaaatga atatcagaga gtgagaggaa   6240
```

```
cttgtttatt gcagcttata atggttacaa ataaagcaat agcatcacaa atttcacaaa   6300
taaagcattt ttttcactgc attctagttg tggtttgtcc aaactcatca atgtatctta   6360
tcatgtctgg ctctagctat cccgcccta actccgccca gttccgccca ttctccgccc    6420
catggctgac taatttttt tatttatgca gaggccgagg ccgcctcggc ctctgagcta    6480
ttccagaagt agtgaggagg cttttttgga ggcctaggct tttgcgtcga gacgtaccca   6540
attcgcccta tagtgagtcg tattacgcgc gctcactggc cgtcgtttta caacgtcgtg   6600
actgggaaaa ccctggcgtt acccaactta atcgccttgc agcacatccc cctttcgcca   6660
gctggcgtaa tagcgaagag gcccgcaccg atcgcccttc ccaacagttg cgcagcctga   6720
atggcgaatg gcgcgacgcg ccctgtagcg gcgcattaag cgcggcgggt gtggtggtta   6780
cgcgcagcgt gaccgctaca cttgccagcg ccctagcgcc cgctcctttc gctttcttcc   6840
cttcctttct cgccacgttc gccggctttc cccgtcaagc tctaaatcgg gggctccctt   6900
tagggttccg atttagtgct ttacggcacc tcgaccccaa aaaacttgat tagggtgatg   6960
gttcacgtag tgggccatcg ccctgataga cggtttttcg ccctttgacg ttggagtcca   7020
cgttctttaa tagtggactc ttgttccaaa ctggaacaac actcaaccct atctcggtct   7080
attctttttga tttataaggg attttgccga tttcggccta ttggttaaaa aatgagctga   7140
tttaacaaaa atttaacgcg aattttaaca aaatattaac gtttacaatt tcccaggtgg   7200
cacttttcgg ggaaatgtgc gcggaacccc tatttgttta tttttctaaa tacattcaaa   7260
tatgtatccg ctcatgagac aataaccctg ataaatgctt caataatatt gaaaaaggaa   7320
gagtatgagt attcaacatt tccgtgtcgc ccttattccc tttttgcgg cattttgcct    7380
tcctgttttt gctcacccag aaacgctggt gaaagtaaaa gatgctgaag atcagttggg   7440
tgcacgagtg ggttacatcg aactggatct caacagcggt aagatccttg agagttttcg   7500
ccccgaagaa cgttttccaa tgatgagcac ttttaaagtt ctgctatgtg gcgcggtatt   7560
atcccgtatt gacgccgggc aagagcaact cggtcgccgc atacactatt ctcagaatga   7620
cttggttgag tactcaccag tcacagaaaa gcatcttacg gatggcatga cagtaagaga   7680
attatgcagt gctgccataa ccatgagtga taacactgcg gccaacttac ttctgacaac   7740
gatcggagga ccgaaggagc taaccgcttt tttgcacaac atgggggatc atgtaactcg   7800
ccttgatcgt tgggaaccgg agctgaatga agccatacca aacgacgagc gtgacaccac   7860
gatgcctgta gcaatggcaa caacgttgcg caaactatta actggcgaac tacttactct   7920
agcttcccgg caacaattaa tagactggat ggaggcggat aaagttgcag gaccacttct   7980
gcgctcggcc cttccggctg gctggtttat tgctgataaa tctggagccg gtgagcgtgg   8040
gtctcgcggt atcattgcag cactggggcc agatggtaag ccctcccgta tcgtagttat   8100
ctacacgacg gggagtcagg caactatgga tgaacgaaat agacagatcg ctgagatagg   8160
tgcctcactg attaagcatt ggtaactgtc agaccaagtt tactcatata ctttagat     8220
tgatttaaaa cttcatttt aatttaaaag gatctaggtg aagatccttt ttgataatct    8280
catgaccaaa atcccttaac gtgagttttc gttccactga gcgtcagacc ccgtagaaaa   8340
gatcaaagga tcttcttgag atcctttttt tctgcgcgta atctgctgct tgcaaacaaa   8400
aaaaccaccg ctaccagcgg tggtttgttt gccggatcaa gagctaccaa ctctttttcc   8460
gaaggtaact ggcttcagca gagcgcagat accaaatact gtccttctag tgtagccgta   8520
gttaggccac cacttcaaga actctgtagc accgcctaca tacctcgctc tgctaatcct   8580
gttaccagtg gctgctgcca gtggcgataa gtcgtgtctt accgggttgg actcaagacg   8640
atagttaccg gataaggcgc agcggtcggg ctgaacgggg ggttcgtgca cacagcccag   8700
cttggagcga acgacctaca ccgaactgag atacctacag cgtgagctat gagaaagcgc   8760
cacgcttccc gaagggagaa aggcggacag gtatccggta agcggcaggg tcggaacagg   8820
agagcgcacg agggagcttc caggggggaaa cgcctggtat ctttatagtc ctgtcggttt   8880
tcgccacctc tgacttgagc gtcgatttt gtgatgctcg tcagggggc ggagcctatg     8940
gaaaaacgcc agcaacgcgg cctttttacg gttcctggcc ttttgctggc cttttgctca   9000
catgttcttt cctgcgttat ccctgattc tgtggataac cgtattaccg cctttgagtg   9060
agctgatacc gctcgccgca gccgaacgac cgagcgcagc gagtcagtga gcgaggaagc   9120
ggaagagcgc ccaatacgca aaccgcctct ccccgcgcgt tggccgattc attaatgcag   9180
ctggcacgac aggtttcccg actggaaagc gggcagtgag cgcaacgcaa ttaatgtgag   9240
ttagctcact cattaggcac cccaggcttt acactttatg cttccggctc gtatgttgtg   9300
tggaattgtg agcggataac aatttcacac aggaaacagc tatgaccatg attacgccaa   9360
gcgcgcaatt aaccctcact aaagggaaca aaagctggag ctgca                   9405
```

METHODS OF EXOGENOUS DRUG ACTIVATION OF CHEMICAL-INDUCED SIGNALING COMPLEXES EXPRESSED IN ENGINEERED CELLS IN VITRO AND IN VIVO

INCORPORATION BY REFERENCE TO A PRIORITY APPLICATION

This application is a continuation of U.S. application Ser. No. 16/467,013 filed Jun. 5, 2019 which is the U.S. National Phase Application of PCT App. No. PCT/US2017/065746, filed on Dec. 12, 2017, designating the United States of America and published in the English language, which claims priority to U.S. Prov. App. No. 62/433,540, filed on Dec. 13, 2016. The disclosures of the above-referenced applications are hereby expressly incorporated by reference in their entireties.

REFERENCE TO SEQUENCE LISTING

The present application is being filed along with a Sequence Listing in electronic format. The Sequence Listing is provided as a file entitled SCRI130C1SEQ, created Aug. 2, 2023, which is approximately 59,595 bytes in size. The information is the electronic format of the Sequence Listing and is hereby expressly incorporated by reference in its entirety.

FIELD

The present disclosure relates to compositions and methods for synthetic chemical-induced signaling. In particular, the compositions include a general architecture for generating physiologically functional synthetic chemical-induced signaling complexes, as well as, functional chemical-induced signaling complexes. Some embodiments provide a chemical-induced signaling complex that includes a multi-component protein, in which two components, normally existing as monomers, are brought together in the presence of a ligand to generate an active signaling complex, which activates signaling pathways in the cytoplasm of the cell. Further provided are methods of using such compositions for activating a cellular signaling pathway in a cell. Also provided are methods of using the compositions for selectively expanding a population of cells.

BACKGROUND

Chimeric antigen receptors (CARs) are engineered receptors used to genetically engineer T cells for use in adoptive cellular immunotherapy (see Pule et al., *Cytother.* 5:3, 2003; Restifo et al., *Nat. Rev. Immunol.* 12:269, 2012). Antigen binding stimulates the signaling domains on the intracellular segment of the CAR, thereby activating signaling pathways. CAR-based adoptive cellular immunotherapy has been used to treat cancer patients with tumors refractory to conventional standard-of-care treatments (see Grupp et al., *N. Engl. J. Med.* 368:1509, 2013; Kalos et al., *Sci. Transl. Med.* 3:95ra73, 2011).

Cells have various receptors on their surface for responding to extracellular signals that involve intercellular communication. Signal transduction of receptors has been studied extensively and receptors are involved in numerous signaling pathways. There remains a need for new compositions and methods that allow for one to transduce a desired signal through a synthetic complex that cannot be activated through a normal physiological pathway, thus providing a mechanism for activating signaling only within in a desired and specifically engineered population of cells.

SUMMARY

A dimerization activated receptor initiation complex (DARIC) has been developed, which provides a binding component and a signaling component that are each expressed as separate fusion proteins but contain an extracellular multimerization mechanism (bridging factor) for recoupling of the two functional components on a cell surface (see U.S. Pat. Appl. No. 2016/0311901, hereby expressly incorporated by reference in its entirety). Importantly, the bridging factor in the DARIC system forms a heterodimeric receptor complex, which does not produce significant signaling on its own. The described DARIC complexes only initiate physiologically relevant signals following further co-localization with other DARIC complexes. Thus, they do not allow for the selective expansion of desired cell types without a mechanism for further multimerization of DARIC complexes (such as by e.g., contact with a tumor cell that expresses a ligand bound by a binding domain incorporated into one of the DARIC components).

Accordingly, several aspects described herein relate to compositions and methods including a chemical-induced signaling complex (CISC). In some aspects, the compositions and methods may be used for the selective expansion of a desired population of cells.

Some embodiments described herein relate to a protein sequence encoding a chemical-induced signaling complex (CISC). In some embodiments, the protein sequence comprises a first sequence, wherein the first sequence encodes a first CISC component. In some embodiments, the first CISC component comprises a first extracellular binding domain or a portion thereof, a hinge domain, a transmembrane domain, and a signaling domain or a portion thereof. In some embodiments, the protein sequence comprises a second sequence. In some embodiments, the second sequence encodes a second CISC component. In some embodiments, the second CISC component comprises a second extracellular binding domain or portion thereof, a hinge domain, a transmembrane domain, and a signaling domain or portion thereof. In some embodiments, the first CISC component and the second CISC component are positioned such that when expressed, they dimerize in the presence of a ligand. In some embodiments, the first and second CISC components dimerize to form a heterodimer or a homodimer. In some embodiments, the dimeric CISC is a synthetic CISC. In some embodiments, the first and second extracellular domains are N-terminal to the transmembrane domain. In some embodiments, the first extracellular binding domain or a portion thereof comprises an FK506 binding protein (FKBP) domain. In some embodiments, the second extracellular binding domain or portion thereof comprises an FKBP rapamycin binding (FRB) domain or a portion thereof.

In some embodiments, the transmembrane domain of the first and second CISC components comprises a natural transmembrane domain. In some embodiments, the transmembrane domain of the first and second CISC components comprises an IL-2 receptor transmembrane domain. In some embodiments, the signaling domain or a portion thereof of the first and second CISC components comprises one or more concatenated cytoplasmic signaling domains. In some embodiments, the signaling domain or a portion thereof of the first and second CISC components comprises a cytokine signaling domain or an antigen receptor signaling domain. In some embodiments, the signaling domain of the first CISC component comprises an interleukin-2 receptor subunit gamma (IL2Rg) domain. In some embodiments, the signaling domain of the second CISC component comprises an interleukin-2 receptor subunit beta (IL2Rb) domain.

In some embodiments, one of the extracellular binding domains comprises an FKBP domain and the other extracellular binding domain comprises an FRB domain. In some embodiments, the extracellular binding domains are configured to simultaneously bind to a ligand.

In some embodiments, one extracellular binding domain comprises a cereblon thalidomide binding domain and the other extracellular binding domain comprises a domain that interacts with the cereblon thalidomide binding domain when it is bound to an IMID-class drug (e.g. thalidomide, pomalidomide, lenalidomide or related analogues). In some embodiments, the extracellular binding domains are configured to simultaneously bind to the IMID ligand.

In some embodiments, one of the extracellular binding domain comprises one member of a heterodimerizing protein domain pair, and the other extracellular binding domain comprises the other component of a heterodimerization domain pair, and the domains are configured to bind to a ligand e.g., by simultaneous binding.

In some embodiments, the ligand is an antibody or a portion thereof, such as a binding fragment, a protein, a small molecule, or a drug. In some embodiments, the ligand is rapamycin or a rapalog, such as everolimus, CCI-779, C20-methallylrapamycin, C16-(S)-3-methylindolerapamycin, C16-iRap, AP21967, sodium mycophenolic acid, benidipine hydrochloride, AP23573, AP1903, or metabolites, derivatives, and/or combinations thereof. In some embodiments, the ligand is an IMID-class drug (e.g. thalidomide, pomalidomide, lenalidomide or related analogues). In some embodiments, the ligand is present or provided in an amount from 0.05 nM to 100 nM such as e.g., 0.05 nM, 0.1 nM, 0.5, nM, 1.0 nM, 5.0 nM, 10.0 nM, 15.0 nM, 20.0 nM, 25.0 nM, 30.0 nM, 35.0 nM, 40.0 nM, 45.0 nM, 50.0 nM, 55.0 nM, 60.0 nM, 65.0 nM, 70.0 nM, 75.0 nM, 80.0 nM, 90.0 nM, 95.0 nM, or 100 nM or an amount that is within a range defined by any two of the aforementioned amounts.

In some embodiments, the first sequence comprises an amino acid sequence set forth in SEQ ID NO: 1. In some embodiments, the first sequence comprises an amino acid sequence set forth in SEQ ID NO: 3, 5, or 7. In some embodiments, the second sequence comprises an amino acid sequence set forth in SEQ ID NO: 2. In some embodiments, the second sequence comprises an amino acid sequence set forth in SEQ ID NO: 4, 6, 8, or 9. Some embodiments concern nucleic acids encoding the amino acid sequences of SEQ ID NOs: 1, 2, 3, 4, 5, 6, 7, 8 and 9.

Some embodiments provided herein relate to an expression vector. In some embodiments, the expression vector comprises a nucleic acid encoding a protein sequence encoding a dimeric chemical-induced signaling complex (CISC). In some embodiments, the expression vector comprises a nucleic acid encoding a protein sequence comprising a first protein sequence, wherein the first protein sequence encodes a first CISC component. In some embodiments, the nucleic acid encoding the first sequence comprises a sequence encoding a first extracellular binding domain or a portion thereof, a hinge domain, a transmembrane domain, and a signaling domain or portions thereof. In some embodiments, the expression vector comprises a nucleic acid encoding a protein sequence comprising a second protein sequence, wherein the second protein sequence encodes a second CISC component. In some embodiments, the nucleic acid encoding the second sequence comprises a sequence encoding a second extracellular binding domain or a portion thereof, a hinge domain, a transmembrane domain, and a signaling domain or portions thereof. In some embodiments, the expression vector comprises a nucleic acid encoding the first protein sequence or the second protein sequence. In some embodiments, the expression vector comprises nucleic acid encoding the first sequence and the second protein sequence. In some embodiments, the vector is RNA or DNA. In some embodiments, the vector is a lentiviral vector or an adeno-associated viral (AAV) vector. In some embodiments, the expression vector is a nucleic acid sequence set forth in SEQ ID NO: 6, SEQ ID NO: 7, or SEQ ID NO: 8.

In some embodiments, the expression vector comprises a nucleic acid sequence that further comprises a promoter. In some embodiments, the promoter is an inducible promoter or a constitutive promoter.

Some embodiments provided herein relate to a cell, such as a mammalian cell, for chemical-induced signaling complex expression. In some embodiments, the cell, such as a mammalian cell, comprises a protein sequence as described herein or an expression vector described herein. Thus, in some embodiments, the cell, such as a mammalian cell, comprises a protein sequence encoding the components of a chemical-induced signaling complex (CISC). In some embodiments, the protein sequence comprises a first sequence, wherein the first sequence encodes a first component of a CISC. In some embodiments, the first component of a CISC comprises a first extracellular binding domain or portion thereof, a hinge domain, a transmembrane domain, and a signaling domain or portions thereof. In some embodiments, the protein sequence comprises a second sequence. In some embodiments, the second sequence encodes a second component of a CISC. In some embodiments, the second CISC component comprises a second extracellular binding domain or a portion thereof, a hinge domain, a transmembrane domain, and a signaling domain or portions thereof. In some embodiments, the cell, such as a mammalian cell, comprises an expression vector comprising a nucleic acid encoding a protein sequence encoding a component of a CISC. In some embodiments, the expression vector comprises a nucleic acid encoding a protein sequence comprising a first protein sequence, wherein the first protein sequence encodes a first component of a CISC. In some embodiments, the nucleic acid encoding the first sequence comprises a sequence encoding a first extracellular binding domain or a portion thereof, a hinge domain, a transmembrane domain, and a signaling domain or portions thereof. In some embodiments, the expression vector comprises a nucleic acid encoding a protein sequence comprising a second protein sequence, wherein the second protein sequence encodes a second component of a CISC. In some embodiments, the nucleic acid encoding the second sequence comprises a sequence encoding a second extracellular binding domain or a portion thereof, a hinge domain, a transmembrane domain, and a signaling domain or portions thereof. In some embodiments, the expression vector comprises a nucleic acid encoding the first protein sequence or the second protein sequence. In some embodiments, the expression vector comprises nucleic acid encoding the first sequence and the second protein sequence. In some embodiments, the vector is RNA or DNA. In some embodiments, the vector is a lentiviral vector or an adeno-associated viral (AAV) vector.

In some embodiments, the cell, such as a mammalian cell, is a precursor T cell or a T regulatory cell. In some embodiments, the cell, such as a mammalian cell, is a hematopoietic stem cell. In some embodiments, the cell is a CD34+, CD8+, or a CD4+ cell. In some embodiments, the cell is a CD8+ T cytotoxic lymphocyte cell selected from the group consisting of naïve CD8+ T cells, central memory CD8+ T cells, effector memory CD8+ T cells, and bulk CD8+ T cells or any combination thereof. In some embodiments, the cell is a CD4+ T helper lymphocyte cell selected from the group consisting of naïve CD4+ T cells, central memory CD4+ T cells, effector memory CD4+ T cells, and bulk CD4+ T cells or any combination thereof.

Some embodiments provided herein relate to a method of activating a signal into the interior of a cell, such as a mammalian cell, In some embodiments, the method comprises providing a cell, such as a mammalian cell, as described herein, expressing the protein sequence encoding the components of the synthetic CISC as described herein, or expressing the expression vector as described herein in the cell, and contacting the cell with a ligand, thereby causing the first and second CISC components to dimerize, which transduces a signal into the interior of the cell.

Accordingly, in some embodiments, the method of activating a signal into an interior of a cell, such as a mammalian cell, comprises providing a cell, such as a mammalian cell, that comprises one or more protein sequences encoding components of a CISC. In some embodiments, the protein sequence comprises a first sequence, wherein the first sequence encodes a first component of a CISC. In some embodiments, the first component of a CISC comprises a first extracellular binding domain or a portion thereof, a hinge domain, a transmembrane domain, and a signaling domain or portions thereof. In some embodiments, the protein sequence comprises a second sequence. In some embodiments, the second sequence encodes a second component of a CISC. In some embodiments, the second component of a CISC comprises a second extracellular binding domain or a portion thereof, a hinge domain, a transmembrane domain, and a signaling domain or portions thereof. In some embodiments, the method of activating a signal into an interior of a cell, such as a mammalian cell, comprises providing a cell, such as a mammalian cell, that comprises an expression vector comprising a nucleic acid encoding a protein sequence encoding a dimeric CISC. In some embodiments, the expression vector comprises a nucleic acid encoding a protein sequence comprising a first protein sequence, wherein the first protein sequence encodes a first component of a CISC. In some embodiments, the nucleic acid encoding the first sequence comprises a sequence encoding a first extracellular binding domain or a portion thereof, a hinge domain, a transmembrane domain, and a signaling domain or portions thereof. In some embodiments, the expression vector comprises a nucleic acid encoding a protein sequence comprising a second protein sequence, wherein the second protein sequence encodes a second component of a CISC. In some embodiments, the nucleic acid encoding the second sequence comprises a sequence encoding a second extracellular binding domain or a portion thereof, a hinge domain, a transmembrane domain, and a signaling domain or portions thereof. In some embodiments, the expression vector comprises a nucleic acid encoding the first protein sequence or the second protein sequence. In some embodiments, the expression vector comprises nucleic acid encoding the first sequence and the second protein sequence. In some embodiments, the vector is RNA or DNA. In some embodiments, the vector is a lentiviral vector or an adeno-associated viral (AAV) vector. In some embodiments, whether the cell, such as a mammalian cell, comprises the protein sequence or the expression vector, the method further comprises expressing the protein sequence encoding a heterodimeric CISC, or expressing the expression vector, and contacting the cell with a ligand, thereby causing the first and second components of a CISC to dimerize, which transduces a signal into the interior of the cell.

In some embodiments, the ligand comprises an antibody or a binding portion thereof, a protein, a small molecule, or a drug. In some embodiments, the ligand is rapamycin or a rapalog, such as everolimus, CCI-779, C20-methallylrapamycin, C16-(S)-3-methylindolerapamycin, C16-iRap, AP21967, sodium mycophenolic acid, benidipine hydrochloride, AP23573, or AP1903, or metabolites, derivatives, and/or combinations thereof. In some embodiments, the ligand is an immunomodulatory imide drug (IMID)-class drug (e.g. thalidomide, pomalidomide, lenalidomide or related analogues). In some embodiments, the ligand is present or provided in an amount of 0.05 nM to 100 nM such as e.g., 0.05 nM, 0.1 nM, 0.5, nM, 1.0 nM, 5.0 nM, 10.0 nM, 15.0 nM, 20.0 nM, 25.0 nM, 30.0 nM, 35.0 nM, 40.0 nM, 45.0 nM, 50.0 nM, 55.0 nM, 60.0 nM, 65.0 nM, 70.0 nM, 75.0 nM, 80.0 nM, 90.0 nM, 95.0 nM, or 100 nM or an amount that is within a range defined by any two of the aforementioned amounts. In some embodiments, the transduction of the signal affects cytokine signaling. In some embodiments, the transduction of the signal results in a signal that phenocopies interleukin-2 receptor (IL2R) signaling. In some embodiments, the transduction of the signal affects phosphorylation of a downstream target of a cytokine receptor. In some embodiments, following contact with the ligand, cells, such as mammalian cells, expressing the chemical-induced signaling complex are selectively expanded from a heterogeneous population of cells. In some embodiments, the ligand comprises rapamycin, and the cells, such as a mammalian cell, expressing the chemical-induced signaling complex are selectively expanded in vitro or in vivo by selectively inducing proliferation in chemical-induced signaling complex-expressing cells, while the rapamycin, preferably simultaneously, causes an anti-proliferative effect in non-chemical-induced signaling complex expressing cells, such as mammalian cells. In some embodiments, the selectively expanding cells, such as mammalian cells, have undergone two distinct gene targeting events. In some embodiments, each gene targeting event endows the cell, such as a mammalian cell, with one component of a chemical-induced signaling complex pair, such that only cells that have undergone both gene targeting events are able to expand following contact with the ligand.

Some embodiments provided herein relate to a protein sequence encoding components of a chemical-induced signaling complex component for homodimerization. In some embodiments, the protein sequence comprises a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the protein sequence comprises second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the first chemical-induced signaling complex component and the second chemical-induced signaling complex component are positioned such that when expressed, they form a population of 25% first chemical-induced signaling complex homodimers, 25% second chemical-induced signaling complex homodimers, and 50% of first/second chemical-induced signaling complex heterodimers in the presence of a ligand configured to bridge the homodimerizing domain.

In some embodiments, the first sequence comprises an amino acid sequence set forth in SEQ ID NO: 11. In some embodiments, the second sequence comprises an amino acid sequence set forth in SEQ ID NOs: 10 or 12. Some embodiments concern nucleic acids encoding the amino acid sequences of SEQ ID NOs: 10, 11, and 12.

In some embodiments, the signaling domain or a portion thereof of the first and second chemical-induced signaling complex components comprises one or more concatenated cytoplasmic signaling domains. In some embodiments, the homodimerizing domain comprises an FKBP domain or a mutant thereof or portions thereof, configured to bind a ligand, preferably simultaneously, such as AP1903 or a related rapalog, sodium mycophenolic acid, benidipine hydrochloride, or AP23573, or metabolites, derivatives, and/or combinations thereof. In some embodiments, the ligand is an IMID-class drug (e.g. thalidomide, pomalidomide, lenalidomide or related analogues).

Some embodiments provided herein relate to an expression vector for homodimeric CISC component expression comprising a nucleic acid encoding the first and/or second sequence of the protein sequence as provided herein. Accordingly, in some embodiments, the expression vector comprises a nucleic acid encoding a protein sequence encoding a chemical-induced signaling complex as set forth in SEQ ID NOs: 10, 11, and 12. In some embodiments, the expression vector encodes a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the expression vector encodes a second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the vector is RNA or DNA. In some embodiments, the vector is a lentiviral vector or an adeno-associated viral (AAV) vector. In some embodiments, the expression vector further comprises a promoter. In some embodiments, the promoter is an inducible promoter or a constitutive promoter.

Some embodiments provided herein relate to a cell, such as a mammalian cell, for homodimeric chemical-induced signaling complex expression. In some embodiments, the cell, such as a mammalian cell, comprises the protein sequence as described herein for homodimerizing component expression or the expression vector as described herein for homodimerizing component expression. Thus, in some embodiments a cell, such as a mammalian cell, is provided, which comprises a protein sequence encoding chemical-induced signaling complex components for homodimerization. In some embodiments, the protein sequence comprises a first sequence. In some embodiments, the first sequence encodes a first chemical-induced signaling complex comprising a homodimerizing domain or a portion thereof, a hinge domain, a transmembrane domain, and an interleukin-2 receptor subunit gamma (IL2Rg) signaling domain or portions thereof. In some embodiments, the protein sequence comprises second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the first chemical-induced signaling complex component and the second chemical-induced signaling complex component are positioned such that when expressed, they form a population of approximately 25% first chemical-induced signaling complex homodimers, 25% second chemical-induced signaling complex homodimers, and 50% of first/second chemical-induced signaling complex heterodimers in the presence of a ligand configured to bridge the homodimerizing domain. In some embodiments a cell, such as a mammalian cell, is provided, which comprises an expression vector for homodimeric chemical-induced signaling complex expression comprising a nucleic acid encoding the first and/or second sequence of the protein sequence as provided herein. Accordingly, in some embodiments, the expression vector comprises a nucleic acid encoding a protein sequence encoding a chemical-induced signaling complex. In some embodiments, the expression vector encodes a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the expression vector encodes a second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the vector is RNA or DNA. In some embodiments, the vector is a lentiviral vector or an adeno-associated viral (AAV) vector.

In some embodiments, the protein sequence for the homodimeric chemical-induced signaling complex comprises an amino acid sequence set forth in SEQ ID NO: 13 or SEQ ID NO: 14. Some embodiments concern nucleic acids encoding the amino acid sequences of SEQ ID NO: 13 and SEQ ID NO: 14.

In some embodiments, the chemical-induced signaling complex cell, such as a mammalian cell, is a precursor T cell or a T regulatory cell. In some embodiments, the cell, such as a mammalian cell, is a hematopoietic stem cell. In some embodiments, the cell is a CD34+, CD8+, or a CD4+ cell. In some embodiments, the cell is a CD8+ T cytotoxic lymphocyte cell selected from the group consisting of naïve CD8+ T cells, central memory CD8+ T cells, effector memory CD8+ T cells, and bulk CD8+ T cells. In some embodiments, the cell is a CD4+ T helper lymphocyte cell selected from the group consisting of naïve CD4+ T cells, central memory CD4+ T cells, effector memory CD4+ T cells, and bulk CD4+ T cells.

Some embodiments provided herein relate to a method of activating a signal into an interior of a cell, such as a mammalian cell, with a homodimerization chemical-induced signaling complex. In some embodiments, the method comprises providing the cell, such as a mammalian cell, as provided herein, expressing a protein sequence encoding a homodimeric chemical-induced signaling complex as provided herein or expressing the expression vector for the homodimeric chemical-induced signaling complex as provided herein, and contacting the cell with a dimerizing agent, thereby causing the first and second chemical-induced signaling complexes to dimerize, which transduces a signal into the interior of the cell. Accordingly, in some embodiments, the method comprises providing a cell, such as a mammalian cell, comprising the protein sequence as described herein for homodimeric CISC component expression or the expression vector as described herein for homodimeric CISC component expression. Thus, in some embodiments a cell, such as a mammalian cell, is provided, wherein the cell comprises a protein sequence encoding a chemical-induced signaling complex for homodimerization. In some embodiments, the protein sequence comprises a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the protein sequence comprises second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the first chemical-induced signaling complex component and the second chemical-induced signaling complex component are positioned such that when expressed, they form a population of approximately 25% first chemical-induced signaling complex homodimers, 25% second chemical-induced signaling complex homodimers, and 50% of first/second chemical-induced signaling complex heterodimers in the presence of a ligand configured to bridge the homodimerizing domain. In some embodiments a cell, such as a mammalian cell, is provided, wherein the cell comprises an expression vector for homodimeric CISC component expression comprising a nucleic acid encoding the first and/or second sequence of the protein sequence as provided herein. Accordingly, in some embodiments, the expression vector comprises a nucleic acid encoding a protein sequence encoding a chemical-induced signaling complex or components thereof. In some embodiments, the expression vector encodes a first sequence. In some embodiments, the first sequence encodes a first chemical-induced signaling complex component comprising a homodimerizing domain or a portion thereof, a hinge domain, a transmembrane domain, and an interleukin-2 receptor subunit gamma (IL2Rg) signaling domain or portions thereof. In some embodiments, the expression vector encodes a second sequence. In some embodiments, the second sequence encodes a second chemical-induced signaling complex component comprising the homodimerizing domain or a portion thereof, a hinge domain, a transmembrane domain, and an interleukin-2 receptor subunit beta (IL2Rb) signaling domain or portions thereof. In some embodiments, the vector is RNA or DNA. In some embodiments, the vector is a lentiviral vector or an adeno-associated viral (AAV) vector. In some embodiments, after providing said cell, such as a mammalian cell, the method further comprises expressing a protein sequence encoding the homodimeric chemical-induced signaling complex components as provided herein or expressing the expression vector for the homodimeric chemical-induced signaling complex components as provided herein, and contacting the cell with a dimerizing agent, thereby causing the first and second chemical-induced signaling complex components to dimerize, which transduces a signal into the interior of the cell.

In some embodiments, the dimerizing agent used is a ligand, such as rapamycin or a rapalog, such as everolimus, CCI-779, C20-methallylrapamycin, C16-(S)-3-methylindolerapamycin, C16-iRap, AP21967, sodium mycophenolic acid, benidipine hydrochloride, or AP23573, AP1903, or metabolites, derivatives, and/or combinations thereof. In some embodiments, the ligand is an IMID-class drug (e.g. thalidomide, pomalidomide, lenalidomide or related analogues). In some embodiments, the transduction of the signal affects cytokine signaling. In some embodiments, the transduction of the signal phenocopies interleukin-2 receptor (IL2R) signaling. In some embodiments, following contact with the dimerizing agent, cells, such as mammalian cells, expressing the chemical-induced signaling complex are selectively expanded from a heterogeneous population of cells. In some embodiments, rapamycin is the dimerizing agent, and is used to selectively expand a cell, such as a mammalian cell, population in vitro or in vivo by selectively inducing proliferation in chemical-induced signaling complex-expressing cells, while causing an anti-proliferative effect in non-chemical-induced signaling complex expressing cells.

Some embodiments provided herein relate to a protein sequence encoding a chemical-induced signaling complex component. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimeric CISCs in the presence of a ligand configured to bridge the homodimerizing domains. In some embodiments, the signaling domain or a portion thereof of comprises one or more concatenated cytoplasmic signaling domain. In some embodiments, the homodimerizing domain comprises an FKBP domain or an FRB or a portion thereof configured to bind to a ligand, preferably simultaneously, such as rapamycin.

Some embodiments provided herein relate to an expression vector comprising the nucleic acid encoding the protein sequence, as provided herein. Accordingly, in some embodiments, the expression vector comprises a nucleic acid encoding a protein sequence encoding a chemical-induced signaling complex. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimers in the presence of a ligand configured to bridge the homodimerizing domains. In some embodiments, the signaling domain or a portion thereof of comprises one or more concatenated cytoplasmic signaling domain. In some embodiments, the homodimerizing domain comprises an FKBP domain or an FRB or a portion thereof configured to bind to a ligand, preferably simultaneously, such as AP1903. In some embodiments, the expression vector further comprises a promoter. In some embodiments, the promoter is an inducible promoter or a constitutive promoter. In some embodiments, the vector is RNA or DNA. In some embodiments, the vector is a lentiviral vector or an adeno-associated viral (AAV) vector.

Some embodiments provided herein relate to a cell, such as a mammalian cell, for homodimeric chemical-induced signaling complex expression. In some embodiments, the cell, such as a mammalian cell, comprises the homodimerizing CISC component protein sequence as described herein or the expression vector encoding the nucleic acid sequence of the homodimeric protein sequence as described herein. Accordingly, in some embodiments, the cell, such as a mammalian cell, for homodimeric chemical-induced signaling complex expression comprises a protein sequence encoding a chemical-induced signaling complex. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex is positioned such that when expressed, it forms a population of homodimers in the presence of a ligand configured to bridge the homodimerizing domains. In some embodiments, the signaling domain or a portion thereof of comprises one or more concatenated cytoplasmic signaling domains. In some embodiments, the homodimerizing domain comprises an FKBP domain or an FRB or a portion thereof configured to bind to a ligand, preferably simultaneously, such as AP1903. In some embodiments, the cell, such as a mammalian cell, for homodimeric chemical-induced signaling complex expression comprises an expression vector comprises a nucleic acid encoding a protein sequence encoding a chemical-induced signaling complex component. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimers in the presence of a ligand configured to bridge the homodimerizing domains. In some embodiments, the signaling domain or a portion thereof of comprises one or more concatenated cytoplasmic signaling domains. In some embodiments, the homodimerizing domain comprises an FKBP domain or an FRB or a portion thereof configured to bind to a ligand, preferably simultaneously, such as AP1903. In some embodiments, the expression vector further comprises a promoter. In some embodiments, the promoter is an inducible promoter or a constitutive promoter. In some embodiments, the vector is RNA or DNA. In some embodiments, the vector is a lentiviral vector or an adeno-associated viral (AAV) vector.

In some embodiments, the cell, such as a mammalian cell, is a precursor T cell or a T regulatory cell. In some embodiments, the cell, such as a mammalian cell, is a hematopoietic stem cell. In some embodiments, the cell is a CD34+, CD8+, or a CD4+ cell. In some embodiments, the cell is a CD8+ T cytotoxic lymphocyte cell selected from the group consisting of naïve CD8+ T cells, central memory CD8+ T cells, effector memory CD8+ T cells, and bulk CD8+ T cells. In some embodiments, the cell is a CD4+ T helper lymphocyte cell selected from the group consisting of naïve CD4+ T cells, central memory CD4+ T cells, effector memory CD4+ T cells, and bulk CD4+ T cells.

Some embodiments provided herein relate to a method of activating a signal into an interior of a cell, such as a mammalian cell. In some embodiments, the method comprises providing the cell, such as a mammalian cell, for homodimeric chemical-induced signaling complex components as provided herein, expressing a protein sequence encoding a homodimeric chemical-induced signaling complex component as provided herein or expressing the expression vector encoding a nucleic acid for homodimeric chemical-induced signaling complex component expression as provided herein, and contacting the cell with a dimerizing agent, thereby causing the first and second chemical-induced signaling complex components to dimerize, which transduces a signal into the interior of the cell. Accordingly, in some embodiments, the method comprises providing a cell, such as a mammalian cell, which comprises the homodimerizing CISC component protein sequences, as described herein or the expression vector encoding the nucleic acid sequence of the homodimeric CISC component protein sequences as described herein. Accordingly, in some embodiments, the cell for homodimeric chemical-induced signaling complex component expression comprises a protein sequence encoding a chemical-induced signaling complex component. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimers in the presence of a ligand configured to bridge the homodimerizing domains. In some embodiments, the signaling domain or portion thereof of comprises one or more concatenated cytoplasmic signaling domains. In some embodiments, the homodimerizing domain comprises an FKBP domain or an FRB or a portion thereof configured to bind to a ligand, preferably simultaneously, such as AP1903. In some embodiments, the protein sequence further comprises a second sequence. In some embodiments, the cell, such as a mammalian cell, for homodimeric component expression comprises an expression vector comprises a nucleic acid encoding a protein sequence encoding a chemical-induced signaling complex component. In some embodiments, the protein sequence comprises a sequence encoding a chemical-induced signaling complex component comprising a homodimerizing domain or a portion thereof, a hinge domain, a transmembrane domain, and signaling domain or portions thereof. In some embodiments, the chemical-induced signaling complex component is positioned such that when expressed, it forms a population of homodimers in the presence of a ligand configured to bridge the homodimerizing domains. In some embodiments, the signaling domain or portion thereof of comprises one or more concatenated cytoplasmic signaling domains. In some embodiments, the homodimerizing domain comprises an FKBP domain or an FRB or a portion thereof configured to bind to a ligand, preferably simultaneously, such as AP1903. In some embodiments, the expression vector encodes a promoter. In some embodiments, the promoter is an inducible promoter or a constitutive promoter. In some embodiments, the vector is RNA or DNA. In some embodiments, the vector is a lentiviral vector or an adeno-associated viral (AAV) vector. In some embodiments, after providing the cell, such as a mammalian cell, the method further comprises expressing a protein sequence encoding a homodimeric CISC as provided herein or expressing the expression vector encoding a nucleic acid for homodimeric CISC expression as provided herein, and contacting the cell with a dimerizing agent, thereby causing the first and second CISC to dimerize, which transduces a signal into the interior of the cell.

In some embodiments, the dimerizing agent used is a ligand, such as rapamycin or a rapalog, such as everolimus, CCI-779, C20-methallylrapamycin, C16-(S)-3-methylindolerapamycin, C16-iRap, AP21967, sodium mycophenolic acid, benidipine hydrochloride, AP23573, or AP1903, or metabolites, derivatives, and/or combinations thereof. In some embodiments, the ligand is an IMID-class drug (e.g. thalidomide, pomalidomide, lenalidomide or related analogues). In some embodiments, the transduction of the signal affects cytokine signaling. In some embodiments, the transduction of the signal affects interleukin-2 receptor (IL2R) signaling. In some embodiments, following contact with the dimerizing agent, cells expressing CISC are selectively expanded from a heterogeneous population of cells, such as mammalian cells.

Some embodiments provided herein relate to a kit or a system including the components described herein. Thus, in some embodiments is provided a kit comprising one or more of: a protein sequence as described herein; an expression vector as described herein; and/or a cell as described herein. Some embodiments include a system for selectively activating a signal into an interior of a cell, comprising: a cell as described herein, wherein the cell comprises an expression vector as described herein comprising a nucleic acid encoding a protein sequence as described herein.

BRIEF DESCRIPTION OF THE DRAWINGS

FIG. 4B shows Western blots for the respective IL2R-CISC, comprising 1210, 1211, and 1233. Arrows indicate the detection of CISC component expression. Importantly, the 1233 architecture appears to express at the highest level.

FIG. 12 shows that only the cells expressing the IL2R-CISC V3 exhibited significant rapamycin-induced expansion over the course of the 25 days of the experiment.

FIG. 13 shows that cells expressing the IL2R-CISC V3 exhibited significant rapamycin-induced expansion over the course of the experiment, and that 1 nM rapamycin induced the most robust cell expansion.

FIG. 16 demonstrates that cells expressing the IL2R-CISC V3 exhibited significant AP21967-induced expansion over the course of the experiment, and that 100 nM AP21967 induced the most robust cell expansion.

DETAILED DESCRIPTION

Figure 1:
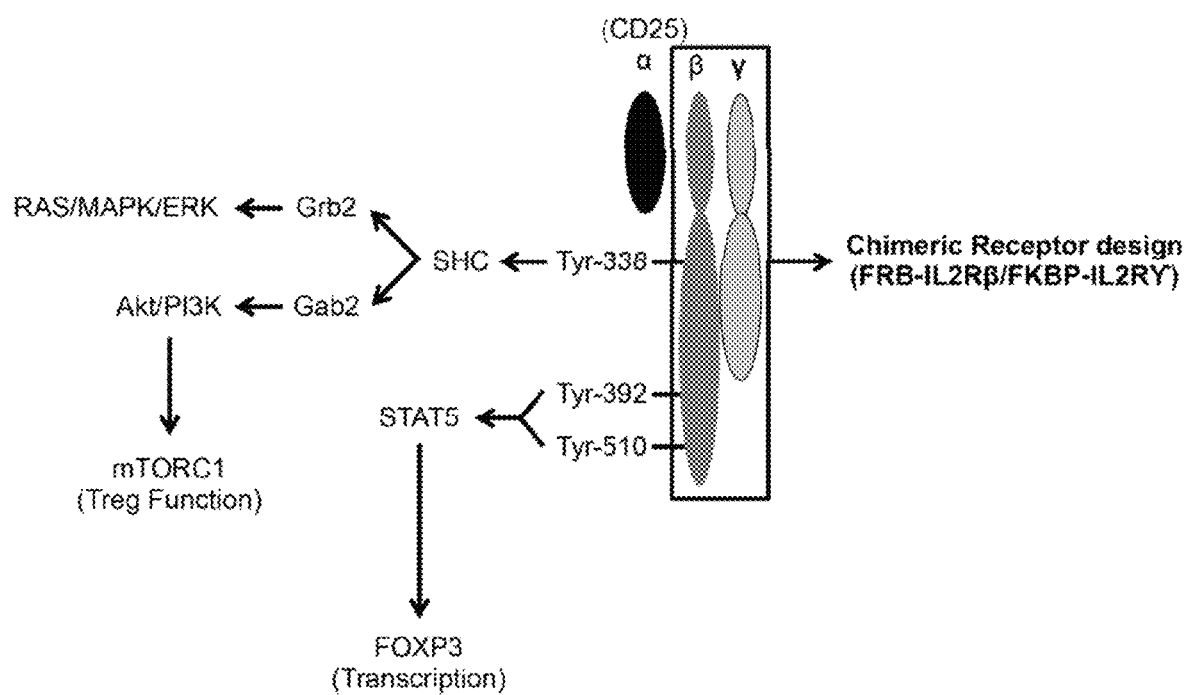
FIG. 1 is a schematic diagram illustrating IL-2 signaling in T-cell expansion. The diagram depicts chimeric dimerization of IL-2 chains comprising FRB-CD250 (transmembrane (TM) and cytoplasmic domains) (IL2Rβ) and FKBP-CD25γ (TM and cytoplasmic domains) (IL2Rγ), resulting in downstream signaling pathways. Importantly, removal of most or all of the extracellular domains prevents binding of IL2 to these chemical-induced signaling complex components, thus they are not responsive to endogenous IL2.

Described herein are compositions of chemical-induced signaling complex (CISC), and methods of making and using the same. The CISC can be used for activating a signal through a signaling pathway in a cell and for the selective expansion of cells.

Definitions

Unless defined otherwise, all technical and scientific terms used herein have the same meaning as commonly understood by one of ordinary skill in the art to which the disclosure pertains. All patents, applications, published applications and other publications referenced herein are expressly incorporated by reference in their entireties unless stated otherwise. In the event that there are a plurality of definitions for a term herein, those in this section prevail unless stated otherwise.

As used herein, "a" or "an" may mean one or more than one.

"About" has its plain and ordinary meaning when read in light of the specification, and may be used, for example, when referring to a measurable value and may be meant to encompass variations of 20% or ±10%, more preferably +5%, even more preferably +1%, and still more preferably +0.1% from the specified value.

As used herein, "protein sequence" refers to a polypeptide sequence of amino acids that is the primary structure of a protein. As used herein "upstream" refers to positions 5' of a location on a polynucleotide, and positions toward the N-terminus of a location on a polypeptide. As used herein "downstream" refers to positions 3' of a location on nucleotide, and positions toward the C-terminus of a location on a polypeptide. Thus, the term "N-terminal" refers to the position of an element or location on a polynucleotide toward the N-terminus of a location on a polypeptide.

"Nucleic acid" or "nucleic acid molecule" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Modified nucleotides can have alterations in sugar moieties and/or in pyrimidine or purine base moieties. Sugar modifications include, for example, replacement of one or more hydroxyl groups with halogens, alkyl groups, amines, and azido groups, or sugars can be functionalized as ethers or esters. Moreover, the entire sugar moiety can be replaced with sterically and electronically similar structures, such as aza-sugars and carbocyclic sugar analogs. Examples of modifications in a base moiety include alkylated purines and pyrimidines, acylated purines or pyrimidines, or other well-known heterocyclic substitutes. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, and the like. The term "nucleic acid molecule" also comprises so-called "peptide nucleic acids," which comprise naturally-occurring or modified nucleic acid bases attached to a polyamide backbone. Nucleic acids can be either single stranded or double stranded. In some embodiments, a nucleic acid sequence encoding a fusion protein is provided. In some embodiments, the nucleic acid is RNA or DNA.

"Coding for" or "encoding" are used herein, and refers to the property of specific sequences of nucleotides in a polynucleotide, such as a gene, a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system.

A "nucleic acid sequence coding for a polypeptide" comprises all nucleotide sequences that are degenerate versions of each other and that code for the same amino acid sequence. In some embodiments, a nucleic acid is provided, wherein the nucleic acid encodes a fusion protein.

"Vector," "expression vector," or "construct" is a nucleic acid used to introduce heterologous nucleic acids into a cell that has regulatory elements to provide expression of the heterologous nucleic acids in the cell. Vectors include but are not limited to plasmid, minicircles, yeast, and viral genomes. In some embodiments, the vectors are plasmid, minicircles, yeast, or viral genomes. In some embodiments, the vector is a viral vector. In some embodiments, the viral vector is a lentivirus. In some embodiments, the vector is an adeno-associated viral (AAV) vector. In some embodiments, the vector is for protein expression in a bacterial system such as E. coli. As used herein, the term "expression," or "protein expression" refers to refers to the translation of a transcribed RNA molecule into a protein molecule. Protein expression may be characterized by its temporal, spatial, developmental, or morphological qualities as well as by quantitative or qualitative indications. In some embodiments, the protein or proteins are expressed such that the proteins are positioned for dimerization in the presence of a ligand.

As used herein, "fusion proteins" or "chimeric proteins" are proteins created through the joining of two or more genes that originally coded for separate proteins or portions of proteins. The fusion proteins can also be made up of specific protein domains from two or more separate proteins. Translation of this fusion gene can result in a single or multiple polypeptides with functional properties derived from each of the original proteins. Recombinant fusion proteins can be created artificially by recombinant DNA technology for use in biological research or therapeutics. Such methods for creating fusion proteins are known to those skilled in the art. Some fusion proteins combine whole peptides and therefore can contain all domains, especially functional domains, of the original proteins. However, other fusion proteins, especially those that are non-naturally occurring, combine only portions of coding sequences and therefore do not maintain the original functions of the parental genes that formed them. In some embodiments, a fusion protein is provided, wherein the fusion protein comprises an interferon and a PD-1 protein.

As used herein, the term "regulatory element" refers to a DNA molecule having gene regulatory activity, e.g., one that has the ability to affect the transcription and/or translation of an operably linked transcribable DNA molecule. Regulatory elements such as promoters, leaders, introns, and transcription termination regions are DNA molecules that have gene regulatory activity and play an integral part in the overall expression of genes in living cells. Isolated regulatory elements, such as promoters, that function in plants are therefore useful for modifying plant phenotypes through the methods of genetic engineering.

As used herein, the term "operably linked" refers to a first molecule joined to a second molecule, wherein the molecules are so arranged that the first molecule affects the function of the second molecule. The two molecules may be part of a single contiguous molecule and may be adjacent. For example, a promoter is operably linked to a transcribable DNA molecule if the promoter modulates transcription of the transcribable DNA molecule of interest in a cell.

A "promoter" is a region of DNA that initiates transcription of a specific gene. The promoters can be located near the transcription start site of a gene, on the same strand and upstream on the DNA (the 5' region of the sense strand). The promoter can be a conditional, inducible or a constitutive promoter. The promoter can be specific for bacterial, mammalian or insect cell protein expression. In some embodiments, wherein a nucleic acid encoding a fusion protein is provided, the nucleic acid further comprises a promoter sequence. In some embodiments, the promoter is specific for bacterial, mammalian or insect cell protein expression. In some embodiments, the promoter is a conditional, inducible or a constitutive promoter "Conditional" or "inducible" as used herein refers to a nucleic acid construct that comprises a promoter that provides for gene expression in the presence of an inducer and does not substantially provide for gene expression in the absence of the inducer.

"Constitutive" as used herein refer to the nucleic acid construct that comprises a promoter that is constitutive, and thus provides for expression of a polypeptide that is continuously produced.

In some embodiments, the inducible promoter has a low level of basal activity. In some embodiments, wherein a lentiviral vector is used, the level of basal activity in uninduced cells is 20%, 15%, 10%, 5%, 4%, 3%, 2%, 1% or less (but not zero) or within a range defined by any two of the aforementioned values, as compared to when cells are induced to express the gene. The level of basal activity can be determined by measuring the amount of the expression of the transgene (e.g. marker gene) in the absence of the inducer (e.g. drug) using flow cytometry. In some embodiments described herein a marker protein such as Akt is used for determination of expression.

In some embodiments, the inducible promoter provides for a high level of induced activity, as compared to uninduced or basal activity. In some embodiments, the level of activity in the induced state is 2, 4, 6, 8, 9 or 10 fold or greater than the activity level in the uninduced state or within a range defined by any two of the aforementioned values. In some embodiments, transgene expression under control of the inducible promoter is turned off in the absence of a transactivator in less than 10, 8, 6, 4, 2, or 1 days excluding 0 days or within a range defined by any two of the aforementioned time periods.

In some embodiments, an inducible promoter is designed and/or modified to provide for a low level of basal activity, a high level of inducibility, and/or a short time for reversibility.

"Dimeric chemical-induced signaling complex," "dimeric CISC," or "dimer" as used herein refers to two components of a CISC, which may or may not be fusion protein complexes that join together. "Dimerization" refers to the process of the joining together of two separate entities into a single entity. In some embodiments, a ligand or agent stimulates dimerization. In some embodiments, dimerization refers to homodimerization, or the joining of two identical entities, such as two identical CISC components. In some embodiments, dimerization refers to heterodimerization, of the joining of two different entities, such as two different and distinct CISC components. In some embodiments, the dimerization of the CISC components results in a cellular signaling pathway. In some embodiments, the dimerization of the CISC components allows for the selective expansion of a cell or a population of cells. Additional CISC systems can include a CISC gibberellin CISC dimerization system, or a SLF-TMP CISC dimerization system. Other chemically inducible dimerization (CID) systems and component parts may be used.

As used herein, "chemical-induced signaling complex" or "CISC" refers to an engineered complex that initiates a signal into the interior of a cell as a direct outcome of ligand-induced dimerization. A CISC may be a homodimer (dimerization of two identical components) or a heterodimer (dimerization of two distinct components). Thus, as used herein the term "homodimer" refers to a dimer of two protein components described herein with identical amino acid sequences. The term "heterodimer" refers to a dimer of two protein components described herein with non-identical amino acid sequences.

The CISC may be a synthetic complex as described herein in greater detail. "Synthetic" as used herein refers to a complex, protein, dimer, or composition, as described herein, which is not natural, or that is not found in nature. In some embodiments, an IL2R-CISC refers to a signaling complex that involves interleukin-2 receptor components. In some embodiments, an IL2/15-CISC refers to a signaling complex that involves receptor signaling subunits that are shared by interleukin-2 and interleukin-15. In some embodiments, an IL7-CISC refers to a signaling complex that involves an interleukin-7 receptor components. A CISC may thus be termed according to the component parts that make up the components of a given CISC. One of skill in the art will recognize that the component parts of the chemical-induced signaling complex may be composed of a natural or a synthetic component useful for incorporation into a CISC. Thus, the examples provided herein are not intended to be limiting.

As used herein, "cytokine receptor" refers to receptor molecules that recognize and bind to cytokines. In some embodiments, cytokine receptor encompasses modified cytokine receptor molecules (e.g., "variant cytokine receptors"), comprising those with substitutions, deletions, and/or additions to the cytokine receptor amino acid and/or nucleic acid sequence. Thus, it is intended that the term encompass wild-type, as well as, recombinant, synthetically-produced, and variant cytokine receptors. In some embodiments, the cytokine receptor is a fusion protein, comprising an extracellular binding domain, a hinge domain, a transmembrane domain, and a signaling domain. In some embodiments, the components of the receptor (that is, the domains of the receptor) are natural or synthetic. In some embodiments, the domains are human derived domains.

"FKBP" as used herein, is a FK506 binding protein domain. FKBP refers to a family of proteins that have prolyl isomerase activity and are related to the cyclophilins in function, though not in amino acid sequence. FKBPs have been identified in many eukaryotes from yeast to humans and function as protein folding chaperones for proteins containing proline residues. Along with cyclophilin, FKBPs belong to the immunophilin family. The term FKBP comprises, for example, FKBP12 as well as, proteins encoded by the genes AIP; AIPL1; FKBP1A; FKBP1B; FKBP2; FKBP3; FKBP5; FKBP6; FKBP7; FKBP8; FKBP9; FKBP9L; FKBP10; FKBP11; FKBP14; FKBP15; FKBP52; and/or LOC541473; comprising homologs thereof and functional protein fragments thereof.

"FRB" as used herein, as a FKBP rapamycin binding domain. FRB domains are polypeptide regions (protein "domains") that are configured to form a tripartite complex with an FKBP protein and rapamycin or rapalog thereof. FRB domains are present in a number of naturally occurring proteins, comprising mTOR proteins (also referred to in the literature as FRAP, RAPT 1, or RAFT) from human and other species; yeast proteins comprising Tor1 and/or Tor2; and a *Candida* FRAP homolog. Both FKBP and FRB are major constituents in the mammalian target of rapamycin (mTOR) signaling.

Cereblon interacts with damaged DNA binding protein 1 and forms an E3 ubiquitin ligase complex with Cullin 4 where it functions as a substrate receptor in which the proteins recognized by cereblon may be ubiquitinated and degraded by proteasomes. Proteasome-mediated degradation of unneeded or damaged proteins plays a very important role in maintaining regular function of a cell, such as cell survival, proliferation and/or growth. The binding of immunomodulatory imide drugs (IMIDs), e.g. thalidomide, to cereblon has been associated with teratogenicity and also the cytotoxicity of IMIDs, including lenalidomide. Cereblon is a key player in the binding, ubiquitination, and degradation of factors involved in maintaining function of myeloma cells.

"Cereblon thalidomide binding domain" refers to a binding domain that is an extracellular binding domain that interacts with an IMID, comprising, for example, thalidomide, pomalidomide, lenalidomide, apremilast, or related analogues. Some embodiments provided herein utilize cereblon thalidomide binding domain analogues or mutants thereof. In some embodiments, these extracellular binding domains are configured to simultaneously bind to an IMID ligand.

In some embodiments, the immunomodulatory imide drug used in the approaches described herein may comprise:
thalidomide (including analogues, derivatives, and including pharmaceutically acceptable salts thereof. Thalidomide may include Immunoprin, Thalomid, Talidex, Talizer, Neurosedyn, α-(N-Phthalimido)glutarimide, 2-(2,6-dioxopiperidin-3-yl)-2,3-dihydro-1H-isoindole-1,3-dione);
pomalidomide (including analogues, derivatives, and including pharmaceutically acceptable salts thereof. Pomalidomide may include Pomalyst, Imnovid, (RS)-4-Amino-2-(2,6-dioxopiperidin-3-yl)isoindole-1,3-dione);
lenalidomide (including analogues, derivatives, and including pharmaceutically acceptable salts thereof. Lenalidomide may include Revlimid, (RS)-3-(4-Amino-1-oxo-1,3-dihydro-2H-isoindol-2-yl)piperidine-2,6-dione); or
apremilast (including analogues, derivatives, and including pharmaceutically acceptable salts thereof. Apremilast may include Otezla, CC-10004, N-{2-[(1S)-1-(3-Ethoxy-4-methoxyphenyl)-2-(methylsulfonyl)ethyl]-1,3-dioxo-2,3-dihydro-1H-isoindol-4-yl}acetamide);
or any combinations thereof.

As used herein, the term "extracellular binding domain" refers to a domain of a complex that is outside of the cell, and which is configured to bind to a specific atom or molecule. In some embodiments, the extracellular binding domain of a CISC is a FKBP domain or a portion thereof. In some embodiments, the extracellular binding domain is an FRB domain or a portion thereof. In some embodiments, the extracellular binding domain is configured to bind a ligand or agent, thereby stimulating dimerization of two CISC components. In some embodiments, the extracellular binding domain is configured to bind to a cytokine receptor modulator.

As used herein, the term "cytokine receptor modulator" refers to an agent, which modulates the phosphorylation of a downstream target of a cytokine receptor, the activation of a signal transduction pathway associated with a cytokine receptor, and/or the expression of a particular protein such as a cytokine. Such an agent may directly or indirectly modulate the phosphorylation of a downstream target of a cytokine receptor, the activation of a signal transduction pathway associated with a cytokine receptor, and/or the expression of a particular protein such as a cytokine. Thus, examples of cytokine receptor modulators include, but are not limited to, cytokines, fragments of cytokines, fusion proteins and/or antibodies or binding portions thereof that immunospecifically bind to a cytokine receptor or a fragment thereof. Further, examples of cytokine receptor modulators include, but are not limited to, peptides, polypeptides (e.g., soluble cytokine receptors), fusion proteins and/or antibodies or binding portions thereof that immunospecifically bind to a cytokine or a fragment thereof.

As used herein, the term "activate" refers to an increase in at least one biological activity of a protein of interest. Similarly, the term "activation" refers to a state of a protein of interest being in a state of increased activity. The term "activatable" refers to the ability of a protein of interest to become activated in the presence of a signal, an agent, a ligand, a compound, or a stimulus. In some embodiments, a dimer, as described herein, is activated in the presence of a signal, an agent, a ligand, a compound, or a stimulus, and becomes a signaling competent dimer. As used herein, the term "signaling competent" refers to the ability or configuration of the dimer so as to be capable of initiating or sustaining a downstream signaling pathway.

As used herein, the term "hinge domain" refers to a domain that links the extracellular binding domain to the transmembrane domain, and may confer flexibility to the extracellular binding domain. In some embodiments, the hinge domain positions the extracellular domain close to the plasma membrane to minimize the potential for recognition by antibodies or binding fragments thereof. In some embodiments, the extracellular binding domain is located N-terminal to the hinge domain. In some embodiments, the hinge domain may be natural or synthetic.

As used herein, the term "transmembrane domain" or "TM domain" refers to a domain that is stable in a membrane, such as in a cell membrane. The terms "transmembrane span," "integral protein," and "integral domain" are also used herein. In some embodiments, the hinge domain and the extracellular domain is located N-terminal to the transmembrane domain. In some embodiments, the transmembrane domain is a natural or a synthetic domain. In some embodiments, the transmembrane domain is an IL-2 transmembrane domain.

As used herein, the term "signaling domain" refers to a domain of the fusion protein or CISC component that is involved in a signaling cascade inside the cell, such as a mammalian cell. A signaling domain refers to a signaling moiety that provides to cells, such as T-cells, a signal which, in addition to the primary signal provided by for instance the CD3 zeta chain of the TCR/CD3 complex, mediates a cellular response, such as a T-cell response, comprising, but not limited to, activation, proliferation, differentiation, and/or cytokine secretion. In some embodiments, the signaling domain is N-terminal to the transmembrane domain, the hinge domain, and the extracellular domain. In some embodiments, the signaling domain is a synthetic or a natural domain. In some embodiments, the signaling domain is a concatenated cytoplasmic signaling domain. In some embodiments, the signaling domain is a cytokine signaling domain. In some embodiments, the signaling domain is an antigen signaling domain. In some embodiments, the signaling domain is an interleukin-2 receptor subunit gamma (IL2Rγ or IL2Rg) domain. In some embodiments, the signaling domain is an interleukin-2 receptor subunit beta (IL2Rβ or IL2Rb) domain. In some embodiments, binding of an agent or ligand to the extracellular binding domain causes a signal transduction through the signaling domain by the activation of a signaling pathway, as a result of dimerization of the CISC components. As used herein, the term "signal transduction" refers to the activation of a signaling pathway by a ligand or an agent binding to the extracellular domain. Activation of a signal is a result of the binding of the extracellular domain to the ligand or agent, resulting in CISC dimerization.

As used herein, the term "IL2Rb" or "IL2R β" refers to an interleukin-2 receptor subunit beta. Similarly, the term "IL2Rg" or IL2Rγ" refers to an interleukin-2 receptor subunit gamma, and the term "IL2Ra" or "IL2Rα" refers to an interleukin-2 receptor subunit alpha. The IL-2 receptor has three forms, or chains, alpha, beta, and gamma, which are also subunits for receptors for other cytokines. IL2Rβ and IL2Rγ are members of the type I cytokine receptor family. "IL2R" as used herein refers to interleukin-2 receptor, which is involved in T cell-mediated immune responses. IL2R is involved in receptor-mediated endocytosis and transduction of mitogenic signals from interleukin 2. Similarly, the term "IL-2/15R" refers to a receptor signaling subunit that is shared by IL-2 and IL-15, and may include a subunit alpha (IL2/15Ra or IL2/15Rα), beta (IL2/15Rb or IL2/15Rβ, or gamma (IL2/15Rg or IL2/15Rγ).

In some embodiments, a chemical-induced signaling complex is a heterodimerization activated signaling complex comprising two components. In some embodiments, the first component comprises an extracellular binding domain that is one part of a heterodimerization pair, an optional hinge domain, a transmembrane domain, and one or more concatenated cytoplasmic signaling domains. In some embodiments, the second component comprises an extracellular binding domain that is the other part of a heterodimerization pair, an optional hinge domain, a transmembrane domain, and one or more concatenated cytoplasmic signaling domains. Thus, in some embodiments, there are two distinct modification events. In some embodiments, the two CISC components are expressed in a cell, such as a mammalian cell. In some embodiments, the cell, such as a mammalian cell, or a population of cells, such as a population of mammalian cells, is contacted with a ligand or agent that causes heterodimerization, thereby initiating a signal. In some embodiments, a homodimerization pair dimerize, whereby a single CISC component is expressed in a cell, such as a mammalian cell, and the CISC components homodimerize to initiate a signal.

As used herein, the term "ligand" or "agent" refers to a molecule that has a desired biological effect. In some embodiments, a ligand is recognized by and bound by an extracellular binding domain, forming a tripartite complex comprising the ligand and two binding CISC components. Ligands include, but are not limited to, proteinaceous molecules, comprising, but not limited to, peptides, polypeptides, proteins, post-translationally modified proteins, antibodies, binding portions thereof; small molecules (less than 1000 Daltons), inorganic or organic compounds; and nucleic acid molecules comprising, but not limited to, double-stranded or single-stranded DNA, or double-stranded or single-stranded RNA (e.g., antisense, RNAi, etc.), aptamers, as well as, triple helix nucleic acid molecules. Ligands can be derived or obtained from any known organism (comprising, but not limited to, animals (e.g., mammals (human and non-human mammals)), plants, bacteria, fungi, and protista, or viruses) or from a library of synthetic molecules. In some embodiments, the ligand is a protein, an antibody or portion thereof, a small molecule, or a drug. In some embodiments, the ligand is rapamycin or a rapamycin analog (rapalogs). In some embodiments, the rapalog comprises variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and alternative substitution on the cyclohexyl ring or replacement of the cyclohexyl ring with a substituted cyclopentyl ring. Thus, in some embodiments, the rapalog is everolimus, merilimus, novolimus, pimecrolimus, ridaforolimus, tacrolimus, temsirolimus, umirolimus, zotarolimus, CCI-779, C20-methallylrapamycin, C16-(S)-3-methylindolerapamycin, C16-iRap, AP21967, sodium mycophenolic acid, benidipine hydrochloride, AP23573, or AP1903, or metabolites, derivatives, and/or combinations thereof. In some embodiments, the ligand is an IMID-class drug (e.g. thalidomide, pomalidomide, lenalidomide or related analogues).

Accordingly, in some embodiments, the ligand or agent used in the approaches described herein for chemical induction of the signaling complex may comprise:

rapamycin (including analogues, derivatives, and including pharmaceutically acceptable salts thereof. Rapamycin may include Sirolimus, Rapamune, (3S,6R,7E,9R, 10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R, 4R)-4-hydroxy-3-methoxycyclohexyl]-1-methylethyl]-10,21-dimethoxy-6,8,12,14,20,26-hexamethyl-23,27-epoxy-3H-pyrido[2,1-c][1,4] oxaazacyclohentriacontine-1,5,11,28,29 (4H,6H,31H)-pentone);

everolimus (including analogues, derivatives, and including pharmaceutically acceptable salts thereof. Everolimus may include RAD001, Zortress, Certican, Afinitor, Votubia, 42-O-(2-hydroxyethyl)rapamycin, (1R,9S, 12S,15R,16E,18R,19R,21R,23S,24E,26E,28E,30S, 32S,35R)-1,18-dihydroxy-12-[(2R)-1-[(1S,3R,4R)-4-(2-hydroxyethoxy)-3-methoxycyclohexyl]propan-2-yl]-19,30-dimethoxy-15,17,21,23,29,35-hexamethyl-11,36-dioxa-4-azatricyclo[30.3.1.0$^{4,9}$]hexatriaconta-16,24,26,28-tetraene-2,3,10,14,20-pentone);

merilimus (including analogues, derivatives, and including pharmaceutically acceptable salts thereof. Merilimus may include SAR943, 42-O-(tetrahydrofuran-3-yl)rapamycin (Merilimus-1); 42-O-(oxetan-3-yl) rapamycin (Merilimus-2), 42-O-(tetrahydropyran-3-yl) rapamycin (Merilimus-3), 42-O-(4-methyl, tetrahydrofuran-3-yl)rapamycin, 42-O-(2,5,5-trimethyl, tetrahydrofuran-3-yl) rapamycin, 42-O-(2,5-diethyl-2-methyl, tetrahydrofuran-3-yl)rapamycin, 42-O-(2H-Pyran-3-yl, tetrahydro-6-methoxy-2-methyl) rapamycin, or 42-O-(2H-Pyran-3-yl, tetrahydro-2,2-dimethyl-6-phenyl)rapamycin);

novolimus (including analogues, derivatives, and including pharmaceutically acceptable salts thereof. Novolimus may include 16-O-Demethyl Rapamycin);

pimecrolimus (including analogues, derivatives, and including pharmaceutically acceptable salts thereof. Pimecrolimus may include Elidel, (3S,4R,5S,8R,9E, 12S,14S,15R,16S,18R,19R,26aS)-3-((E)-2-((1R,3R, 4S)-4-chloro-3 methoxycyclohexyl)-1-methylvinyl)-8-ethyl 5,6,8,11,12,13,14,15,16,17,18,19,24,26, 26ahexadecahydro-5,19-epoxy-3H-pyrido(2,1-c)(1,4) oxaazacyclotricosine-1,17,20,21(4H,23H)-tetrone 33-epi-Chloro-33-desoxyascomycin);

ridaforolimus (including analogues, derivatives, and including pharmaceutically acceptable salts thereof. Ridaforolimus may include AP23573, MK-8669, deforolimus, (1R,9S,12S,15R,16E,18R,19R,21R,23S, 24E,26E,28E,30S,32S,35R)-12-((1R)-2-((1S,3R,4R)-4-((Dimethylphosphinoyl)oxy)-3-methoxycyclohexyl)-1-methylethyl)-1,18-dihydroxy-19,30-dimethoxy 15,17,21,23,29,35-hexamethyl-11,36-dioxa-4-azatricyclo(30.3.1.04,9)hexatriaconta-16,24, 26,28-tetraene-2,3,10,14,20-pentone);

tacrolimus (including analogues, derivatives, and including pharmaceutically acceptable salts thereof. Tacrolimus may include FK-506, fujimycin, Prograf, Advagraf, protopic, 3S-[3R*[E(1S*,3S*,4S*)],4S*,5R*, 8S*,9E,12R*,14R*,15S*,16R*,18S*,19S*,26aR*5,6, 8,11,12,13,14,15,16,17,18,19, 24,25,26,26a-hexadecahydro-5,19-dihydroxy-3-[2-(4-hydroxy-3-methoxycyclohexyl)-1-methylethenyl]-14,16-dimethoxy-4,10,12,18-tetramethyl-8-(2-propenyl)-15, 19-epoxy-3H-pyrido[2,1-c][1,4] oxaazacyclotricosine-1,7,20,21(4H,23H)-tetrone, monohydrate);

temsirolimus (including analogues, derivatives, and including pharmaceutically acceptable salts thereof. Temsirolimus may include CCI-779, CCL-779, Torisel, (1R,2R,4S)-4-{(2R)-2-[(3S,6R,7E,9R,10R,12R,14S, 15E,17E,19E,21S,23S,26R,27R,34aS)-9,27-dihydroxy-10,21-dimethoxy-6,8,12,14,20,26-hexamethyl-1,5,11,28,29-pentaoxo-1,4,5,6,9,10,11,12,13,14,21,22, 23,24,25,26,27,28,29,31,32,33,34,34a-tetracosahydro-3H-23,27-epoxypyrido[2,1-c][1,4] oxazacyclohentriacontin-3-yl]propyl}-2-methoxycyclohexyl 3-hydroxy-2-(hydroxymethyl)-2-methylpropanoate);

umirolimus (including analogues, derivatives, and including pharmaceutically acceptable salts thereof. Umirolimus may include Biolimus, Biolimus A9, BA9, TRM-986, 42-O-(2-ethoxyethyl)Rapamycin);

zotarolimus (including analogues, derivatives, and including pharmaceutically acceptable salts thereof. Zotarolimus may include ABT-578, (42S)-42-Deoxy-42-(1H-tetrazol-1-yl)-rapamycin);

C20-methallylrapamycin (including analogues, derivatives, and including pharmaceutically acceptable salts thereof. C20-methallylrapamycin may include C20-Marap);

C16-(S)-3-methylindolerapamycin (including analogues, derivatives, and including pharmaceutically acceptable salts thereof. C16-(S)-3-methylindolerapamycin may include C16-iRap);

AP21967 (including analogues, derivatives, and including pharmaceutically acceptable salts thereof. AP21967 may include C-16-(S)-7-methylindolerapamycin);

sodium mycophenolic acid (including analogues, derivatives, and including pharmaceutically acceptable salts thereof. Sodium mycophenolic acid may include CellCept, Myfortic, (4E)-6-(4-Hydroxy-6-methoxy-7-methyl-3-oxo-1,3-dihydro-2-benzofuran-5-yl)-4-methylhex-4-enoic acid);

benidipine hydrochloride (including analogues, derivatives, and including pharmaceutically acceptable salts thereof. Benidipine hydrochloride may include Benidipinum, Coniel); or AP1903 (including analogues, derivatives, and including pharmaceutically acceptable salts thereof. AP1903 may include Rimiducid, [(1R)-3-(3,4-dimethoxyphenyl)-1-[3-[2-[2-[[2-[3-[(1R)-3-(3,4-dimethoxyphenyl)-1-[(2S)-1-[(2S)-2-(3,4,5-trimethoxyphenyl)butanoyl]piperidine-2-carbonyl] oxypropyl]phenoxy]acetyl]amino]ethylamino]-2-oxoethoxy]phenyl]propyl] (2S)-1-[(2S)-2-(3,4,5-trimethoxyphenyl)butanoyl]piperidine-2-carboxylate);

or any combinations thereof.

As used herein, the term "gibberellin" refers to a synthetic or naturally occurring form of the diterpenoid acids that are synthesized by the terpenoid pathway in plastids and then modified in the endoplasmic reticulum and cytosol until they reach their biologically-active form. Gibberellin may be a natural gibberellin or an analogue thereof, including, for example, gibberellins derived from the ent-gibberellane skeleton, or synthesized via ent-kauren, including gibberelling 1 (GA1), GA2, GA3 . . . GA136, and analogues and derivatives thereof. In some embodiments, gibberellin or an analogue or derivative thereof is utilized for CISC dimerization.

As used herein, "SLF-TMP" or "synthetic ligand of FKBP linked to trimethoprim" refers to a dimerizer for CISC dimerization. In some embodiments, the SLF moiety binds to a first CISC component and the TMP moiety binds to a second CISC component, causing CISC dimerization. In some embodiments, SLF can bind, for example, to FKBP and TMP can bind to *E. coli* dihydrofolate reductase (eDHFR).

As used herein, the term "simultaneous binding" refers to the binding of the ligand by two or more CISC components at the same time or, in some cases, at substantially the same time, to form a multicomponent complex, comprising the CISC components and the ligand component, and resulting in subsequent signal activation. Simultaneous binding requires that the CISC components are configured spatially to bind a single ligand, and also that both CISC components are configured to bind to the same ligand, including to different moieties on the same ligand.

As used herein, the term "selective expansion" refers to an ability of a desired cell, such as a mammalian cell, or a desired population of cells, such as a population of mammalian cells, to expand. In some embodiments, selective expansion refers to the generation or expansion of a pure population of cells, such as mammalian cells, that have undergone two genetic modification events. One component of a dimerization CISC is part of one modification and the other component is the other modification. Thus, one component of the heterodimerizing CISC is associated with each genetic modification. Exposure of the cells to a ligand allows for selective expansion of only the cells, such as mammalian cells, having both desired modifications. Thus, in some embodiments, the only cells, such as mammalian cells, that will be able to respond to contact with a ligand are those that express both components of the heterodimerization CISC.

As used herein, "host cell" comprises any cell type, such as a mammalian cell, that is susceptible to transformation, transfection, or transduction, with a nucleic acid construct or vector. In some embodiments, the host cell, such as a mammalian cell, is a T cell or a T regulatory cell (Treg). In some embodiments, the host cell, such as a mammalian cell, is a hematopoietic stem cell. In some embodiments, the host cell is a CD34+, CD8+, or a CD4+ cell. In some embodiments, the host cell is a CD8+ T cytotoxic lymphocyte cell selected from the group consisting of naïve CD8+ T cells, central memory CD8+ T cells, effector memory CD8+ T cells, and bulk CD8+ T cells. In some embodiments, the host cell is a CD4+ T helper lymphocyte cell selected from the group consisting of naïve CD4+ T cells, central memory CD4+ T cells, effector memory CD4+ T cells, and bulk CD4+ T cells. As used herein, the term "population of cells" refers to a group of cells, such as mammalian cells, comprising more than one cell. In some embodiments, a cell, such as a mammalian cell, is manufactured, wherein the cell comprises the protein sequence as described herein or an expression vector that encodes the protein sequence as described herein.

As used herein, the term "transformed" or "transfected" refers to a cell, such as a mammalian cell, tissue, organ, or organism into which a foreign polynucleotide molecule, such as a construct, has been introduced. The introduced polynucleotide molecule may be integrated into the genomic DNA of the recipient cell, such as a mammalian cell, tissue, organ, or organism such that the introduced polynucleotide molecule is inherited by subsequent progeny. A "transgenic" or "transfected" cell, such as a mammalian cell, or organism also comprises progeny of the cell or organism and progeny produced from a breeding program employing such a transgenic organism as a parent in a cross and exhibiting an altered phenotype resulting from the presence of a foreign polynucleotide molecule. The term "transgenic" refers to a bacteria, fungi, or plant containing one or more heterologous polynucleic acid molecules. "Transduction" refers to virus-mediated gene transfer into cells, such as mammalian cells.

As used herein, a "subject" refers to an animal that is the object of treatment, observation or experiment. "Animal" comprises cold- and warm-blooded vertebrates and invertebrates such as fish, shellfish, reptiles and, in particular, mammals. "Mammal" comprises, without limitation, mice, rats, rabbits, guinea pigs, dogs, cats, sheep, goats, cows, horses, primates, such as monkeys, chimpanzees, and apes, and, in particular, humans. In some alternative, the subject is human.

In some embodiments, an effective amount of a ligand used for inducing dimerization is an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

A "marker sequence," as described herein, encodes a protein that is used for selecting or tracking a protein or cell, such as a mammalian cell, that has a protein of interest. In the embodiments described herein, the fusion protein provided can comprise a marker sequence that can be selected in experiments, such as flow cytometry.

"Chimeric receptor" or "chimeric antigen receptor," as used herein refers to a synthetically designed receptor comprising a ligand binding domain of an antibody or other protein sequence that binds to a molecule associated with the disease or disorder and is linked via a spacer domain to one or more intracellular signaling domains of a T-cell or other receptors, such as a costimulatory domain. In some embodiments, a cell, such as a mammalian cell, is manufactured wherein the cell comprises a nucleic acid encoding a fusion protein and wherein the cell comprises a chimeric antigen receptor.

"Cytotoxic T lymphocyte" (CTL), as used herein, refers to a T lymphocyte that expresses CD8 on the surface thereof (e.g., a CD8+ T-cell). In some embodiments, such cells are preferably "memory" T-cells (TM cells) that are antigen-experienced. In some embodiments, a cell for fusion protein secretion is provided. In some embodiments, the cell is a cytotoxic T lymphocyte. "Central memory" T-cell (or "$T_{CM}$") as used herein, refers to an antigen experienced CTL that expresses CD62L, CCR-7 and/or CD45RO on the surface thereof, and does not express or has decreased expression of CD45RA, as compared to naïve cells. In some embodiments, a cell for fusion protein secretion is provided. In some embodiments, the cell is a central memory T-cell ($T_{CM}$). In some embodiments, the central memory cells are positive for expression of CD62L, CCR7, CD28, CD127, CD45RO, and/or CD95, and may have decreased expression of CD54RA, as compared to naïve cells. "Effector memory" T-cell (or "TEM") as used herein refers to an antigen experienced T-cell that does not express or has decreased expression of CD62L on the surface thereof, as compared to central memory cells, and does not express or has a decreased expression of CD45RA, as compared to naïve cell. In some embodiments, a cell for fusion protein secretion is provided. In some embodiments, the cell is an effector memory T-cell. In some embodiments, effector memory cells are negative for expression of CD62L and/or CCR7, as compared to naïve cells or central memory cells, and may have variable expression of CD28 and/or CD45RA.

"Naïve T-cells" as used herein, refers to a non-antigen experienced T lymphocyte that expresses CD62L and/or CD45RA, and does not express CD45RO−, as compared to central or effector memory cells. In some embodiments, a cell, such as a mammalian cell, for fusion protein secretion is provided. In some embodiments, the cell, such as a mammalian cell, is a naïve T-cell. In some embodiments, naïve CD8+ T lymphocytes are characterized by the expression of phenotypic markers of naïve T-cells comprising CD62L, CCR7, CD28, CD127, and/or CD45RA.

"Effector" T-cells as used herein, refers to antigen experienced cytotoxic T lymphocyte cells that do not express or have decreased expression of CD62L, CCR7, and/or CD28, and are positive for granzyme B and/or perforin, as compared to central memory or naïve T-cells. In some embodiments, a cell, such as a mammalian cell, for fusion protein secretion is provided. In some embodiments, the cell, such as a mammalian cell, is an effector T-cell. In some embodiments, the cell, such as a mammalian cell, does not express or have decreased expression of CD62L, CCR7, and/or CD28, and are positive for granzyme B and/or perforin, as compared to central memory or naïve T-cells.

"Epitope" as used herein, refers to a part of an antigen or molecule that is recognized by the immune system comprising antibodies, T-cells, and/or B-cells. Epitopes usually have at least 7 amino acids and can be a linear or a conformational epitope. In some embodiments, a cell, such as a mammalian cell, expressing a fusion protein is provided, wherein the cell further comprises a chimeric antigen receptor. In some embodiments, the chimeric antigen receptor comprises a scFv that can recognize an epitope on a cancer cell. "Isolating," or "purifying" when used to describe the various polypeptides or nucleic acids disclosed herein, refers to a polypeptide or nucleic acid that has been identified and separated and/or recovered from a component of its natural environment. Preferably, the isolated polypeptide or nucleic acid is free of association with all components with which it is naturally associated. Contaminant components of its natural environment are materials that would typically interfere with diagnostic or therapeutic uses for the polypeptide or nucleic acid, and can include enzymes, hormones, and other proteinaceous or non-proteinaceous solutes. In some embodiments, a method is provided wherein the method comprises delivering the nucleic acid of anyone of the embodiments described herein or the expression vector of anyone of the embodiments described herein to a bacterial cell, mammalian cell or insect cell, growing the cell up in a culture, inducing expression of the fusion protein and purifying the fusion protein for treatment.

"Percent (%) amino acid sequence identity" with respect to the CISC sequences identified herein is defined as the percentage of amino acid residues in a candidate sequence that are identical with the amino acid residues in the reference sequence for each of the extracellular binding domain, hinge domain, transmembrane domain, and/or the signaling domain, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, ALIGN-2 or Megalign (DNASTAR) software. Those skilled in the art can determine appropriate parameters for measuring alignment, comprising any algorithms needed to achieve maximal alignment over the full-length of the sequences being compared. For example, % amino acid sequence identity values generated using the WU-BLAST-2 computer program (Altschul et al., Methods in Enzymology, 266:460-480 (1996)) uses several search parameters, most of which are set to the default values. Those that are not set to default values (e.g., the adjustable parameters) are set with the following values: overlap span=1, overlap fraction=0.125, word threshold (T)=11 and scoring matrix=BLOSUM62. In some embodiments of the CISC, the CISC comprises an extracellular binding domain, a hinge domain, a transmembrane domain, and a signaling domain, wherein each domain comprises a natural, synthetic, or a mutated or truncated form of the native domain. In some embodiments, a mutated or truncated form of any given domain comprises an amino acid sequence with 100%, 95%, 90%, 85% sequence identity, or a percent sequence identity that is within a range defined by any two of the aforementioned percentages to a sequence set forth in a sequence provided herein.

"CISC variant polypeptide sequence" or "CISC variant amino acid sequence" as used herein refers to a protein sequence as defined below having at least 80%, 85%, 90%, 95%, 98% or 99% amino acid sequence identity (or a percentage amino acid sequence identity within a range defined by any two of the aforementioned percentages) with the protein sequences provided herein, or a specifically derived fragment thereof, such as protein sequence for an extracellular binding domain, a hinge domain, a transmembrane domain and/or a signaling domain. Ordinarily, a CISC variant polypeptide or fragment thereof will have at least 80% amino acid sequence identity, more preferably at least 81% amino acid sequence identity, more preferably at least 82% amino acid sequence identity, more preferably at least 83% amino acid sequence identity, more preferably at least 84% amino acid sequence identity, more preferably at least 85% amino acid sequence identity, more preferably at least 86% amino acid sequence identity, more preferably at least 87% amino acid sequence identity, more preferably at least 88% amino acid sequence identity, more preferably at least 89% amino acid sequence identity, more preferably at least 90% amino acid sequence identity, more preferably at least 91% amino acid sequence identity, more preferably at least 92% amino acid sequence identity, more preferably at least 93% amino acid sequence identity, more preferably at least 94% amino acid sequence identity, more preferably at least 95% amino acid sequence identity, more preferably at least 96% amino acid sequence identity, more preferably at least 97% amino acid sequence identity, more preferably at least 98% amino acid sequence identity and yet more preferably at least 99% amino acid sequence identity with the amino acid sequence or a derived fragment thereof. Variants do not encompass the native protein sequence.

T-cells" or "T lymphocytes" as used herein can be from any mammalian, preferably primate, species, comprising monkeys, dogs, and humans. In some embodiments, the T-cells are allogeneic (from the same species but different donor) as the recipient subject; in some embodiments the T-cells are autologous (the donor and the recipient are the same); in some embodiments the T-cells arc syngeneic (the donor and the recipients are different but are identical twins).

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "comprising at least." When used in the context of a process, the term "comprising" means that the process comprises at least the recited steps, but may include additional steps. When used in the context of a compound, composition or device, the term "comprising" means that the compound, composition or device comprises at least the recited features or components, but may also include additional features or components.

Protein Sequences

Figure 2:
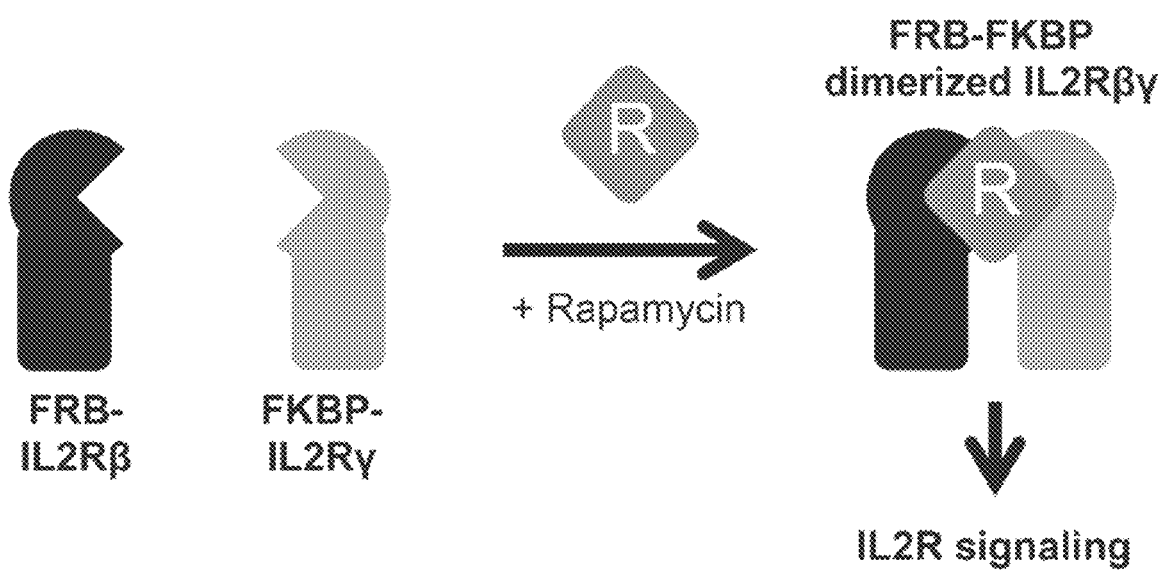
FIG. 2 schematically depicts the cell expansion strategy by a chemical-induced signaling complex (CISC). This strategy utilizes rapamycin's ability to bind two different protein motifs (FKBP and FRB) simultaneously, to induce protein dimerization and active downstream signaling events in an appropriately designed pair of CISC components. The use of a CISC in this manner allows for selective cellular expansion.

As described herein, one or more protein sequence encoding a dimeric CISC component is provided. The one or more protein sequence can have a first and a second sequence. In some embodiments, a first sequence encodes a first CISC component that can comprise a first extracellular binding domain or portion thereof, a hinge domain, a transmembrane domain, and a signaling domain or portion thereof. In some embodiments, a second sequence encodes a second CISC component that can comprise a second extracellular binding domain or a portion thereof, a hinge domain, a transmembrane domain, and a signaling domain or portions thereof. In some embodiments, the first and second CISC components may be positioned such that when expressed, they dimerize in the presence of a ligand, preferably simultaneously. Embodiments of the chemical induced signaling complex are schematically depicted in FIGS. 1-2, which also depict downstream signaling pathways as a result of activation of the CISC, which may include, for example, the RAS/MAPK/ERK signaling pathway, Akt/PI3K signaling pathway, the mTORC1 signaling pathway, or the FOXP3 signaling pathway. In addition, FIG. 2 schematically depicts IL2R signaling due to FRB-FKBP dimerized IL2Rbg in the presence of a ligand, such as rapamycin or an analogue thereof, as described herein.

Figure 3:
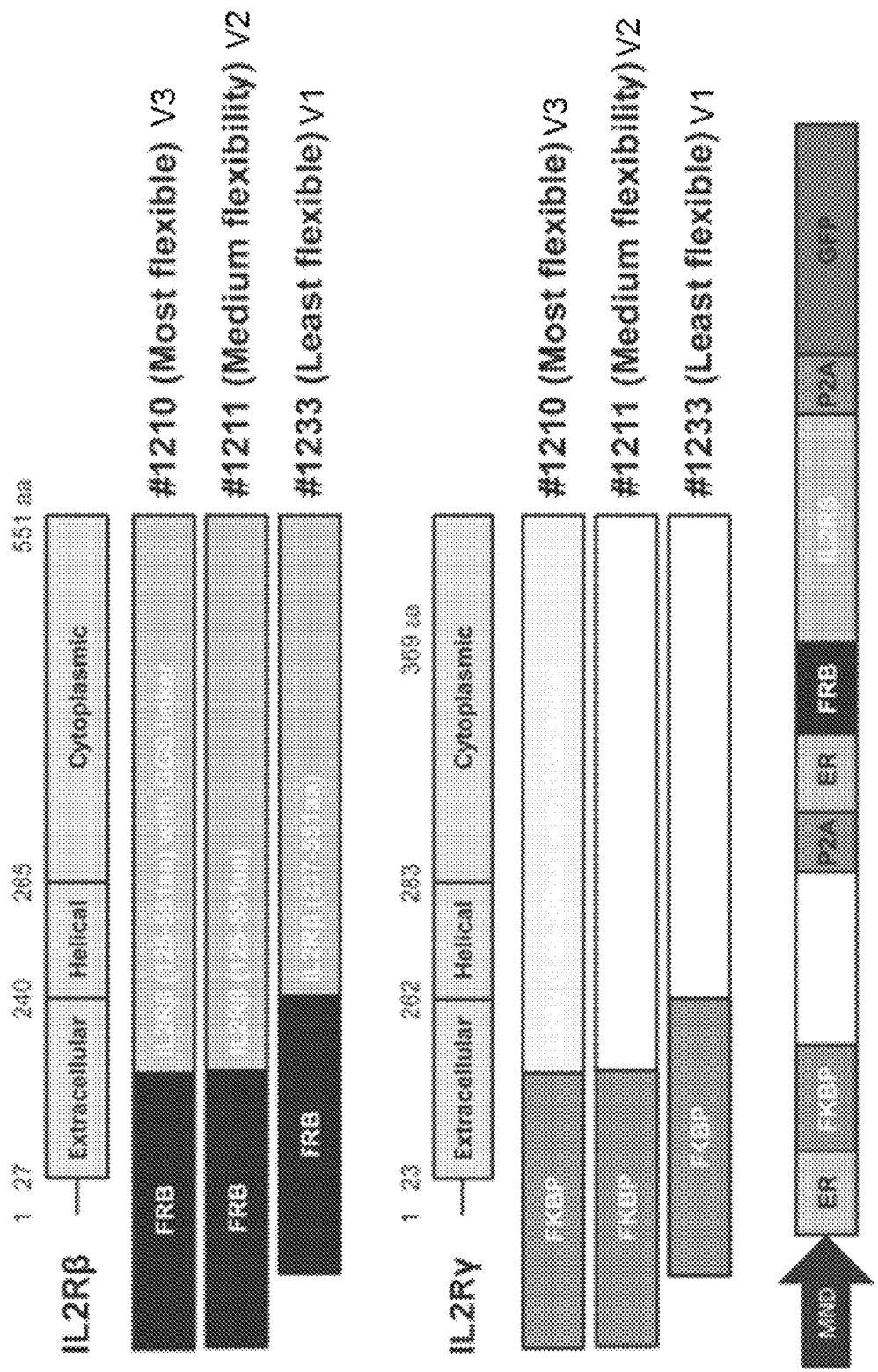
FIG. 3 depicts various embodiments of IL2R-CISC architectures. The embodiment shown in FIG. 3 shows an architecture for both FRB-IL2Rβ and for FKBP-IL2Rγ, providing schematics for various degrees of flexibility, comprising most flexible (1210—this embodiment incorporates a short linker sequence the entire first extracellular immunoglobulin superfamily (IgSF) domain of the IL2R and its TM and cytosolic tail regions), medium flexibility (1211—this embodiment incorporates the entire first extracellular IgSF domain of the IL2R and its TM and cytosolic tail regions), and least flexible (1233—this embodiment incorporates only the IL2R TM and cytosolic tail regions).

In some embodiments, a protein sequence or sequences for heterodimeric two component CISC are provided. In some embodiments, the first CISC component is an IL2Rγ-CISC complex. FIG. 3 schematically depicts the CISC construct design, including CISC having varying amino acid sequence lengths extending from the transmembrane spans. The varying amino acid sequence lengths may confer varied degrees of flexibility, as described herein, and as shown schematically in FIG. 3. The schematics depicted in FIG. 3 may be encompassed by the following sequences, which provide details of the schematic constructs by way of example, and are not intended to be limiting in scope.

In some embodiments, the IL2Rγ-CISC comprises an amino acid sequence as set forth in SEQ ID NO: 1 (MPLGLLWLGLALLGAL-HAQAGVQVETISPGDGRTFPKRGQTCVVHYTGMLE DGK KFDSSRDRNKPFKFMLGKQEVIR-GWEEGVAQMSVGQRAKLTISPDYAYGATGHPGI IPPHATLVFDVELLKLGEGSNTSKENPFLFALEAV-VISVGSMGLIISLLCVYFWLERT MPRIPTLKN-LEDLVTEYHGNFSAWSGVSKGLAESLQPDYSER-LCLVSEIPPKGGALG EGPGASPCNQHSPYWAPPCYTLKPET; SEQ ID NO: 1). Embodiments also comprise a nucleic acid sequence encoding the protein sequence of SEQ ID NO: 1.

In some embodiments, the IL2Rγ-CISC comprises an amino acid sequence as set forth in SEQ ID NO: 3 (MPLGLLWLGLALLGAL-HAQAGVQVETISPGDGRTFPKRGQTCVVHYTGMLE DGK KFDSSRDRNKPFKFMLGKQEVIR-GWEEGVAQMSVGQRAKLTISPDYAYGATGHPGI IPPHATLVFDVELLKLEGGGSQNLVIPWAP-ENLTLHKLSESQLELNWNNRFLNHCLE HLVQYRTDWDHSWTE-QSVDYRHKFSLPSVDGQKRYTFRVRSRFN-PLCGSAQHWSE WSHPIHWGSNTSKENPFLFALEAV-VISVGSMGLIISLLCVYFWLERTMPRIPTLKNLE DLVTEYHGNFSAWSGVSKGLAESLQPDYSERLCLV-SEIPPKGGALGEGPGASPCNQH SPYWAPPCYTLK-PET; SEQ ID NO: 3). Embodiments also comprise a nucleic acid sequence encoding the protein sequence of SEQ ID NO: 3.

In some embodiments, the IL2Rγ-CISC comprises an amino acid sequence as set forth in SEQ ID NO: 5 (MPLGLLWLGLALLGAL-HAQAGVQVETISPGDGRTFPKRGQTCVVHYTGMLE DGK KFDSSRDRNKPFKFMLGKQEVIR-GWEEGVAQMSVGQRAKLTISPDYAYGATGHPGI IPPHATLVFDVELLKLEGQNLVIPWAPENLTLHKLS-ESQLELNWNNRFLNHCLEHLV QYRTDWDHSWTE-QSVDYRHKFSLPSVDGQKRYTFRVRSRFN-PLCGSAQHWSEWSH PIHWGSNTSKENPFLFALEAVVISVGSMGLIIS-LLCVYFWLERTMPRIPTLKNLEDLVT EYHGNF-SAWSGVSKGLAESLQPDYSERLCLVSEIPPKGGAL-GEGPGASPCNQHSPYW APPCYTLKPET; SEQ ID NO: 5). Embodiments also comprise a nucleic acid sequence encoding the protein sequence of SEQ ID NO: 5.

In some embodiments, the IL2Rγ-CISC comprises an amino acid sequence as set forth in SEQ ID NO: 7 (MPLGLLWLGLALLGAL-HAQAGVQVETISPGDGRTFPKRGQTCVVHYTGMLE DGK KFDSSRDRNKPFKFMLGKQEVIR-GWEEGVAQMSVGQRAKLTISPDYAYGATGHPGI IPPHATLVFDVELLKLEGGSNTSKENPFLFALEAV-VISVGSMGLIISLLCVYFWLERT MPRIPTLKN-LEDLVTEYHGNFSAWSGVSKGLAESLQPDYSER-LCLVSEIPPKGGALG EGPGASPCNQHSPYWAPPCYTLKPET; SEQ ID NO: 7). Embodiments also comprise a nucleic acid sequence encoding the protein sequence of SEQ ID NO: 7.

In some embodiments, the protein sequence for the first CISC component includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain. In some embodiments, the protein sequence of the first CISC component, comprising the first extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NOs: 1, 3, 5, or 7, or has a sequence identity that is within a range defined by any two of the aforementioned percentages.

In some embodiments, the second CISC component is an IL2Rβ complex. In some embodiments, the IL2Rβ-CISC comprises an amino acid sequence as set forth in SEQ ID NO: 2 (MALPVTALLLPLALLL-HAARPILWHEMWHEGLEEASRLYFGERNVKGMFE-VLEPL HAMMERGPQTLKETSFNQAYGRDLMEA-QEWCRKYMKSGNVKDLLQAWDLYYHV FRRISKGKDTIPWLGHLLVGLSGAFGFIILV-YLLINCRNTGPWLKKVLKCNTPDPSKF FSQLSSEHGGDVQKWLSSPFPSSSFSPGGLAPEIS-PLEVLERDKVTQLLLQQDKVPEP ASLSSNHSLT-SCFTNQGYFFFHLPDALEIEACQVYFTYDPYSEEDP-DEGVAGAPTGSS PQPLQPLSGEDDAYCTFPSRDDLLLFSPSLLGGPSPP-STAPGGSGAGEERMPPSLQER VPRDWDPQPLGPPTPGVPDLVDFQPPPELVLREA-GEEVPDAGPREGVSFPWSRPPGQ GEFRAL-NARLPLNTDAYLSLQELQGQDPTHLV; SEQ ID NO: 2). Embodiments also comprise a nucleic acid sequence encoding the protein sequence of SEQ ID NO: 2.

In some embodiments, the IL2Rβ-CISC comprises an amino acid sequence as set forth in SEQ ID NO: 4 (MALPVTALLLPLALLLHAARPILWHEMWHEGLEE-ASRLYFGERNVKGMFEVLEPL HAMMERGPQTLKETSFNQAYGRDLMEAQEWCR-KYMKSGNVKDLLQAWDLYYHV FRRISKGGSKPFENLRLMAPISLQVVHVETHRCNIS-WEISQASHYFERHLEFEARTLSP GHTWEE-APLLTLKQKQEWI-CLETLTPDTQYEFQVRVKPLQGEFTTWSPWSQPLA FRT KPAALGKDTIPWLGHLLVGLSGAFGFIILV-YLLINCRNTGPWLKKVLKCNTPDPSKFF QLSSEHGGDVQKWLSSPFPSSSFSPGGLAPEISPLEV-LERDKVTQLLLQQDKVPEPAS LSSNHSLT-SCFTNQGYFFFHLPDALEIEACQVYFTYDPYSEEDP-DEGVAGAPTGSSPQ PLQPLSGEDDAYCTFPSRDDLLLFSPSLLGGPSPP-STAPGGSGAGEERMPPSLQERVPR DWDPQPLGPPTPGVPDLVDFQPPPELVLREAGEEVP-DAGPREGVSFPWSRPPGQGEF RALNARLPLNTDAY-LSLQELQGQDPTHLV; SEQ ID NO: 4). Embodiments also comprise a nucleic acid sequence encoding the protein sequence of SEQ ID NO: 4.

In some embodiments, the IL2Rβ-CISC comprises an amino acid sequence as set forth in SEQ ID NO: 6 (MALPVTALLLPLALLL-HAARPILWWHEMWHEGLEEASRLYFGERNVKGM-FEVLEPL HAMMERGPQTLKETSFNQAYGRDLMEA-QEWCRKYMKSGNVKDLLQAWDLYYHV FRRISKKPFENLRLMAPISLQVVHVETHRCNIS-WEISQASHYFERHLEFEARTLSPGHT WEE-APLLTLKQKQEWI-CLETLTPDTQYEFQVRVKPLQGEFTTWSPWSQPLAF RTKPA ALGKDTIPWLGHLLVGLSGAFGFIILV-YLLINCRNTGPWLKKVLKCNTPDPSKFFSQL SSEHGGDVQKWLSSPFPSSSFSPGGLAPEISPLEVLER-DKVTQLLLQQDKVPEPASLSS NHSLT-SCFTNQGYFFFHLPDALEIEACQVYFTYDPYSEEDP-DEGVAGAPTGSSPQPLQ PLSGEDDAYCTFPSRDDLLLFSPSLLGGPSPP-STAPGGSGAGEERMPPSLQERVPRDW DPQPLGPPTPGVPDLVDFQPPPELVLREAGEEVP-DAGPREGVSFPWSRPPGQGEFRAL NARLPLNTDAY-LSLQELQGQDPTHLV; SEQ ID NO: 6). Embodiments also comprise a nucleic acid sequence encoding the protein sequence of SEQ ID NO: 6.

In some embodiments, the IL2Rβ-CISC comprises an amino acid sequence as set forth in SEQ ID NO: 8 (MALPVTALLLPLALLLHAARPILWHEMWHEGLEE-ASRLYFGERNVKGMFEVLEPL HAM-MERGPQTLKETSWLGHLLVGLSGAFGFIILV-YLLINCRNTGPWLKKVLKCNTP DPSKFFSQLSSEHGGDVQKWLSSPFPSSSFSPGGLA-PEISPLEVLERDKVTQLLLQQDK VPEPASLSSNHSLT-SCFTNQGYFFFHLPDALEIEACQVYFTYDPYSEEDP-DEGVAGAP TGSSPQPLQPLSGEDDAYCTFPSRDDLLLF-SPSLLGGPSPPSTAPGGSGAGEERMPPSL QERVPRDWDPQPLGPPTPGVPDLVDFQPPPELVL-REAGEEVPDAGPREGVSFPWSRP PGQGEFRAL-NARLPLNTDAYLSLQELQGQDPTHLV; SEQ ID NO: 8). Embodiments also comprise a nucleic acid sequence encoding the protein sequence of SEQ ID NO: 8.

In some embodiments, the second CISC component is an IL7Rα complex. In some embodiments, the IL7Rα-CISC comprises an amino acid sequence as set forth in SEQ ID NO: 9 (MALPVTALLLPLALLL-HAARPILWHEMWHEGLEEASRLYFGERNVKGMFE-VLEPL HAMMERGPQTLKETSFNQAYGRDLMEA-QEWCRKYMKSGNVKDLLQAWDLYYHV FRRISKGEINNSSGEMDPILLTISILSFFSVALLVI-LACVLWKKRIKPIVWPSLPDHKKT LEHLCKKPRKNLNVSFNPESFLDCQIHRVD-DIQARDEVEGFLQDTFPQQLEESEKQRL GGDVQSPNCPSEDVVITPESFGRDSSLTCLAG-NVSACDAPILSSSRSLDCRESGKNGP HVYQDLLLSLGTTN-STLPPPFSLQSGILTLNPVAQGQPILTSLGSNQEEAY-VTMSSFY QNQ; SEQ ID NO: 9). Embodiments also comprise a nucleic acid sequence encoding the protein sequence of SEQ ID NO: 9.

In some embodiments, the protein sequence for the second CISC component includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain of the second CISC component. In some embodiments, the protein sequence of the second CISC component, comprising the second extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NOs: 2, 4, 6, 8, or 9, or has a sequence identity that is within a range defined by any two of the aforementioned percentages.

In some embodiments, the protein sequence may include a linker. In some embodiments, the linker comprises 1, 2, 3, 4, 5, 6, 7, 8, 9 or 10 amino acids, such as glycines, or a number of amino acids, such as glycine, within a range defined by any two of the aforementioned numbers. In some embodiments, the glycine spacer comprises at least 3 glycines. In some embodiments, the glycine spacer comprises a sequence set forth in SEQ ID NO: 15 (GGGS; SEQ ID NO: 15), SEQ ID NO: 16 (GGGSGGG; SEQ ID NO: 16) or SEQ ID NO: 17 (GGG; SEQ ID NO: 17). Embodiments also comprise a nucleic acid sequence encoding SEQ ID NOs: 15-17. In some embodiments, the transmembrane domain is located N-terminal to the signaling domain, the hinge domain is located N-terminal to the transmembrane domain, the linker is located N-terminal to the hinge domain, and the extracellular binding domain is located N-terminal to the linker.

In some embodiments, a protein sequence or sequences for homodimeric two component CISC are provided. In some embodiments, the first CISC component is an IL2Rγ-CISC complex. In some embodiments, the IL2Rγ-CISC comprises an amino acid sequence as set forth in SEQ ID NO: 11 (MPLGLLWLGLALLGAL-HAQAGVQVETISPGDGRTFPKRGQTCVVHYTGML EDGK KVDSSRDRNKPFKFMLGKQEVIR-GWEEGVAQMSVGQRAKLTISPDYAYGATGHPGI IPPHATLVFDVELLKLEGGSNTSKENPFLFALEAV-VISVGSMGLIISLLCVYFWLERT MPRIPTLKN-LEDLVTEYHGNFSAWSGVSKGLAESLQPDYSER-LCLVSEIPPKGGALG EGPGASPCNQHSPYWAPPCYTLKPET; SEQ ID NO: 11). Embodiments also comprise a nucleic acid sequence encoding the protein sequence of SEQ ID NO: 11.

In some embodiments, the protein sequence for the first CISC component includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain. In some embodiments, the protein sequence of the first CISC component, comprising the first extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NOs: 11 or has a sequence identity that is within a range defined by any two of the aforementioned percentages.

In some embodiments, the second CISC component is an IL2Rβ complex or an IL2Ra complex. In some embodiments, the IL2Rβ-CISC comprises an amino acid sequence as set forth in SEQ ID NO: 10 (MPLGLLWLGLALLGAL-HAQAGVQVETISPGDGRTFPKRGQTCVVHYTGMLE DGK KVDSSRDRNKPFKFMLGKQEVIR-GWEEGVAQMSVGQRAKLTISPDYAYGATGHPGI IPPHATLVFDVELLKLEGGKDTIPWLGHLLL-VGLSGAFGFIILVYLLINCRNTGPWLKK VLKCNTPDPSKFF-SQLSSEHGGDVQKWLSSPFPSSSFSPGGLAPEISPLEV-LERDKVTQ LLLQQDKVPEPASLSSNHSLT-SCFTNQGYFFFHLPDALEIEACQVYFTYDPYSEEDPD EGVAGAPTGSSPQPLQPLSGEDDAYCTFPSRDDLLLF-SPSLLGGPSPPSTAPGGSGAG EERM-PPSLQERVPRDWDPQPLGPPTPGVPDLVDFQPPPEL-VLREAGEEVPDAGPREG VSFPWSRPPGQGEFRALNARLPLNTDAY-LSLQELQGQDPTHLV; SEQ ID NO: 10). Embodiments also comprise a nucleic acid sequence encoding the protein sequence of SEQ ID NO: 10.

In some embodiments, the IL2Rα-CISC comprises an amino acid sequence as set forth in SEQ ID NO: 12 (MPLGLLWLGLALLGAL-HAQAGVQVETISPGDGRTFPKRGQTCVVHYTGMLE DGK KVDSSRDRNKPFKFMLGKQEVIR-GWEEGVAQMSVGQRAKLTISPDYAYGATGHPGI IPPHATLVFD-VELLKLEGEINNSSGEMDPILLTISILSFFSVALLVI-LACVLWKKRIKPIV WPSLPDHKKTLEHLCKKPRKNLNVSFNPESFLDCQI HRVDDIQARDEVEGFLQDTFP QQLEESEKQRLGGDVQSPNCPSEDVVIT-PESFGRDSSLTCLAGNVSACDAPILSSSRSL DCRESGKNGPHVYQDLLLSLGTTN-STLPPPFSLQSGILTLNPVAQGQPILTSLGSNQEE AYVTMSSFYQNQ; SEQ ID NO: 12). Embodiments also comprise a nucleic acid sequence encoding the protein sequence of SEQ ID NO: 12.

In some embodiments, the protein sequence for the second CISC component includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain of the second CISC component. In some embodiments, the protein sequence of the second CISC component, comprising the second extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NO: 10 or SEQ ID NO: 12, or has a sequence identity that is within a range defined by any two of the aforementioned percentages.

In some embodiments, the protein sequence may include a linker. In some embodiments, the linker comprises 1, 2, 3, 4, 5, 6, 7, 8, 9 or 10 amino acids, such as glycines, or a number of amino acids, such as glycine, within a range defined by any two of the aforementioned numbers. In some embodiments, the glycine spacer comprises at least 3 glycines. In some embodiments, the glycine spacer comprises a sequence set forth in SEQ ID NO: 15 (GGGS; SEQ ID NO: 15), SEQ ID NO: 16 (GGGSGGG; SEQ ID NO: 16) or SEQ ID NO: 17 (GGG; SEQ ID NO: 17). Embodiments also comprise a nucleic acid sequence encoding SEQ ID NOs: 15-17. In some embodiments, the transmembrane domain is located N-terminal to the signaling domain, the hinge domain is located N-terminal to the transmembrane domain, the linker is located N-terminal to the hinge domain, and the extracellular binding domain is located N-terminal to the linker.

In some embodiments, the sequences for the homodimerizing two component CISC incorporate FKBP F36V domain for homodimerization with the ligand AP1903.

In some embodiments is provided a protein sequence or sequences for single component homodimerization CISC. In some embodiments, the single component CISC is an IL7Rα-CISC complex. In some embodiments, the IL7Rα-CISC comprises an amino acid sequence as set forth in SEQ ID NO: 13 (MPLGLLWLGLALLGAL-HAQAGVQVETISPGDGRTFPKRGQTCVVHYTGMLE DGK KVDSSRDRNKPFKFMLGKQEVIR-GWEEGVAQMSVGQRAKLTISPDYAYGATGHPGI IPPHATLVFD-VELLKLEGEINNSSGEMDPILLTISILSFFSVALLVI-LACVLWKKRIKPIV WPSLPDHKKTLEHLCKKPRKNLNVSFNPESFLDCQI HRVDDIQARDEVEGFLQDTFP QQLEESEKQRLGGDVQSPNCPSEDVVIT-PESFGRDSSLTCLAGNVSACDAPILSSSRSL DCRESGKNGPHVYQDLLLSLGTTN-STLPPPFSLQSGILTLNPVAQGQPILTSLGSNQEE AYVTMSSFYQNQ; SEQ ID NO: 13). Embodiments also comprise a nucleic acid sequence encoding the protein sequence of SEQ ID NO: 13.

In some embodiments, the single component CISC is an MPL-CISC complex. In some embodiments, the MPL-CISC comprises an amino acid sequence as set forth in SEQ ID NO: 14 (MPLGLLWLGLALLGAL-HAQAGVQVETISPGDGRTFPKRGQTCVVHYTGMLE DGK KVDSSRDRNKPFKFMLGKQEVIR-GWEEGVAQMSVGQRAKLTISPDYAYGATGHPGI IPPHATLVFDVELLKLGEETAWISLVTALHLVLGL-SAVLGLLLLRWQFPAHYRRLRH ALWPSLPDLHRVLGQYLRDTAALSPPKATVSDT-CEEVEPSLLEILPKSSERTPLPLCSS QAQMDYRRLQP-SCLGTMPLSVCPPMAESGSCCTTHIANHSYLPL-SYWQQP; SEQ ID NO: 14). Embodiments also comprise a nucleic acid sequence encoding the protein sequence of SEQ ID NO: 14.

In some embodiments, the protein sequence for the single component CISC includes a protein sequence encoding an extracellular binding domain, a hinge domain, a transmembrane domain, or a signaling domain. Embodiments also comprise a nucleic acid sequence encoding the extracellular binding domain, the hinge domain, the transmembrane domain, or the signaling domain. In some embodiments, the protein sequence of the first CISC component, comprising the first extracellular binding domain, the hinge domain, the transmembrane domain, and/or the signaling domain comprises an amino acid sequence that comprises a 100%, 99%, 98%, 95%, 90%, 85%, or 80% sequence identity to the sequence set forth in SEQ ID NO: 13 or SEQ ID NO: 14 or has a sequence identity that is within a range defined by any two of the aforementioned percentages.

In some embodiments, the protein sequence may include a linker. In some embodiments, the linker comprises 1, 2, 3, 4, 5, 6, 7, 8, 9 or 10 amino acids, such as glycines, or a number of amino acids, such as glycine, within a range defined by any two of the aforementioned numbers. In some embodiments, the glycine spacer comprises at least 3 glycines. In some embodiments, the glycine spacer comprises a sequence set forth in SEQ ID NO: 15 (GGGS; SEQ ID NO: 15), SEQ ID NO: 16 (GGGSGGG; SEQ ID NO: 16) or SEQ ID NO: 17 (GGG; SEQ ID NO: 17). Embodiments also comprise a nucleic acid sequence encoding SEQ ID NOs: 15-17. In some embodiments, the transmembrane domain is located N-terminal to the signaling domain, the hinge domain is located N-terminal to the transmembrane domain, the linker is located N-terminal to the hinge domain, and the extracellular binding domain is located N-terminal to the linker.

In some embodiments, the sequences for the homodimerizing single component CISC incorporate FKBP F36V domain for homodimerization with the ligand AP1903.

Vectors for Expressing the Dimeric CISC Components

A variety of vector combinations can be constructed to provide for efficient transduction and transgene expression. In some embodiments, the vector is a viral vector. In other embodiments, the vectors can include a combination of viral vectors and plasmid vectors. Other viral vectors include foamy virus, adenoviral vectors, adeno-associated viral (AAV) vectors, retroviral vectors, and/or lentiviral vectors. In some embodiments, the vector is a lentiviral vector. In some embodiments, the vector is a foamy viral vector, adenoviral vectors, retroviral vectors or lentiviral vectors. In some embodiments, the vector is for protein expression in a bacterial system, such as E. coli. In other embodiments, a first vector can encode a first CISC component comprising a first extracellular binding domain or portion thereof, a hinge domain, a transmembrane domain, and a signaling domain or portion thereof while a second vector can encode a second CISC component comprising a second extracellular binding domain or a portion thereof, a hinge domain, a transmembrane domain, and a signaling domain or portions thereof.

In some embodiments, the expression vector comprises a nucleic acid encoding the protein sequence of SEQ ID NOs: 1, 2, 3, 4, 5, 6, 7, 8, or 9. In some embodiments, the expression vector comprises a nucleic acid sequence as set forth in SEQ ID NO: 20 (AGCTTAATGTAGTCT-TATGCAATACTCTTGTAGTCTTGCAACATGGTAAC-GATGA GTTAGCAACATGCCTTA-CAAGGAGAGAAAAAGCACCGTGCATGCCGATTGG TGG AAGTAAGGTGGTACGATCGTGCCTTATTAG-GAAGGCAACAGACGGGTCTGACAT GGAT-TGGACGAACCACTGAATTGCCGCATTGCAGAGAT-ATTGTATTTAAGTGCCT AGCTCGATACAATAAACGGGTCTCTCTGGTTA-GACCAGATCTGAGCCTGGGAGC TCTCTGGCTAACTAGGGAACCCACTGCTTAAGCCT-CAATAAAGCTTGCCTTGAGT GCTT-CAAGTAGTGTGTGCCCGTCTGTTGTGTGACTCTGG TAACTAGAGATCCCTC AGACCCTTT-TAGTCAGTGTG-GAAAATCTCTAGCAGTGGCGCCCGAACAGGGACT TGAAAGCGAAAGGGAAACCAGAG-GAGCTCTCTCGACGCAGGACTCGGCTTGCTG AAGCGCGCACGGCAAGAGGCGAGGGGCGGCGAC TGGTGAGTACGCCAAAAATT TTGACTAGCG-GAGGCTAGAAGGAGAGAGATGGGTGCGAGAGCGT CAGTATTAA GCGGGGGAGAATTAGATCGCGATGG-GAAAAAATTCGGTTAAGGCCAGGGGGAA AGAAAAAATATAAATTAAAA-CATATAGTATGGGCAAGCAGGGAGCTAGAACGA TTCGCAGTTAATCCTGGCCTGTTAGAAA-CATCAGAAGGCTGTAGACAAATACTG GGACAGC-TACAACCATCCCTTCAGACAGGATCAGAAGAACT-TAGATCATTATAT AATACAGTAGCAACCCTCTATTGTGTGCAT-CAAAGGATAGAGATAAAAGACACC AAGGAAGCTT-TAGACAAGATAGAG-GAAGAGCAAAACAAAAGTAAGACCACCGC ACAGCAAGCGGCCGCTGATCTTCAGACCTGGAG-GAGGAGATATGAGGGACAATT GGAGAAGTGAAT-TATATAAATATAAAGTAGTAAAAATTGAACCATTAG-GAGTAG CACCCAC-CAAGGCAAAGAGAAGAGTGGTGCAGAGAGAAAA AAGAGCAGTGGGA ATAG-GAGCTTTGTTCCTTGGGTTCTTGGGAGCAGCAG-GAAGCACTATGGGCGCA GCCT-CAATGACGCTGACGGTACAGGCCAGACAATTATTG TCTGGTATAGTGCAG CAGCAGAACAATTTGCT-GAGGGCTATTGAGGCGCAACAG-CATCTGTTGCAACTC ACAGTCTGGGGCAT-CAAGCAGCTCCAGGCAAGAATCCTGGCTGTGGAA AGATAC CTAAAGGATCAACAGCTCCTGGGGAT-TTGGGGTTGCTCTGGAAAACTCATTTGCA CCACTGCTGTGCCTTGGAATGCTAGTTG-GAGTAATAAATCTCTGGAACAGATTTG GAAT-CACACGACCTGGATGGAGTGGGACAGAGAAAT-TAACAATTACACAAGCTT AATACACTCCTTAATT-GAAGAATCGCAAAACCAGCAAGAAAAGAAT-GAACAAG AATTATTGGAATTAGA-TAAATGGGCAAGTTTGTGGAATTGGTTTAACATAA CAA ATTGGCTGTGGTATATAAAATTATTCATAATGA-TAGTAGGAGGCTTGGTAGGTTT AAGAATAGTTTTTGCTGTACTTTCTATAGT-GAATAGAGTTAGGCAGGGATATTCA CCAT-TATCGTTTCAGACCCACCTCC-CAACCCCGAGGGGACCCGACAGGCCCGAA GGAATAGAAGAAGAAGGTGGAGAGAGAGACAGA-GACAGATCCATTCGATTAGT GAACG-GATCTCGACGGTATCGGTTAACTTT-TAAAAGAAAAGGGGGGATTGGGGG GTACAGTGCAGGGGAAAGAATAGTAGACAT-AATAGCAACAGACATACAAACTA AAGAATTA-CAAAAACAAATTACAAAAATTCAAAATTTTATC-GATCACGAGACTA GCCTCGAGAAGCTTGATATCGAATTCC-CACGGGGTTGGACGCGTAGGAACAGAG AAACAG-GAGAATATGGGCCAAACAGGA-TATCTGTGGTAAGCAGTTCCTGCCCCG GCTCAGGGCCAAGAACAGTTG-GAACAGCAGAATATGGGCCAAACAGGATATCTG TGGTAAGCAGTTCCTGCCCCGGCTCAGGGC-CAAGAACAGATGGTCCCCAGATGC GGTCCCGCCCTCAGCAGTTTCTAGAGAACCATCA-GATGTTTCCAGGGTGCCCCAA GGACCT-GAAATGACCCTGTGCCTTATTTGAACTAAC-CAATCAGTTCGCTTCTCGC TTCTGTTCGCGCGCTTCTGCTCCCCGAGCTC-TATATAAGCAGAGCTCGTTTAGTG AACCGTCA- GATCGCTAGCACCGGTGCCGCCACCATGCCTCTGGGCCTGCTGTGGCTGGGCCTGGCCCTGCTGGGCGCCCTGCACGCCCAGGCCGGCGTGCAGGTGGAGACAATCTCCCCAGGCGACGGACGCACATTCCCTAAGCGGGGCCAGACCTGCGTGG TGCACTATACAGGCATGCTGGAGGATGGCAAGAAGTTTGACAGCTCCCGGGATAGAAACAAGCCATTCAAGTTTATGCTGGGCAAGCAGGAAGTGATCAGAGGCTGGG AGGAGGGCGTGGCCCAGATGTCTGTGGGCCAGAGGGCCAAGCTGACCATCAGCC CAGACTACGCCATGGAGCAACAGGCCACCCAGGAATCATCCCACCTCACGCCACCCTGGTGTTCGATGTGGAGCTGCTGAAGCTGGGCGAGGGATCCAACACATCAAAAGAGAACCCCTTTCTGTTCGCATTGGAGGCCGTAGTCATATCTGTTGGATCCAT GGGACTTATTATCTCCCTGTTGTGTGTGTACTTCTGGCTGAACGGACTATGCCCAGGATCCCCACGCTCAAGAATCTGGAAGATCTCGTCACAGAATACCATGGTAAT TTCAGCGCCTGGAGCGGAGTCTCTAAGGGTCTGGCCGAATCCCTCCAACCCGATT ATTCTGAACGGTTGTGCCTCGTATCCGAAATACCACCAAAAGGCGGGGCTCTGG GTGAGGGCCCAGGGGCGAGTCCGTGCAATCAACACAGCCCGTATTGGGCCCCTC CTTGTTATACGTTGAAGCCCGAAACTGGAAGCGGAGCTACTAACTTCAGCCTGCT GAAGCAGGCTGGAGACGTGGAGGAGAACCCTGGACCTATGGCACTGCCCGTGACCGCCCTGCTGCTGCCTCTGGCCCTGCTGCTGCACGCAGCCCGGCCTATCCTGTGGCACGAGATGTGGCACGAGGGCCTGGAGGAGGCCAGCAGGCTGTATTTTGGCGAG CGCAACGTGAAGGGCATGTTCGAGGTGCTGGAGCCTCTGCACGCCATGATGGAG AGAGGCCCACAGACCCTGAAGGAGACATCCTTTAACCAGGCCATGGACGGGAC CTGATGGAGGCACAGGAGTGGTGCAGAAAGTACATGAAGTCTGGCAATGTGAAG GACCTGCTGCAGGCCTGGGATCTGTACTATCACGTGTTTCGGAGAATCTCCAAGG GCAAAGACACGATTCCGTGGCTTGGGCATCTGCTCGTTGGGCTGAGTGGTGCGTT TGGTTTCATCATCTTGGTCTATCTCTTGATCAATTGCAGAAATACAGGCCCTTGGC TGAAAAAAGTGCTCAAGTGTAATACCCCCGACCCAAGCAAGTTCTTCTCCCAGCT TTCTTCAGAGCATGGAGGCGATGTGCAGAAATGGCTCTCTTCACCTTTTCCCTCC TCAAGCTTCTCCCCGGGAGGGCTGGCGCCCGAGATTTCACCTCTTGAGGTACTTG AACGAGACAAGGTTACCCAACTTCTCCTTCAACAGGATAAGGTACCCGAACCTG CGAGCCTTAGCTCCAACCACTCTCTTACGAGCTGCTTCACCAATCAGGGATACTTCTTTTTCCACCTTCCCGATGCGCTGGAAATCGAAGCTTGTCAAGTTTACTTTACCTATGATCCATATAGCGAGGAAGATCCCGACGAAGGAGTCGCCGGTGCGCCCACGGGTTCCTCACCCCAACCTCTCCAGCCTCTCTCAGGAGAAGATGATGCTTATTGCAC TTTTCCCAGTAGAGACGATCTCCTCCTCTTTTCTCCATCTCTTTTGGGGGGACCTTCCCCCCCTTCTACGGCACCTGGCGGGTCTGGTGCTGGCGAGGAGCGGATGCCGC CGTCCCTCCAGGAGCGAGTACCACGAGATTGGGATCCCCAGCCACTTGGACCCCCCACCCCCGGCGTACCTGACCTTGTCGATTTTCAACCTCCCCCTGAATTGGTGCTGCGAGAGGCTGGGGAGGAAGTTCCGGACGCTGGGCCGAGGGAGGGCGTGTCCTT TCCATGGAGTAGGCCTCCAGGTCAAGGCGAGTTTAGGGCTCTCAACGCGCGGCT GCCGTTGAATACAGACGCTTATCTCTCACTGCAGGAACTGCAAGGTCAGGACCCAACACATCTTGTAGGATCTGGTGCTACTAATTTTTCTCTTTTGAAGCAAGCTGGA GATGTTGAAGAGAACCCTGGTCCAGTGAGCAAGGGCGAGGAGCTGTTCACCGGGGTGGTGCCCATCCTGGTCGAGCTGGACGGCGACGTAAACGGCCACAAGTTCAGC GTGTCCGGCGAGGGCGAGGGCGATGCCACCTACGGCAAGCTGACCCTGAAGTTCATCTGCACCACCGGCAAGCTGCCCGTGCCCTGGCCCACCCTCGTGACCACCCTGACCTACGGCGTGCAGTGCTTCAGCCGCTACCCCGACCACATGAAGCAGCACGACT TCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCC TGGTGAACCGCATCGAGCTGAAGGGCATCGACTTCAAGGAGGACGGCAACATCC TGGGGCACAAGCTGGAGTACAACTACAACAGCCACAACGTCTATATCATGGCCG ACAAGCAGAAGAACGGCATCAAGGTGAACTTCAAGATCCGCCACAACATCGAG GACGGCAGCGTGCAGCTCGCCGACCACTACCAGCAGAACACCCCCATCGGCGAC GGCCCCGTGCTGCTGCCCGACAACCACTACCTGAGCACCCAGTCCGCCCTGAGC AAAGACCCCAACGAGAAGCGCGATCACATGGTCCTGCTGGAGTTCGTGACCGCC GCCGGGATCACTCTCGGCATGGACGAGCTGTACAAGTAAACTAGTGTCGACAAT CAACCTCTGGATTACAAAATTTGTGAAAGATTGACTGGTATTCTTAACTATGTTG CTCCTTTTACGCTATGTGGATACGCTGCTTTAATGCCTTTGTATCATGCTATTGCT TCCCGTATGGCTTTCATTTTCTCCTCCTTGTATAAATCCTGGTTGCTGTCTCTTTAT GAGGAGTTGTGGCCCGTTGTCAGGCAACGTGGCGTGGTGTGCACTGTGTTTGCTG ACGCAACCCCCACTGGTTGGGGCATTGCCACCACCTGTCAGCTCCTTTCCGGGAC TTTCGCTTTCCCCCTCCCTATTGCCACGGCGGAACTCATCGCCGCCTGCCTTGCCC GCTGCTGGACAGGGGCTCGGCTGTTGGGCACTGACAATTCCGTGGTGTTGTCGGG AAGCTGACGTCCTTTCCATGGCTGCTCGCCTGTGTTGCCACCTGGATTCTGCGC GGGACGTCCTTCTGCTACGTCCCTTCGGCCCTCAATCCAGCGGACCTTCCTTCCC GCGGCCTGCTGCCGGCTCTGCGGCCTCTTCCGCGTCTTCGCCTTCGCCCTCAGAC GAGTCGGATCTCCCTTTGGGCCGCCTCCCCGCCTGGAATTCGAGCTCGGTACCTT TAAGACCAATGACTTACAAGGCAGCTGTAGATCT TAGCCACTTTTTAAAAGAAA AGGGGGGACTGGAAGGGCTAATTCACTCCCAACGAAGACAAGATCTGCTTTTTG
CTTGTACTGGGTCTCTCTGGTTAGACCAGATCTGAGCCTGGGAGCTCTCTGGCTA ACTAGGGAACCCACTGCTTAAGCCTCAATAAAGCTTGCCTTGAGTGCTTCAAGTA
GTGTGTGCCCGTCTGTTGTGTGACTCTGGTAACTAGAGATCCCTCAGACCCTTTT AGTCAGTGTGGAAAATCTCTAGCAGTAGTAGTTCATGTCATCTTATTATTCAGTA TTTATAACTTGCAAAGAAATGAATATCAGAGAGTGAGAGGAACTTGTTATTGCAGCTTATAATGGTTACAAATAAAGCAATAGCATCACAAATTTCACAAATAAAGC ATTTTTTTCACTGCATTCTAGTTGTGGTTTGTCCAAACTCATCAATGTATCTTATC
ATGTCTGGCTCTAGCTATCCCGCCCCTAACTCCGCCCAGTTCCGCCCATTCTCCGC CCCATGGCTGACTAATTTTTTTATTTATGCAGAGGCCGAGGCCGCCTCGGCCTC
TGAGCTATTCCAGAAGTAGTGAGGAGGCTTTTTTGGAGGCCTAGGCTTTTGCGTC GAGACGTACCCAATTCGCCCTATAGTGAGTCGTATTACGCGCGCTCACTGGCCGT
CGTTTTACAACGTCGTGACTGGGAAAACCCTGGCGTTACCCAACTTAATCGCCTT GCAGCACATCCCCCTTTCGCCAGCTGGCGTAATAGCGAAGAGGCCCGCACCGAT CGCCCTTCCAACAGTTGCGCAGCCTGAATGGCGAATGGCGCGACGCGCCCTGT
AGCGGCGCATTAAGCGCGGCGGGTGTGGTGGTTACGCGCAGCGTGACCGCTACA
CTTGCCAGCGCCCTAGCGCCCGCTCCTTTCGCTTTCTTCCCTTCCTTTCTCGCCAC
GTTCGCCGGCTTTCCCCGTCAAGCTCTAAATCGGGGGCTCCCTTTAGGGTTCCGA TTTAGTGCTTTACGGCACCTCGACCCCAAAAAACTTGATTAGGGT
GATGGTTCAC GTAGTGGGCCATCGCCCTGATAGACGGTTTTTCGCCCTTTGACGTTGGAGTCCAC
GTTCTTTAATAGTGGACTCTTGTTCCAAACTGGAACAACACTCAACCCTATCTCG GTCTATTCTTTTGATTTATAAGGGATTTTGCCGATTTCGGCCTATTGGTTAAAAAA
TGAGCTGATTTAACAAAAATTTAACGCGAATTTTAACAAAATATTAACGTTTACA
ATTTCCCAGGTGGCACTTTTCGGGGAAATGTGCGCGGAACCCCTATTTGTTTATT
TTTCTAAATACATTCAAATATGTATCCGCTCATGAGACAATAACCCTGATAAATG CTTCAATAATATTGAAAAAGGAAGAGTATGAGTATTCAACATTTCCGTGTCGCCC
TTATTCCCTTTTTTGCGGCATTTTGCCTTCCTGTTTTTGCTCACCCAGAAACGCTG
GTGAAAGTAAAAGATGCTGAAGATCAGTTGGGTGCACGAGTGGGTTACATCGAA
CTGGATCTCAACAGCGGTAAGATCCTTGAGAGTTTTCGCCCCGAAGAACGTTTTC CAATGATGAGCACTTTTAAAGTTCTGCTATGTGGCGCGGTATTATCCCGTATTGA
CGCCGGGCAAGAGCAACTCGGTCGCCGCATACACTATTCTCAGAATGACTTGGT TGAGTACTCACCAGTCACAGAAAAGCATCTTACGGATGGCATGACAGTAAGAGA
ATTATGCAGTGCTGCCATAACCATGAGTGATAACACTGCGGCCAACTTACTTCTG ACAACGATCG GAGGACCGAAGGAGCTAACCGCTTTTTTGCACAACATGGGGGAT
CATGTAACTCGCCTTGATCGTTGGGAACCGGAGCTGAATGAAGCCATACCAAAC GACGAGCGTGACACCACGATGCCTGTAGCAATGGCAACAACGTTGCGCAAACTA
TTAACTGGCGAACTACTTACTCTAGCTTCCCGGCAACAATTAATAGACTGGATGG AGGCGGATAAAGTTGCAGGACCACTTCTGCGCTCGGCCCTTCCGGCTGGCTGGTT
TATTGCTGATAAATCTGGAGCCGGTGAGCGTGGGTCTCGCGGTATCATTGCAGCA CTGGGGCCAGATGGTAAGCCCTCCCGTATCGTAGTTATCTACACGACGGGGAGT CAGGCAACTATGGATGAACGAAATAGACAGATCGCTGAGATAGGTGCCTCACTG
ATTAAGCATTGGTAACTGTCAGACCAAGTTTACTCATATATACTTTAGATTGATT TAAAACTTCATTTTTAATTTAAAAGGATCTAGGTGAAGATCCTTTTTGATAATCTC
ATGACCAAAATCCCTTAACGTGAGTTTTCGTTCCACTGAGCGTCAGACCCCGTAG AAAAGATCAAAGGATCTTCTT
GAGATCCTTTTTTTCTGCGCGTAATCTGCTGCTTGCAAACAAAAAAACCACCGCTACCAGCGGTGGTTTGTTTGCCGGATCAAGAGCTACCAACTCTTTTTCCGAAGGTAACTGGCTTCAGCAGAGCGCAGATACCAAATACTG
TCCTTCTAGTGTAGCCGTAGTTAGGCCACCACTTCAAGAACTCTGTAGCACCGCC TACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGG TCGGGCTGAACGGGGGGTTCGTGCACACAGCCCAGCTTGGAGCGAACGACCTAC
ACCGAACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGAGCG CACGAGGGAGCTTCCAGGGGGAAACGCCTGGTATCTTTATAGTCCTGTCGGGTTT CGCCACCTCTGACTTGAGCGTCGATTTTTGTGATGCTCGTCAGGGGGGCG
GAGCC TATGGAAAAACGCCAGCAACGCGGCCTTTTTACGGTTCCTGGCCTTTTGCTGGCC TTTTGCTCACATGTTCTTTCCTGCGTTATCCCCTGATTCTGTGGA
TAACCGTATTA CCGCCTTTGAGTGAGCTGATACCGCTCGCCGCAGCCGAACGACCGAGCGCAGCG AGTCAGTGAGCGAGGAAGCGGAAGAGCGCCCAATACGCAAACCGCCTCTCCCCG CGCGTTGGCCGATTCATTAATGCAGCTGGCACGACAGGTTTCCCGACTGGA
AAG CGGGCAGTGAGCGCAACGCAATTAATGTGAGTTAGCTCACTCATTAGGCACCCC AGGCTTTACACTTTATGCTTCCGGCTCGTATGTTGTGTGGAATTGTGAGCGGATA
ACAATTTCACACAGGAAACAGCTATGACCATGATTACGCCAAGCGCGCAATTAA CCCTCACTAAAGGGAACAAAAGCTGGAGCTGCA; SEQ ID NO: 20). SEQ ID NO: 20 encodes the protein sequences as set forth in SEQ ID NOs: 7 and 8.

In some embodiments, the expression vector is a variant of SEQ ID NO: 20 as set forth in SEQ ID NO: 18 (AGCTTAATGTAGTCTTATGCAATACTCTTGTAGTCTTGCAACATGGTAAC- GATGA GTTAGCAACATGCCTTACAAGGAGAGAAAAAGCACCGTGCATGCCGATTGG TGG AAGTAAGGTGGTACGATCGTGCCTTATTAGGAAGGCAACAGACGGGTCTGACAT GGATGGACGAACCACTGAATTGCCGCATTGCAGAGATATTGTATTTAAGTGCCT
AGCTCGATACAATAAACGGGTCTCTCTGGTTAGACCAGATCTGAGCCTGGGAGC
TCTCTGGCTAACTAGGGAACCCACTGCTTAAGCCTCAATAAAGCTTGCCTTGAGT GCTTCAAGTAGTGTGTGCCCGTCTGTTGTGTGACTCTGG TAACTAGAGATCCCTC AGACCCTTTTAGTCAGTGTG
GAAAATCTCTAGCAGTGGCGCCCGAACAGGGACT TGAAAGCGAAAGGGAAACCAGAGGAGCTCTCTCGACGCAGGACTCGGCTTGCTG AAGCGCGCACGGCAAGAGGCGAGGGGCGGCGAC TGGTGAGTACGCCAAAAATT TTGACTAGCGGAGGCTAGAAGGAGAGAGATGGGTGCGAGAGCGT CAGTATTAA GCGGGGGAGAATTAGATCGCGATGGGAAAAAATTCGGTTAAGGCCAGGGGAA AGAAAAAATATAAATTAAAACATATAGTATGGGCAAGCAGGGAGCTAGAACGA TTCGCAGTTAATCCTGGCCTGTTAGAAACATCAGAAGGCTGTAGACAAATACTG GGACAGCTACAACCATCCCTTCAGACAGGATCAGAAGAACTTAGATCATTATAT
AATACAGTAGCAACCCTCTATTGTGTGCATCAAAGGATAGAGATAAAAGACACC AAGGAAGCTTTAGACAAGATAGAGGAAGAGCAAAACAAAAGTAAGACCACCGC ACAGCAAGCGGCCGCTGATCTTCAGACCTGGAGGAGGAGATATGAGGGACAATT GGAGAAGTGAATTATATAAATATAAAGTAGTAAAAATTGAACCATTAGGAGTAG
CACCCACCAAGGCAAAGAGAAGAGTGGTGCAGAGAGAAAA AAGAGCAGTGGGA ATAGGAGCTTTGTTCCTTGGGTTCTTGGGAGCAGCAGGAAGCACTATGGGCGCA GCCTCAATGACGCTGACGGTACAGGCCAGACAATTATTG TCTGGTATAGTGCAG CAGCAGAACAATTTGCTGAGGGCTATTGAGGCGCAACAGCATCTGTTGCAACTC ACAGTCTGGGGCATCAAGCAGCTCCAGGCAAGAATCCTGGCTGTGGAA AGATAC CTAAAGGATCAACAGCTCCTGGGGATTTGGGGTTGCTCTGGAAAACTCATTTGCA CCACTGCTGTGCCTTGGAATGCTAGTTGGAGTAATAAATCTCTGGAACAGATTTG GAATCACACGACCTGGATGGAGTGGGACAGAGAAATTAACAATTACACAAGCTT
AATACACTCCTTAATTGAAGAATCGCAAAACCAGCAAGAAAAGAATGAACAAG AATTATTGGAATTAGATAAATGGGCAAGTTTGTGGAATTGGTTTAACATA ACAA ATTGGCTGTGGTATATAAAATTATTCATAATGATAGTAGGAGGCTTGGTAGGTTT AAGAATAGTTTTTGCTGTACTTTCTATAGTGAATAGAGTTAGGCAGGGATATTCA CCATTATCGTTTCAGACCCACCTCCCAACCCCGAGGGGACCCGACAGGCCCGAA GGAATAGAAGAAGGTGGAGAGAGAGACAGAGACATCCATTCGATTAGT GAACGGATCTCGACGGTATCGGTTAACTTTTAAAAGAAAAGGGGGGATTGGGGG GTACAGTGCAGGGGAAAGAATAGTAGACATAATAGCAACAGACATACAAACTA AAGAATTA CAAAAACAAATTACAAAAATTCAAAATTTTATCGATCACGAGACTA
GCCTCGAGAAGCTTGATATCGAATTCCCACGGGGTTGGACGCGTAGGAACAGAG AAACAGGAGAATATGGGCCAAACAGGATATCTGTGGTAAGCAGTTCCTGCCCCG GCTCAGGGCCAAGAACAGTTGGAACAGCAGAATATGGGCCAAACAGGATATCTG TGGTAAGCAGTTCCTGCCCCGGCTCAGGGCCAAGAACAGATGGTCCCCAGATGC GGTCCCGCCCTCAGCAGTTTCTAGAGAACCATCAGATGTTTCCAGGGTGCCCCAA GGACCTGAAATGACCCTGTGCCTTATTTGAACTAACCAATCAGTTCGCTTCTCGC
TTCTGTTCGCGCGCTTCTGCTCCCCGAGCTCTATATAAGCAGAGCTCGTTTAGTG AACCGTCAGATCGCTAGCACCGGTGCCGCCACCATGCCTCTGGGCCTGCTGTGGC TGGGCCTGGCCCTGCTGGGCGCCCTGCACGCCCA GGCCGGCGTGCAGGTGGAGA CAATCTCCCCAGGCGACGGACGCACATTCCCTAAGCGGGGCCAGACCTGCGTGG TGCACTATACAGGCATGCTGGAGGATGGCAAGAAGTTTGACAGCTCCCGGGATA GAAACAAGCCATTCAAGTTTATGCTGGGCAAGCAGGAAGTGATCAGAGGCTGGG AGGAGGGCGTGGCCCAGATGTCTGTGGGCCAGAGGGCCAAGCTGACCATC AGCC CAGACTACGCCTATGGAGCAACAGGCCACCCAGGAATCATCCCACCTCACGCCA CCCTGGTGTTCGATGTGGAGCTGCTGAAGCTGGGCGAGGGCGGTAGTCAGAACC TTGTGATACCATGGGCCCCAGAAAATCTCACACTTCATAAAACTTTCCGAATCACA
ACTCGAACTCAACTGGAATAACCGGTTCCTGAATCACTGTCTTGAACACCTGGTA CAATATCGGACCGACTGGGATCACTCATGGACAGAACAATCTGTGGACTATAGG CACAAATTCTCACTCCCAAGCGTAGACGGCCAAAAAAGATACACTTTTCGCGTA CGATCCCGCTTTAATCCTCTCTGCGGCTCTGCTCAGCACTGGAGTGAATGGTCCC ATCCCATTCATTGGGGATCCAACACATCAAAAGAGAACCCCTTTCTGTTCGCATT GGAGGCCGTAGTCATATCTGTTGGATCCATGGGACTTATTATCTCCCTGTTGTGT GTGTACTTCTGGCTGGAACGGACTATGCCCAGGATCCCCACGCTCAAGAATCTG GAAGATCTCGTCACAGAATACCATGGTAATTTCAGCGCCTGGAGCGGAGTCTCT
AAGGGTCTGGCCGAATCCCTCCAACCCGATTATTCTGAACGGTTGTGCCTCGTAT CCGAAATACCACCAAAAGGCGGGGCTCTGGGTGAGGGCCCAGGGGCGAGTCCG TGCAATCAACACAGCCCGTATTGGGCCCCTCCTTGTTATACGTTGAAGCCCGAAA CTGGAAGCGGAGCTACTAACTTCAGCCTGCTGAAGCAGGCTGGAGACGTGGAGG AGAACCCTGGACCTATGGCACTGCCCGTGACCGCCCTGCTGCTGCCTC TGGCCCT GCTGCTGCACGCAGCCCGGCCTATCCTGTGCACGAGATGTGGCACGAGGGCCT GGAGGAGGCCAGCAGGCTGTATTTTGGCGAGCGCAACGTGAAGGGCATGTTCGA GGTGCTGGAGCCTCTGCACGCCATGATGGAGAGAGGCCCACAGACCCTGAAGGA GACATCCTTTAACCAGGCCTATGGACGGGACCT GATGGAGGCACAGGAGTGGTG CAGAAAGTACATGAAGTCTGGCAATGT-GAAGGACCTGCTGCAGGCCTGGGATCT GTACTATCACGTGTTTCGGAGAATCTCCAAGG-GAGGTTCAAAACCTTTTGAGAAC CTTAGACT-GATGGCGCCCATCTCTCTGCAGGTAGTTCACGTT-GAGACCCATAGAT GCAATATAAGCTGGGAAATCTCACAAGCCAGCCAT-TACTTTGAACGGCATTTGG AAT-TCGAGGCCCGAACACTTTCCCCCGGTCATACGTGG-GAAGAAGCTCCTCTCTT GACGCTGAAGCAGAAGCAGGAGTGGATTTGTCTG-GAGACTTTGACTCCTGATAC TCAGTATGAGTTC-CAAGTTCGGGTGAAACCACTCCAAGGCGAGTT-CACGACGTG GTCTCCGTGGAGT-CAACCGTTGGCGTTCCGCACGAAGCCCGCTGCCC TTGGCAAA GACACGATTCCGTGGCTTGGG-CATCTGCTCGTTGGGCTGAGTGGTGCGTTTGGTT TCATCATCTTGGTCTATCTCTTGATCAAT-TGCAGAAATACAGGCCCTTGGCTGAA AAAAGTGCTCAAGTGTAATACCCCCGACC-CAAGCAAGTTCTTCTCCCAGCTTTCT TCAGAG-CATGGAGGCGATGTGCAGAAATGGCTCTCTT-CACCTTTTCCCTCCTCAA GCTTCTCCCCGGGAGGGCTGGCGCCCGAGATTT-CACCTCTTGAGGTACTTGAACG AGACAAGGT-TACCCAACTTCTCCTTCAACAGGA-TAAGGTACCCGAACCTGCGAG CCTTAGCTCCAACCACTCTCTTACGAGCTGCTT-CACCAATCAGGGATACTTCTTTT TCCACCTTCCC-GATGCGCTGGAAATCGAAGCTTGTCAAGTTTACTT-TACCTATGA TCCATATAGCGAGGAA-GATCCCGACGAAGGAGTCGCCGGTGCGCC-CACGGGTTC CTCACCC-CAACCTCTCCAGCCTCTCTCAGGAGAAGATGATGC TTATTGCACTTTT CCCAGTAGAGAC-GATCTCCTCCTCTTTTCTC-CATCTCTTTTGGGGGACCTTCCCC CCCTTC-TACGGCACCTGGCGGGTCTGGTGCTGGCGAGGAG CGGATGCCGCCGTC CCTCCAGGAGCGAGTAC-CACGAGATTGGGGATCCCCAGCCACTTGGACCCCC-CAC CCCCGGCGTACCTGACCTTGTCGATTTT-CAACCTCCCCCTGAATTGGTGCTGCGA GAGGCTGGGGAG-GAAGTTCCGGACGCTGGGCCGAGG-GAGGGCGTGTCCTTTCCA TGGAGTAGGCCTCCAGGTCAAGGCGAGTT-TAGGGCTCTCAACGCGGCTGCCG TTGAATACA-GACGCTTATCTCTCACTGCAG-GAACTGCAAGGTCAGGACCCAACA CATCTTGTAGGATCTGGTGCTACTAAT-TTTTCTCTTTTGAAGCAAGCTGGAGATGT TGAAGAGAACCCTGGTCCAGT-GAGCAAGGGCGAGGAGCTGTTCACCGGGGTGGT GCC-CATCCTGGTCGAGCTGGACGGCGACGTAAACGGC-CACAAGTTCAGCGTGTC CGGCGAGGGCGAGGGC-GATGCCACCTACGGCAAGCTGACCCTGAAGTTCA TCTG CACCACCGGCAAGCTGCCCGTGCCCTGGCC-CACCCTCGTGACCACCCTGACCTAC GGCGTGCAGTGCTTCAGCCGCTACCCCGACCACAT-GAAGCAGCACGACTTCTTC AAGTCCGC-CATGCCCGAAGGCTACGTCCAGGAGCGCAC-CATCTTCTTCAAGGAC GACGGCAACTACAAGACCCGCGCCGAGGT-GAAGTTCGAGGGCGACACCCTGGTG AACCG-CATCGAGCTGAAGGGCATCGACTT-CAAGGAGGACGGCAACATCCTGGGG CACAAGCTGGAGTACAACTACAACAGC-CACAACGTCTATATCATGGCCGACAAG CAGAAGAACGGCATCAAGGTGAACTTCAA-GATCCGCCACAACATCGAGGACGG CAGCGTGCAGCTCGCCGACCAC-TACCAGCAGAACACCCCCATCGGCGACGGCCC CGTGCTGCTGCCCGACAACCACTACCT-GAGCACCCAGTCCGCCCTGAGCAAAGA CCC-CAACGAGAAGCGCGATCACATGGTCCTGCTG-GAGTTCGTGACCGCCGCCGG GATCACTCTCGGCATGGACGAGCTGTA-CAAGTAAACTAGTGTCGACAATCAACC TCTGGAT-TACAAAATTTGTGAAAGATTGACTGGTATTCT-TAACTATGTTGCTCCTT TTACGCTATGTGGATACGCTGCTT-TAATGCCTTTGTATCATGCTATTGCTTCCCGT ATGGCTTTCAT-TTTCTCCTCCTTGTATAAATCCTGGTTGCTGTCTCTT-TATGAGGA GTTGGCCCGTTGTCAGGCAACGTGGCGTGGTG TGCACTGTGTTTGCTGACGCA ACCCC-CACTGGTTGGGGCATTGCCAC-CACCTGTCAGCTCCTTTCCGGGACTTTCG CTTTCCCCCTCCCTATTGCCACGGCGGAACT-CATCGCCGCCTGCCTTGCCCGCTG CTGGACAGGGGCTCGGCTGTTGGGCACTGACAAT-TCCGTGGTGTTGTCGGGGAA GCTGACGTCCTTTC-CATGGCTGCTCGCCTGTGTTGCCACCTGGAT-TCTGCGCGGG ACGTCCTTCTGCTACGTCCCTTCGGCCCT-CAATCCAGCGGACCTTCCTTCCCGCG GCCTGCTGCCGGCTCTGCGGCCTCTTCCGCGTCTT CGCCTTCGCCCTCAGACGAG TCG-GATCTCCCTTTGGGCCGCCTCCCCGCCTGGAAT-TCGAGCTCGGTACCTTTAA GACCAATGACTTA-CAAGGCAGCTGTAGATCTTAGCCACTTTTTAAAAG AAAAGG GGGGACTGGAAGGGCTAATTCACTCC-CAACGAAGACAAGATCTGCTTTTTGCTTG TACTGGGTCTCTCTGGTTAGACCAGATCT-GAGCCTGGGAGCTCTCTGGCTAACTA GGGAACC-CACTGCTTAAGCCTCAATAAAGCTTGCCTT-GAGTGCTTCAAGTAGTGT GTGCCCGTCTGTTGTGTGACTCTGGTAACTAGAGA TCCCTCAGACCCTTTTAGTC AGTGTG-GAAAATCTCTAGCAGTAGTAGTTCATGTCATCTTAT-TATTCAGTATTTAT AACTTGCAAAGAAAT-GAATATCAGAGAGTGAGAGGAACTTGTTTATTGCA GCTT ATAATGGTTACAAATAAAGCAATAGCAT-CACAAATTTCACAAATAAAGCATTTTT TTCACTG-CATTCTAGTTGTGGTTTGTCCAAACTCAT-CAATGTATCTTATCATGTCT GGCTCTAGC-TATCCCGCCCCTAACTCCGCCCAGTTCCGCCCAT-TCTCCGCCCCAT GGCTGACTAATTTTTTTATT-TATGCAGAGGCCGAGGCCGCCTCGGCCTCTGAGC TATTCCAGAAGTAGTGAGGAGGCTTTTTG-GAGGCCTAGGCTTTTGCGTCGAGAC GTACCCAAT-TCGCCCTATAGTGAGTCGTATTACGCGCGCT-CACTGGCCGTCGTTT TACAACGTCGTGACTGGGAAAACCCTGGCGT-TACCCAACTTAATCGCCTTGCAGC ACATCCCCCTTTCGCCAGCTGGCGTAATAGCGAAG AGGCCCGCACCGATCGCCC TTCC-CAACAGTTGCGCAGCCT- GAATGGCGAATGGCGCGACGCGCCCTGTAGCGGCGCATTAAGCGCGGCGGGTGTGGTGGTTACGCGCAGCGTGACCGCTACACTTGCCAGCGCCCTAGCGCCCGCTCCTTTCGCTTTCTTCCCTTCCTTTCTCGCCACGTTCG CCGGCTTTCCCGTCAAGCTCTAAATCGGGGGCTCCCTTTAGGGTTCCGATTTAG TGCTTTACGGCACCTCGACCCCAAAAAACTTGATTAGGGTGATGGTTCACGTAGTGGGCCATCGCCCTGATAGACGGTTTTTCGCCCTTTGACGTTGGAGTCCACGTTCT TTAATAGTGGACTCTTGTTCCAAACTGGAACAACACTCAACCCTATCTCGGTCTATTCTTTTGATTTATAAGGGATTTTGCCGATTTCGGCCTATTGGTTAAAAAATGAGC TGATTTAACAAAAATTTAACGCGAATTTTAACAAAATATTAACGTTTACAATTTCCCAGGTGGCACTTTTCGGGGAAATGTGCGCGGAACCCCTATTTGTTTATTTTTCT AAATACATTCAAATATGTATCCGCTCATGAGACAATAACCCTGATAAATGCTTCAATAATATTGAAAAAGGAAGAGTATGAGTATTCAACATTTCCGTGTCGCCCTTATT CCCTTTTTTGCGGCATTTTGCCTTCCTGTTTTTGCTCACCCAGAAACGCTGGTGAAAGTAAAAGATGCTGAAGATCAGTTGGGTGCACGAGTGGGTTACATCGAACTGGA TCTCAACAGCGGTAAGATCCTTGAGAGTTTTCGCCCCGAAGAACGTTTTCCAATGATGAGCACTTTTAAAGTTCTGCTATGTGGCGCGGTATTATCCCGTATTGACGCCGGGCAAGAGCAACTCGGTCGCCGCATACACTATTCTCAGAATGACTTGGTTAGT ACTCACCAGTCACAGAAAAGCATCTTACGGATGGCATGACAGTAAGAGAATTATGCAGTGCTGCCATAACCATGAGTGATAACACTGCGGCCAACTTACTTCTGACAACGATCGGAGGACCGAAGGAGCTAACCGCTTTTTTGCACAACATGGGGGATCATGTAACTCGCCTTGATCGTTGGGAACCGGAGCTGAATGAAGCCATACCAAACGACG AGCGTGACACCACGATGCCTGTAGCAATGGCAACAACGTTGCGCAAACTATTAACTGGCGAACTACTTACTCTAGCTTCCCGGCAACAATTAATAGACTGGATGGAGGC GGATAAAGTTGCAGGACCACTTCTGCGCTCGGCCCTTCCGGCTGGCTGGTTTATT GCTGATAAATCTGGAGCCGGTGAGCGTGGGTCTCGCGGTATCATTGCAGCACTGGGGCCAGATGGTAAGCCCTCCCGTATCGTAGTTATCTACACGACGGGGAGTCAG GCAACTATGGATGAACGAAATAGACAGATCGCTGAGATAGGTGCCTCACTGATTAAGCATTGGTAACTGTCAGACCAAGTTTACTCATATATACTTTAGATTGATTTAA AACTTCATTTTTAATTTAAAAGGATCTAGGTGAAGATCCTTTTTGATAATCTCATGACCAAAATCCCTTAACGTGAGTTTTCGTTCCACTGAGCGTCAGACCCCGTAGAAA AGATCAAAGGATCTTCTTGAGATCCTTTTTTTCTGCGCGTAATCTGCTGCTTGCAA ACAAAAAAACCACCGCTACCAGCGGTGGTTTGTTTGCCGGATCAAGAGCTACCAACTCTTTTTCCGAAGGTAACTGGCTTCAGCAGAGCGCAGATACCAAATACTGTCCTTCTAGTGTAGCCGTAGTTAGGCCACCACTTCAAGAACTCTGTAGCACCGCCTACATACCTCGCTCTGCTAATCCTGTTACCAGTGGCTGCTGCCAGTGGCGATAAGTCGTGTCTTACCGGGTTGGACTCAAGACGATAGTTACCGGATAAGGCGCAGCGGTCG GGCTGAACGGGGGGTTCGTGCACACAGCCCAGCTTGGAGCGAACGACCTACACCGAACTGAGATACCTACAGCGTGAGCTATGAGAAAGCGCCACGCTTCCCGAAGGGAGAAAGGCGGACAGGTATCCGGTAAGCGGCAGGGTCGGAACAGGAGAGCGCAC GAGGGAGCTTCCAGGGGGAAACGCCTGGTATCTTTATAGTCCTGTCGGGTTTCGC CACCTCTGACTTGAGCGTCGATTTTTGTGATGCTCGTCAGGGGGCGGAGCCTATGGAAAAACGCCAGCAACGCGGCCTTTTTACGGTTCCTGGCCTTTTGCTGGCCTTT TGCTCACATGTTCTTTCCTGCGTTATCCCCTGATTCTGTGGATAACCGTATTACCGCCTTTGAGTGAGCTGATACCGCTCGCCGCAGCCGAACGACCGAGCGCAGCGAGT CAGTGAGCGAGGAAGCGGAAGAGCGCCCAATACGCAAACCGCCTCTCCCCGCGC GTTGGCCGATTCATTAATGCAGCTGGCACGACAGGTTTCCCGACTGGAAAGCGG GCAGTGAGCGCAACGCAATTAATGTGAGTTAGCTCACTCATTAGGCACCCCAGG CTTTACACTTTATGCTTCCGGCTCGTATGTTGTGTGGAATTGTGAGCGGATAACAATTTCACACAGGAAACAGCTATGACCATGATTACGCCAAGCGCGCAATTAACCC TCACTAAAGGGAACAAAAGCTGGAGCTGCA; SEQ ID NO: 18). SEQ ID NO: 18 encodes the protein sequences as set forth in SEQ ID NOs: 3 and 4.

In some embodiments, the expression vector is a variant of SEQ ID NO: 20 as set forth in SEQ ID NO: 19 (AGCTTAATGTAGTCTTATGCAATACTCTTGTAGTCTTGCAACATGGTAACGATGA GTTAGCAACATGCCTTACAAGGAGAGAAAAAGCACCGTGCATGCCGATTGG TGG AAGTAAGGTGGTACGATCGTGCCTTATTAGGAAGGCAACAGACGGGTCTGACAT GGATTGGACGAACCACTGAATTGCCGCATTGCAGAGATATTGTATTTAAGTGCCTAGCTCGATACAATAAACGGGTCTCTCTGGTTAGACCAGATCTGAGCCTGGGAGCTCTCTGGCTAACTAGGGAACCCACTGCTTAAGCCTCAATAAAGCTTGCCTTGAGT GCTTCAAGTAGTGTGTGCCCGTCTGTTGTGTGACTCTGGTAACTAGAGATCCCTC AGACCCTTTTAGTCAGTGTGGAAAATCTCTAGCAGTGGCGCCCGAACAGGGACTTGAAAGCGAAAGGGAAACCAGAGGAGCTCTCTCGACGCAGGACTCGGCTTGCTGAAGCGCGCACGGCAAGAGGCGAGGGGCGGCACTGGTGAGTACGCCAAAAATT TTGACTAGCGGAGGCTAGAAGGAGAGAGATGGGTGCGAGAGCGTCAGTATTAA GCGGGGGAGAATTAGATCGCGATGGGAAAAAATTCGGTTAAGGCCAGGGGGAA AGAAAAAATATAAATTAAAACATATAGTATGGGCAAGCAGGGAGCTAGAACGATTCGCAGTTAATCCTGGCCTGTTAGAAACATCAGAAGGCTGTAGACAAATACTG GGACAGCTACAACCATCCCTTCAGACAGGATCAGAAGAACTTAGATCATTATATAATACAGTAGCAACCCTCTATTGTGTGCATCAAAGGATAGAGATAAAAGACACC AAGGAAGCTTTAGACAAGATAGAG GAAGAGCAAAACAAAAGTAAGACCACCGCACAGCAAGCGGCCGCTGATCTTCAGACCTGGAGGAGGAGATATGAGGGACAATT GGAGAAGTGAATTATATAAATATAAAGTAGTAAAAATTGAACCATTAGGAGTAG
CACCCACCAAGGCAAAGAGAAGAGTGGTGCAGAGAGAAAAAAGAGCAGTGGGA ATAGGAGCTTTGTTCCTTGGGTTCTTGGGAGCAGCAGGAAGCACTATGGGCGCA GCCTCAATGACGCTGACGGTACAGGCCAGACAATTATTGTCTGGTATAGTGCAG CAGCAGAACAATTTGCTGAGGGCTATTGAGGCGCAACAGCATCTGTTGCAACTC ACAGTCTGGGGCATCAAGCAGCTCCAGGCAAGAATCCTGGCTGTGGAAAGATAC CTAAAGGATCAACAGCTCCTGGGGATTTGGGGTTGCTCTGGAAAACTCATTTGCACCACTGCTGTGCCTTGGAATGCTAGTTGAGTAATAAATCTCTGGAACAGATTTG GAATCACACGACCTGGATGGAGTGGGACAGAGAAATTAACAATTACACAAGCTT AATACACTCCTTAATTGAAGAATCGCAAAACCAGCAAGAAAAGAATGAACAAG AATTATTGGAATTAGATAAATGGGCAAGTTTGTGGAATTGGTTTAACATAA CAA ATTGGCTGTGGTATATAAAATTATTCATAATGATAGTAGGAGGCTTGGTAGGTTT
AAGAATAGTTTTTGCTGTACTTTCTATAGTGAATAGAGTTAGGCAGGGATATTCA CCATTATCGTTTCAGACCCACCTCCCAACCCCGAGGGGACCCGACAGGCCCGAAGGAATAGAAGAAGAAGGTGGAGAGAGAGACAGAGACAGATCCATTCGATTAGT GAACGGATCTCGACGGTATCGGTTAACTTTTAAAAGAAAAGGGGGGATTGGGGG GTACAGTGCAGGGGAAAGAATAGTAGACATAATAGCAACAGACATACAAACTA AAGAATTACAAAAACAAATTACAAAAATTCAAAATTTTATCGATCACGAGACTA GCCTCGAGAAGCTTGATATCGAATTCCCACGGGGTTGGACGCGTAGGAACAGAG AAACAGGAGAAATATGGGCCAAACAGGATATCTGTGGTAAGCAGTTCCTGCCCCG GCTCAGGGCCAAGAACAGTTGGAACAGCAGAATATGGGCCAAACAGGATATCTG TGGTAAGCAGTTCCTGCCCCGGCTCAGGGCCAAGAACAGATGGTCCCCAGATGC GGTCCCGCCCTCAGCAGTTTCTAGAGAACCATCAGATGTTTCCAGGGTGCCCCAA GGACCTGAAATGACCCTGTGCCTTATTTGAACTAACCAATCAGTTCGCTTCTCGC TTCTGTTCGCGCGCTTCTGCTCCCCGAGCTCTATATAAGCAGAGCTCGTTTAGTG AACCGTCAGATCGCTAGCACCGGTGCCGCCACCATGCCTCTGGGCCTGCTGTGGC TGGGCCTGGCCCTGCTGGGCGCCCTGCACGCCCAGGCCGGCGTGCAGGTGGAGA
CAATCTCCCCAGGCGACGGACGCACATTCCCTAAGCGGGGCCAGACCTGCGTGG TGCACTATACAGGCATGCTGGAGGATGGCAAGAAGTTTGACAGCTCCCGGGATA GAAACAAGCCATTCAAGTTTATGCTGGCAAGCAGGAAGTGATCAGAGGCTGGG AGGAGGGCGTGGCCCAGATGTCTGTGGGCCAGAGGGCCAAGCTGACCATCAGCC CAGACTACGCCTATGGAGCAACAGGCCACCCAGGAATCATCCCACCTCACGCCA CCCTGGTGTTCGATGTGGAGCTGCTGAAGCTGGGCGAGCAAAACTTGGTGATTCC TTGGGCCCCAGAAAATCTCACGCTTCACAAGTTGTCCGAATCCCAGCTCGAGCTC
AACTGGAATAATAGATTTCTTAATCATTGTTTGGAACACCTGGTTCAATATAGAA CGGATTGGGACCACTCATGGACCGAGCAGTCAGTTGACTACCGCCACAAATTTT CACTTCCCAGCGTAGATGGGCAGAAGAGGTACACATTTAGGGTCAGATCCAGGT TTAATCCTCTGTGTGGTTCTGCTCAACACTGGTCTGAGTGGAGCCATCCGATCCA CTGGGGCTCAAATACCTCTAAAGAAAATCCGTTCCTCTTTGCGCTCGAAGCCGTT GTTATCAGCGTCGGAAGCATGGGACTTATCATTTCCCTTCTCTGCGTGTACTTCTG GCTGGAGCGGACGATGCCGCGGATTCCGACGCTCAAAAACCTGGAGGACCTTGT AACAGAATATCACGGTAATTTCTCCGCTTGGAGTGGCGTATCAAAGGGGCTTGCT GAGTCCCTTCAACCGGATTACTCTGAGCGCCTCTGCTTGGTGTCCGAGATACCTC CAAAGGAGGTGCACTTGGGGAGGGGCCAGGCGCGTCCCCTTGCAATCAGCATA GTCCGTATTGGGCGCCCCCCTGTTATACCCTCAAACCGGAAACGGGAAGCGGAG CTACTAACTTCAGCCTGCTGAAGCAGGCTGGAGACGTGGAGGAGAACCCTGGAC CTATGGCACTGCCCGTGACCGCCCTGCTGCTGCCTCTGGCCCTGCTGCTGCACGC AGCCCGGCCTATCCTGTGGCACGAGATGTGGCACGAGGGCCTGGAGGAGGCCAG CAGGCTGTATTTGGCGAGCGCAACGTGAAGGGCATGTTCGAGGTGCTGGAGCC TCTGCACGCCATGATGGAGAGAGGCCCACAGACCCTGAAGGAGACATCCTTTAA CCAGGCCTATGGACGGGACCTGATGGAGGCACAGGAGTGGTGCAGAAAGTACAT GAAGTCTGGCAATGTGAAGGACCTGCTGCAGGCCTGGGATCTGTACTATCACGT GTTTCGGAGAATCTCCAAGAAACCTTTTGAGAACCTTAGACTGATGGCGCCCATC TCTCTGCAGGTAGTTCACGTTGAGACCCATAGATGCAATATAAGCTGGGAAATCT CACAAGCCAGCCATTACTTTGAACGGCATTTGGAATTCGAGGCCCGAACACTTTC CCCCGGTCATACGTGGGAAGAAGCTCCTCTCTTGACGCTGAAGCAGAAGCAGGA GTGGATTTGTCTGGAGACTTTGACTCCTGATACTCAGTATGAGTTCCAAGTTCGG GTGAAACCACTCCAAGGCGAGTTCACGACGTGGTCTCCGTGGAGTCAACCGTTG GCGTTCCGCACGAAGCCCGCTGCCCTTGGCAAAGACACGATTCCGTGGCTTGGG CATCTGCTCGTTGGGCTGAGTGGTGCGTTTGGTTTCATCATCTTGGTCTATCTCTT GATCAATTGCAGAAATACAGGCCCTTGGCTGAAAAAAGTGCTCAAGTGTAATAC CCCCGACCCAAGCAAGTTCTTCTCCCAGCTTTCTTCAGAGCATGGAGGCGATGTG CAGAAATGGCTCTCTTCACCTTTTCCCTCCTCAAGCTTCTCCCGGGAGGGCTGG CGCCCGAGATTTCACCTCTTGAGGTACTTGAACAGGATAAGGTACCCGAACCTGCGAGCCTTAGCTCCAACCACTCTCTT ACGAGCTGCTTCACCAATCAGGGATACTTCTTTTTCCACCTTCCCGATGCGCTGG AAATCGAAGCTTGTCAAGTTTACTTTACCTATGATC CATATAGCGAGGAAGATCCCGACGAAGGAGTCGCGCGGTGCGCCCACGGGTTCCTCACCCCAACCTCTCCAGCCTCTCTCAGGAGAAGATGATGCTTATTGCACTTTTCCCAGTAGAGACGATCTCCTCCTCTTTTCTCCATCTCTTTTGGGGGGACCTTCCCCCCCTTCTACGGCACCTGGCGG GTCTGGTGCTGGCGAGGAGCGGATGCCGCCGTCCTCCAGGAGCGAGTACCACG AGATTGGGATCCCCAGCCACTTGGACCCCCCACCCCCGGCGTACCTGACCTTGTC GATTTTCAACCTCCCCCTGAATTGGTGCTGCGAGAGGCTGGGGAGGAAGTTCCGGACGCTGGGCCGAGGGAGGGCGTGTCCTTTCCATGGAGTAGGCCTCCAGGTCAA GGCGAGTTTAGGGCTCTCAACGCGCGGCTGCCGTTGAATACAGACGCTTATCTCTCACTGCAGGAACTGCAAGGTCAGGACCCAACACATCTTGTAGGATCTGGTGCTA CTAATTTTTCTCTTTTGAAGCAAGCTGGAGATGTTGAAGAGAACCCTGGTCCAGTGAGCAAGGGCGAGGAGCTGTTCACCGGGGTGGTGCCCATCCTGGTCGAGCTGGACGGCGACGTAAACGGCCACAAGTTCAGCGTGTCCGGCGAGGGCGAGGGCGATG CCACCTACGGCAAGCTGACCCTGAAGTTCATCTGCACCACCGGCAAGCTGCCCGTGCCCTGGCCCACCCTCGTGACCACCCTGACCTACGGCGTGCAGTGCTTCAGCCG CTACCCCGACCACATGAAGCAGCACGACTTCTTCAAGTCCGCCATGCCCGAAGGCTACGTCCAGGAGCGCACCATCTTCTTCAAGGACGACGGCAACTACAAGACCCGCGCCGAGGTGAAGTTCGAGGGCGACACCCTGGTGAACCGCATCGAGCTGAAGGG CATCGACTTCAAGGAGGACGGCAACATCCTGGGGCACAAGCTGGAGTACAACTACAACAGCCACAACGTCTATATCATGGCCGACAAGCAGAAGAACGGCATCAAGGTGAACTTCAAGATCCGCCACAACATCGAGGACGGCAGCGTGCAGCTCGCCGACCACTACCAGCAGAACACCCCCATCGGCGACGGCCCCGTGCTGCTGCCCGACAACCA CTACCTGAGCACCCAGTCCGCCCTGAGCAAAGACCCCAACGAGAAGCGCGATCACATGGTCCTGCTGGAGTTCGTGACCGCCGCCGGGATCACTCTCGGCATGGACGA GCTGTACAAGTAAACTAGTGTCGACAATCAACCTCTGGATTACAAAATTTGTGAAAGATTGACTGGTATTCTTAACTATGTTGCTCCTTTTACGCTATGTGGATACGCTGCTTTAATGCCTTTGTATCATGCTATTGCTTCCCGTATGGCTTTCATTTTCTCCTCCTTGTATAAATCCTGGTTGCTGTCTCTTTATGAGGAGTTGTGGCCCGTTGTCAGGCAACGTGGCGTGGTGTGCACTGTGTTTGCTGACGCAACCCCCACTGGTTGGGGCATTG CCACCACCTGTCAGCTCCTTTCCGGGACTTTCGCTTTCCCCTCCCTATTGCCACG GCGGAACTCATCGCCGCCTGCCTTGCCCGCTGCTGGACAGGGCTCGGCTGTTGG GCACTGACAATTCCTGGTGTTGTCGGGGAAGCTGACGTCCTTTCCATGGCTGCT CGCCTGTGTTGCCACCTGGATTCTGCGCGGGACGTCCTTCTGCTACGTCCCTTCGCCCTCAATCCAGCGGACCTTCCTTCCCGCGGCCTGCTGCGGCTCTGCGGCCTC TTCCGCGTCTTCGCCTTCGCCCTCAGACGAGTCGGATCTCCCTTTGGGCCGCCTCC CCGCCTGGAATTCGAGCTCGGTACCTTTAAGACCAATGACTTACAAGGCAGCTGTAGATCTTAGCCACTTTTTAAAAGAAAAGGGGGGACTGGAAGGGCTAATTCACTC CCAACGAAGACAAGATCTGCTTTTTGCTTGTACTGGGTCTCTCTGGTTAGACCAG ATCTGAGCCTGGGAGCTCTCTGGCTAACTAGGGAACCCACTGCTTAAGCCTCAAT AAAGCTTGCCTTGAGTGCTTCAAGTAGTGTGTGCCCGTCTGTTGTGTGACTCTGGTAACTAGAGATCCCTCAGACCCTTTTAGTCAGTGTGGAAAATCTCTAGCAGTAGT AGTTCATGTCATCTTATTATTCAGTATTTATAACTTGCAAAGAAATGAATATCAGAGAGTGAGAGGAACTTGTTTATTGCAGCTTATAATGGTTACAAATAAAGCAATAGCATCACAAATTTCACAAATAAAGCATTTTTTTCACTGCATTCTAGTTGTGGTTTGTCCAAACTCATCAATGTATCTTATCATGTCTGGCTCTAGCTATCCCGCCCCTAACTCCGCCCAGTTCCGCCCATTCTCCGCCCCATGGCTGACTAATTTTTTTTATTTATGCAGAGGCCGAGGCCGCCTCGGCCTCTGAGCTATTCCAGAAGTAGTGAGGAGGCTT TTTTGGAGGCCTAGGCTTTTGCGTCGAGACGTACCCAATTCGCCCTATAGTGAGTCGTATTACGCGCGCTCACTGGCCGTCGTTTTACAACGTCGTGACTGGGAAAACCC TGGCGTTACCCAACTTAATCGCCTTGCAGCACATCCCCCTTTCGCCAGCTGGCGTAATAGCGAAGAGGCCCGCACCGATCGCCCTTCCCAACAGTTGCGCAGCCTGAATGGCGAATGGCGCGACGCGCCCTGTAGCGGCGCATTAAGCGCGGCGGGTGTGGTGGTTACGCGCAGCGTGACCGCTACACTTGCCAGCGCCCTAGCGCCCGCTCCTTTCGCTTTCTTCCCTTCCTTTCTCGCCACGTTCGCCGGCTTTCCCCGTCAAGCTCTAAATCGGGGGCTCCCTTTAGGGTTCCGATTTAGTGCTTTACGGCACCTCGACCCCAAAAAACTTGATTAGGGTGATGGTTCACGTAGTGGGCCATCGCCCTGATAGACGGTTTTTCGCCCTTTGACGTTGGAGTCCACGTTCTTTAATAGTGGACTCTTGTTCCAAACTGGAACAACACTCAACCCTATCTCGGTCTATTCTTTTGATTTATAAGGGATTTTGCCG ATTTCGGCCTATTGGTTAAAAAATGAGCTGATTTAACAAAAATTTAACGCGAATT TTAACAAAATATTAACGTTTACAATTTCCCAGGTGGCACTTTTCGGGGAAATGTG CGCGGAACCCCTATTTGTTTATTTTTCTAAATACATTCAAATATGTATCCGCTCATGAGACAATAACCCTGATAAATGCTTCAATAATATTGAAAAAGGAAGAGTATGAG TATTCAACATTTCCGTGTCGCCCTTATTCCCTTTTTTGCGGCATTTTGCCTTCCTGT TTTTGCTCACCCAGAAACGCTGGTGAAAGTAAAAGATGCTGAAGATCAGTTGGG TGCACGAGTGGGTTACATCGAACTGGATCTCAACAGCGGTAAGATCCTTGAGAG TTTTCGCCCCGAAGAACGTTTTCCAATGATGAGCACTTTTAAAGTTCTGCTATGT GGCGCGGTATTATCCCGTATTGACGCCGGGCAAGAGCAACTCGGTCGCCGCATACACTATTCTCAGAATGACTTGGTTGAGTACT CACCAGTCACAGAAAAGCATCTTA CGGATGG-
CATGACAGTAAGAGAATTATGCAGTGCTGCCAT-
AACCATGAGTGATA
ACACTGCGGCCAACTTACTTCTGACAACGATCG-
GAGGACCGAAGGAGCTAACCG CTTTTTTGCACAA-
CATGGGGGATCATGTAACTCGCCTTGATCGTTGG-
GAACCGGA
GCTGAATGAAGCCATAC-
CAAACGACGAGCGTGACACCAC-
GATGCCTGTAGCAAT
GGCAACAACGTTGCGCAAACTAT-
TAACTGGCGAACTACTTACTCTAGCTTCCCGG
CAACAATTAATAGACTGGATGGAGGCGGA-
TAAAGTTGCAGGACCACTTCTGCGC
TCGGCCCTTCCGGCTGGCTGGTTTATTGCTGA-
TAAATCTGGAGCCGGTGAGCGTG
GGTCTCGCGGTATCATTGCAGCACTGGGGCCA-
GATGGTAAGCCCTCCCGTATCGT AGTTATCTA-
CACGACGGGGAGTCAGGCAACTATGGAT-
GAACGAAATAGACAGAT
CGCTGAGATAGGTGCCTCACTGATTAAGCAT-
TGGTAACTGTCAGACCAAGTTTAC TCATATATACTT-
TAGATTGATTTAAAACTTCATTTTTAATT-
TAAAAGGATCTAGGT
GAAGATCCTTTTTGATAATCTCATGAC-
CAAAATCCCTTAACGTGAGTTTTCGTTCC ACT-
GAGCGTCAGACCCCGTAGAAAAGAT-
CAAAGGATCTTCTTGAGATCCTTTTTT
TCTGCGCGTAATCTGCTGCTTGCAAACAAAAAAAC-
CACCGCTACCAGCGGTGGT TTGTTTGCCGGAT-
CAAGAGCTAC-
CAACTCTTTTTCCGAAGGTAACTGGCTTCAGC
AGAGCGCAGATAC-
CAAATACTGTCCTTCTAGTGTAGCCGTAGTTAGGC-
CACCACT TCAAGAACTCTGTAGCACCGCCTACAT-
ACCTCGCTCTGCTAATCCTGTTACCAGT
GGCTGCTGCCAGTGGCGATAAGTCGTGTCT-
TACCGGGTTGGACTCAAGACGATA GTTACCGGA-
TAAGGCGCAGCGGTCGGGCT-
GAACGGGGGGTTCGTGCACACAGCC
CAGCTTGGAGCGAACGACCTACACCGAACTGAGA-
TACCTACAGCGTGAGCTATG AGAAAGCGC-
CACGCTTCCCGAAGG-
GAGAAAGGCGGACAGGTATCCGGTAAGCG
GCAGGGTCGGAACAGGAGAGCGCACGAGG-
GAGCTTCCAGGGGGAAACGCCTGG TATCTT-
TATAGTCCTGTCGGGTTTCGCCACCTCTGACTT-
GAGCGTCGATTTTTGTG
ATGCTCGTCAGGGGGCGGAGCCTATG-
GAAAAACGCCAGCAACGCGGCCTTTTT
ACGGTTCCTGGCCTTTTGCTGGCCTTTTGCTCA-
CATGTTCTTTCCTGCGTTATCCC CTGATTCTGTGGA-
TAACCGTATTACCGCCTTTGAGTGAGCTGA-
TACCGCTCGCCG
CAGCCGAACGACCGAGCGCAGCGAGTCAGT-
GAGCGAGGAAGCGGAAGAGCGCC
CAATACGCAAACCGCCTCTCCCCGCGCGTTGGCC-
GATTCATTAATGCAGCTGGCA
CGACAGGTTTCCCGACTGGAAAGCGGGCAGT-
GAGCGCAACGCAATTAATGTGAG TTAGCTCACT-
CATTAGGCACCCCAGGCTTTACACTT-
TATGCTTCCGGCTCGTATGT
TGTGTGGAATTGTGAGCGGATAACAATTT-
CACACAGGAAACAGCTATGACCATG ATTACGC-
CAAGCGCGCAATTAACCCTCACTAAAGG-
GAACAAAAGCTGGAGCTGC A; SEQ ID NO: 19). SEQ ID NO: 19 encodes the protein sequences as set forth in SEQ ID NOs: 5 and 6.

In some embodiments, the expression vector includes a nucleic acid having at least 80%, 85%, 90%, 95%, 98% or 99% nucleic acid sequence identity (or a percentage nucleic acid sequence identity within a range defined by any two of the aforementioned percentages) with the nucleotide sequences provided herein, or a specifically derived fragment thereof. In some embodiments, the expression vector comprises a promoter. In some embodiments, the expression vector comprises the nucleic acid encoding a fusion protein. In some embodiments, the vector is RNA or DNA.

Cells and Compositions: T Lymphocyte Populations

The compositions described herein provide for genetically modified cells, such as mammalian cells, which include the protein sequences or the expression vectors as set forth and described herein. Accordingly, provided herein are cells, such as mammalian cells, for dimeric CISC secretion, wherein the cell comprises the protein sequences of anyone of the embodiments described herein or the expression vector of anyone of the embodiments described herein. In some embodiments, the cell is a bacterial cell or a mammalian cell, such as a lymphocyte. In some embodiments, the cell is *E. coli*. In some embodiments, the cell is an insect cell that permits protein expression. In some embodiments, the cell is a lymphocyte.

In some embodiments, the cells are precursor T cells or T regulatory cells. In some embodiments, the cells stem cells, such as hematopoietic stem cells. In some embodiments, the cell is a NK cell. In some embodiments, the cells are CD34+, CD8+, and/or CD4+ T lymphocytes. In some embodiments, the cell is a B cell. In some embodiments, the cell is a neuronal stem cell.

In some embodiments, the cells are CD8+ T cytotoxic lymphocyte cells, which may include naïve CD8+ T cells, central memory CD8+ T cells, effector memory CD8+ T cells, or bulk CD8+ T cells. In some embodiments, the cells are CD4+ T helper lymphocyte cells, which may include naïve CD4+ T cells, central memory CD4+ T cells, effector memory CD4+ T cells, or bulk CD4+ T cells.

The lymphocytes (T lymphocytes) can be collected in accordance with known techniques and enriched or depleted by known techniques such as affinity binding to antibodies such as flow cytometry and/or immunomagnetic selection. After enrichment and/or depletion steps, in vitro expansion of the desired T lymphocytes can be carried out in accordance with known techniques or variations thereof that will be apparent to those skilled in the art. In some embodiments, the T cells are autologous T cells obtained from a patient.

For example, the desired T cell population or subpopulation can be expanded by adding an initial T lymphocyte population to a culture medium in vitro, and then adding to the culture medium feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). The non-dividing feeder cells can comprise gamma-irradiated PBMC feeder cells. In some embodiments, the PBMC are irradiated with gamma rays in the range of 3000 to 3600 rads to prevent cell division. In some embodiments, the PBMC are irradiated with gamma rays of 3000, 3100, 3200, 3300, 3400, 3500 or 3600 rads or any value of rads between any two endpoints of any of the listed values to prevent cell division. The order of addition of the T cells and feeder cells to the culture media can be reversed if desired. The culture can typically be incubated under conditions of temperature and the like that are suitable for the growth of T lymphocytes. For the growth of human T lymphocytes, for example, the temperature will generally be at least 25° C., preferably at least 30° C., more preferably 37° C. In some embodiments, the temperature for the growth of human T lymphocytes is 22, 24, 26, 28, 30, 32, 34, 36, 37° C., or any other temperature between any two endpoints of any of the listed values.

After isolation of T lymphocytes both cytotoxic and helper T lymphocytes can be sorted into naïve, memory, and effector T cell subpopulations either before or after expansion.

CD8+ cells can be obtained by using standard methods. In some embodiments, CD8+ cells are further sorted into naïve, central memory, and effector memory cells by identifying cell surface antigens that are associated with each of those types of CD8+ cells. In some embodiments, memory T cells are present in both CD62L+ and CD62L− subsets of CD8+ peripheral blood lymphocytes. PBMC are sorted into CD62L-CD8+ and CD62L+CD8+ fractions after staining with anti-CD8 and anti-CD62L antibodies. In some embodiments, the expression of phenotypic markers of central memory $T_{CM}$ include CD45RO, CD62L, CCR7, CD28, CD3, and/or CD127 and are negative or low for granzyme B. In some embodiments, central memory T cells are CD45RO+, CD62L+, and/or CD8+ T cells. In some embodiments, effector TE are negative for CD62L, CCR7, CD28, and/or CD127, and positive for granzyme B and/or perforin. In some embodiments, naïve CD8+ T lymphocytes are characterized by the expression of phenotypic markers of naïve T cells comprising CD62L, CCR7, CD28, CD3, CD127, and/or CD45RA.

CD4+ T helper cells are sorted into naïve, central memory, and effector cells by identifying cell populations that have cell surface antigens. CD4+ lymphocytes can be obtained by standard methods. In some embodiments, naïve CD4+ T lymphocytes are CD45RO−, CD45RA+, CD62L+, and/or CD4+ T cells. In some embodiments, central memory CD4+ cells are CD62L+ and/or CD45RO+. In some embodiments, effector CD4+ cells are CD62L− and/or CD45RO−.

Whether a cell, such as a mammalian cell, or cell population, such as a population of mammalian cells, is selected for expansion depends upon whether the cell or population of cells has undergone two distinct genetic modification events. If a cell, such as a mammalian cell, or a population of cells, such as a population of mammalian cells, has undergone one or fewer genetic modification events, then the addition of a ligand will result in no dimerization. However, if the cell, such as a mammalian cell, or the population of cells, such as a population of mammalian cells, has undergone two genetic modification events, then the addition of the ligand will result in dimerization of the CISC component, and subsequent signaling cascade. Thus, a cell, such as a mammalian cell, or a population of cells, such as a population of mammalian cells, may be selected based on its response to contact with the ligand. In some embodiments, the ligand may be added in an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

In some embodiments, a cell, such as a mammalian cell, or a population of cells, such as a population of mammalian cells, may be positive for the dimeric CISC based on the expression of a marker as a result of a signaling pathway. Thus, a cell population positive for the dimeric CISC may be determined by flow cytometry using staining with a specific antibody for the surface marker and an isotype matched control antibody.

Compositions

Provided herein are compositions that comprise a genetically modified cell, such as a mammalian cell, preparation as set forth in this disclosure. In some embodiments, the cells, such as mammalian cells, include the protein sequences as described in the embodiments herein. In some embodiments, the compositions include CD4+ T cells that have a CISC comprising an extracellular binding domain, a hinge domain, a transmembrane domain, and signaling domain. In some embodiments, the CISC is an IL2R-CISC. In other embodiments, the composition further comprises a cell, such as a mammalian cell, preparation comprising CD8+ T cells that have a CISC comprising an extracellular binding domain, a hinge domain, a transmembrane domain, and a signaling domain. In some embodiments, the CISC components dimerize in the presence of a ligand, preferably simultaneously. In some embodiments, each of these populations can be combined with one another or other cell types to provide a composition.

In some embodiments, the cells of the composition are CD4+ cells. The CD4+ cell can be T helper lymphocyte cells, naïve CD4+ T cells, central memory CD4+ T cells, effector memory CD4+ T cells, or bulk CD4+ T cells. In some embodiments, the CD4+ helper lymphocyte cell is a naïve CD4+ T cell, wherein the naïve CD4+ T cell comprises a CD45RO−, CD45RA+, and/or is a CD62L+ CD4+ T cell.

In some embodiments, the cells of the composition are CD8+ cells. The CD8+ cell can be a T cytotoxic lymphocyte cell, a naïve CD8+ T cell, central memory CD8+ T cell, effector memory CD8+ T cell and/or bulk CD8+ T cell. In some embodiments, the CD8+ cytotoxic T lymphocyte cell is a central memory T cell, wherein the central memory T cell comprises a CD45RO+, CD62L+, and/or CD8+ T cell. In yet other embodiments, the CD8+ cytotoxic T lymphocyte cell is a central memory T cell and the CD4+ helper T lymphocyte cell is a naïve or central memory CD4+ T cell.

In some embodiments, the compositions comprise T cell precursors. In some embodiments, the compositions comprise hematopoietic stem cells. In some embodiments, the composition comprises a host cell wherein the host cell is a CD8+ T cytotoxic lymphocyte cell selected from the group consisting of naïve CD8+ T cells, central memory CD8+ T cells, effector memory CD8+ T cells and bulk CD8+ T cells or a CD4+ T helper lymphocyte cell that is selected from the group consisting of naïve CD4+ T cells, central memory CD4+ T cells, effector memory CD4+ T cells, and bulk CD4+ T cells and a second host cell, wherein the second host cell is a precursor T cell. In some embodiments, the precursor T cell is a hematopoietic stem cell.

In some compositions, the cells are NK cells.

In some embodiments, the cell is CD8+ or a CD4+ cell. In some embodiments, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some embodiments, the cell is a CD4+ T helper lymphocyte cell that is selected from the group consisting of naïve CD4+ T-cells, central memory CD4+ T-cells, effector memory CD4+ T-cells, and bulk CD4+ T-cells. In some embodiments, the cell is a precursor T-cell. In some embodiments, the cell is a stem cell. In some embodiments, the cell is a hematopoietic stem cell or NK cell. In some embodiments, the cell is a B cell. In some embodiments, the cell is a neuronal stem cell. In some embodiments, the cell further comprises a chimeric antigen receptor.

Also provided herein are kits and systems including the cells, expression vectors, and protein sequences provided and described herein. Thus, for example, provided herein is a kit comprising one or more of: a protein sequence as described herein; an expression vector as described herein; and/or a cell as described herein. Also provided is a system for selectively activation a signal into an interior of a cell, the system comprising a cell as described herein, wherein the cell comprises an expression vector as described herein comprising a nucleic acid encoding a protein sequence as described herein.

Method of Making a Cell that Expresses a Dimeric CISC Component

In some embodiments described herein, it may be desired to introduce a protein sequence or an expression vector into a host cell, such as a mammalian cell, e.g., a lymphocyte, to be used for drug regulated cytokine signaling and/or for the selective expansion of cells that express the dimeric CISC components. For example, the dimeric CISC can allow for cytokine signaling in cells that have the introduced CISC components for transmitting signals to the interior of a cell, such as a mammalian cell, upon contact with a ligand. In addition, the selective expansion of cells, such as mammalian cells, can be controlled to select for only those cells that have undergone two specific genetic modification events, as described herein. Preparation of these cells can be carried out in accordance with known techniques that will be apparent to those skilled in the art based upon the present disclosure.

In some embodiments, a method of making a CISC-bearing cell, such as a mammalian cell, is provided, wherein the cell expresses a dimeric CISC. The method can include delivering to a cell, such as a mammalian cell, the protein sequence of any one of the embodiments or embodiments described herein or the expression vector of the embodiments or embodiments described herein and delivering to the cell, such as a mammalian cell. In some embodiments, the protein sequence comprises a first and a second sequence. In some embodiments, the first sequence encodes for a first CISC component comprising a first extracellular binding domain, a hinge domain, a linker of a specified length, wherein the length is preferably optimized, a transmembrane domain, and a signaling domain. In some embodiments, the second sequence encodes for a second CISC component comprising a second extracellular binding domain, a hinge domain, a linker of a specified length, wherein the length is preferably optimized, a transmembrane domain, and a signaling domain. In some embodiments, the spacer is 1, 2, 3, 4, 5, 6, 7, 8, 9, 10, 11, 12, 13, 14 or 15 amino acids in length or a length within a range defined by any two of the aforementioned lengths. In some embodiments, the signaling domain comprises an interleukin-2 signaling domain, such as an IL2Rb or an IL2Rg domain. In some embodiments, the extracellular binding domain is a binding domain that binds to rapamycin or a rapalog, comprising FKBP or FRB or a portion thereof. In some embodiments, the cell is a CD8+ or a CD4+ cell. In some embodiments, the cell is a CD8+ T cytotoxic lymphocyte cell selected from the group consisting of naïve CD8+ T-cells, central memory CD8+ T-cells, effector memory CD8+ T-cells and bulk CD8+ T-cells. In some embodiments, the cell is a CD4+ T helper lymphocyte cell that is selected from the group consisting of naïve CD4+ T-cells, central memory CD4+ T-cells, effector memory CD4+ T-cells, and bulk CD4+ T-cells. In some embodiments, the cell is a precursor T-cell. In some embodiments, the cell is a stem cell. In some embodiments, the cell is a hematopoietic stem cell. In some embodiments, the cell is a B cell. In some embodiments, the cell is a neuronal stem cell. In some embodiments, the cell is an NK cell.

Method of Activating a Signal in the Interior of a Cell

In some embodiments, a method of activating a signal in the interior of a cell, such as a mammalian cell, is provided. The method can include providing a cell, such as a mammalian cell, as described herein, wherein the cell comprises a protein sequence as set forth herein or an expression vector as set forth herein. In some embodiments, the method further comprises expressing the protein sequence encoding a dimeric CISC as described herein, or expression the vector as described herein. In some embodiments, the method comprises contacting the cell, such as a mammalian cell, with a ligand, which causes the first and second CISC components to dimerize, which transduces a signal into the interior of the cell. In some embodiments, the ligand is rapamycin or rapalog. In some embodiments, the ligand is an IMID-class drug (e.g. thalidomide, pomalidomide, lenalidomide or related analogues). In some embodiments an effective amount of a ligand for inducing dimerization is provided an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

In some embodiments, the ligand used in these approaches is rapamycin or a rapalog, comprising, for example, everolimus, CCI-779, C20-methallylrapamycin, C16-(S)-3-methylindolerapamycin, C16-iRap, AP21967, sodium mycophenolic acid, benidipine hydrochloride, AP23573, or AP1903, or metabolites, derivatives, and/or combinations thereof. Additional useful rapalogs may include, for example, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and/or alternative substitution on the cyclohexyl ring or replacement of the cyclohexyl ring with a substituted cyclopentyl ring. Additional useful rapalogs may include novolimus, pimecrolimus, ridaforolimus, tacrolimus, temsirolimus, umirolimus, or zotarolimus, or metabolites, derivatives, and/or combinations thereof. In some embodiments, the ligand is an IMID-class drug (e.g. thalidomide, pomalidomide, lenalidomide or related analogues).

In some embodiments, detecting a signal in the interior of the cell, such as a mammalian cell, can be achieved by a method of detecting a marker that is the result of a signaling pathway. Thus, for example, a signal may be detected by determining the levels of Akt or other signaling marker in a cell, such as a mammalian cell, through a process of Western blot, flow cytometry, or other protein detection and quantification method. Markers for detection may include, for example, JAK, Akt, STAT, NF-κ, MAPK, PI3K, INK, ERK, or Ras, or other cellular signaling markers that are indicative of a cellular signaling event.

In some embodiments, transduction of a signal affects cytokine signaling. In some embodiments, transduction of the signal affects IL2R signaling. In some embodiments, transduction of the signal affects phosphorylation of a downstream target of a cytokine receptor. In some embodiments, the method of activating a signal induces proliferation in CISC-expressing cells, such as mammalian cells, and a concomitant anti-proliferation in non-CISC expressing cells.

Figure 4A:
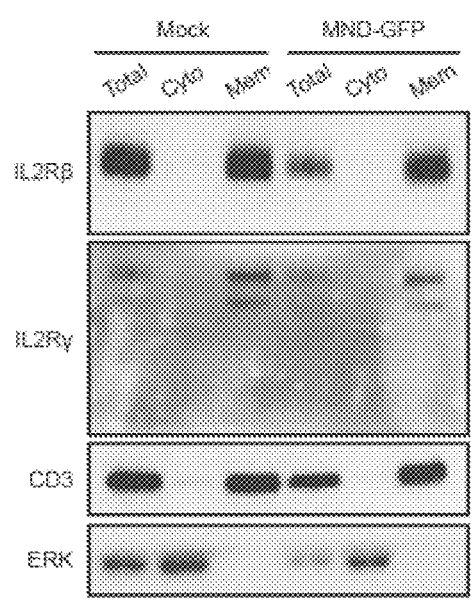
FIG. 4A and FIG. 4B show images of Western blots. IL2R-CISC human CD4+ T cells were harvested two days post transduction, and the cytoplasmic and membrane fractions were isolated. The top panel is a control to demonstrate that the methods used efficiently fractionate cytosol and membrane: the top gel shows IL2Rβ; the middle gel shows IL2Rγ; and bottom two gels are control gels showing CD3 and ERK.
Figure 4B:
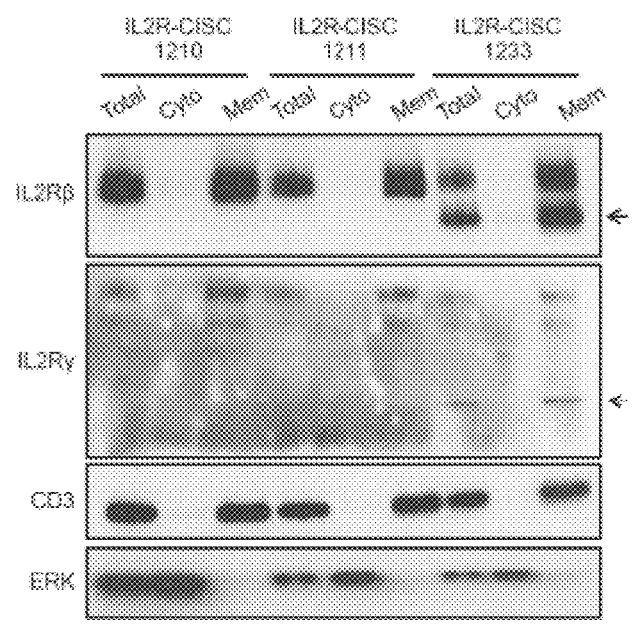
Figure 5:
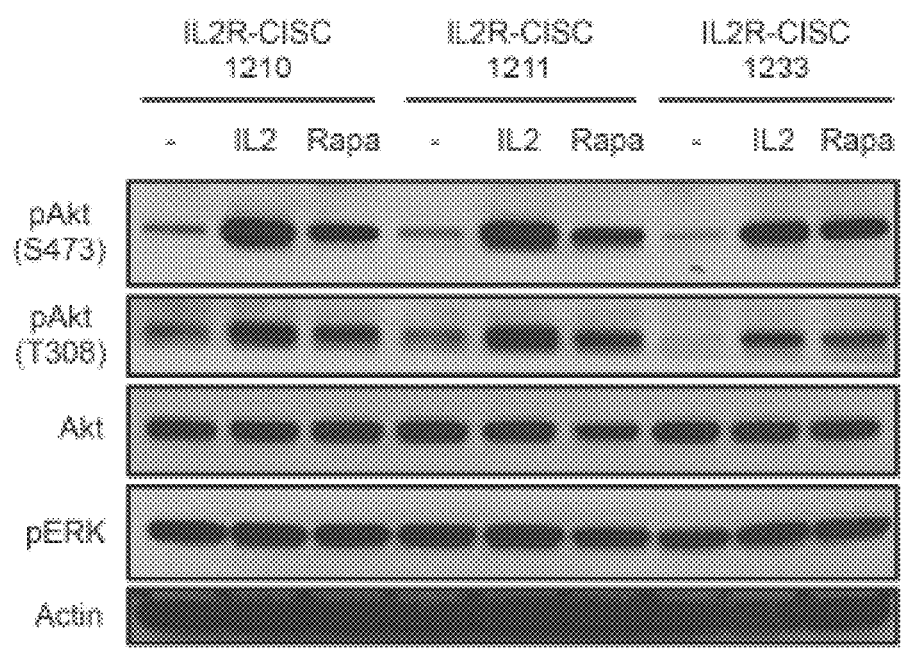
FIG. 5 shows an image of a Western blot for IL2R-CISC. IL2R-CISC human CD4+ T cells were analyzed following 15 days of rapamycin treatment at 1 nM, following by cytokine starvation for 48 hours. Stimulation with IL-2 (50 ng) or rapamycin (100 nM) for 20 minutes was followed, and the cells were harvested for Western blot. The Western blot shows Akt activation, indicating the capacity for a chemical-induced signaling complex to drive cell expansion.

For cellular signaling to take place, not only must cytokine receptors dimerize or heterodimerize, but they must be in the proper configuration for a conformational change to take place (Kim, et al. *NMR Structural Studies of Interaction of a Small, Nonpeptidyl Tpo Mimic with the Thrombopoietin Receptor Extracellular Juxtamembrane and Transmembrane Domains*, J Biol Chem, 282, 2007). Thus, dimerization in conjunction with the correct conformational positioning of signaling domains are desired processes for appropriate signaling, because receptor dimerization or heterodimerization alone is insufficient to drive receptor activation. The chemical-induced signaling complexes described herein are preferably in the correct orientation for downstream signaling events to occur. As shown in the Western blots of FIGS. 4A-4B and 5, multiple downstream signaling events occur in the presence of a ligand, including both Akt activation (required for driving cell proliferation), a feature that indicates successful orientation, and dimerization of the signaling complexes described herein.

Method of Selective Expansion of Cell Populations

In some embodiments, a method of selectively expanding a population of cells, such as mammalian cells, is provided herein. In some embodiments, the method comprises providing a cell, such as a mammalian cell, as described herein, wherein the cell comprises a protein sequence as set forth herein or an expression vector as set forth herein. In some embodiments, the method further comprises expressing the protein sequence encoding a dimeric CISC as described herein, or expression the vector as described herein. In some embodiments, the method comprises contacting the cell, such as a mammalian cell, with a ligand, which causes the first and second CISC components to dimerize, which transduces a signal into the interior of the cell. In some embodiments, the ligand is rapamycin or rapalog. In some embodiments an effective amount of a ligand provided for inducing dimerization is an amount of 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, 10, 11, 12, 13, 14, 15, 20, 25, 30, 35, 40, 45, 50, 55, 60, 65, 70, 75, 80, 85, 90, 95, or 100 nM or a concentration within a range defined by any two of the aforementioned values.

In some embodiments, the ligand used is rapamycin or a rapalog, comprising, for example, everolimus, CCI-779, C20-methallylrapamycin, C16-(S)-3-methylindolerapamycin, C16-iRap, AP21967, sodium mycophenolic acid, benidipine hydrochloride, or AP23573, AP1903, or metabolites, derivatives, and/or combinations thereof. Additional useful rapalogs may include, for example, variants of rapamycin having one or more of the following modifications relative to rapamycin: demethylation, elimination or replacement of the methoxy at C7, C42 and/or C29; elimination, derivatization or replacement of the hydroxy at C13, C43 and/or C28; reduction, elimination or derivatization of the ketone at C14, C24 and/or C30; replacement of the 6-membered pipecolate ring with a 5-membered prolyl ring; and/or alternative substitution on the cyclohexyl ring or replacement of the cyclohexyl ring with a substituted cyclopentyl ring. Additional useful rapalogs may include novolimus, pimecrolimus, ridaforolimus, tacrolimus, temsirolimus, umirolimus, or zotarolimus, or metabolites, derivatives, and/ or combinations thereof. In some embodiments, the ligand is an IMID-class drug (e.g. thalidomide, pomalidomide, lenalidomide or related analogues).

In some embodiments, the selective expansion of a population of cells, such as mammalian cells, takes place only when two distinct genetic modification events have taken place. One genetic modification event is one component of the dimeric chemical-induced signaling complex, and the other genetic modification event is the other component of the dimeric chemical-induced signaling complex. When both events take place within the population of cells, such as a population of mammalian cells, the chemical-induced signaling complex components dimerize in the presence of a ligand, resulting in an active chemical-induced signaling complex and generation of a signal into the interior of the cells. The activation and phosphorylation of Akt, as shown in the Western blot in FIG. 5, indicates successful achievement of a full proliferative signal, which is desired to achieve a significant selective expansion of the cell population expressing both genetic modification events. Other signaling markers may also be detected, but only achievement of these events in conjunction with Akt activation is able to achieve sufficient cellular expansion to allow for selective expansion of a modified cell population in which both genetic modification events have taken place in a given population of cells, such as a population of mammalian cells.

Figure 6:
FIG. 6 outlines the experiment demonstrating use of an IL2R-CISC to selectively expand a cell population. Each architecture of IL2R-CISC (i.e. 1210, 1211, and 1233) was cis-linked together with GFP using 2A sequences, and placed under the control of an MND promoter in a lentiviral expression cassette (as schematized in FIG. 5, bottom). Lentiviral particles from each IL2R-CISC architecture were generated and used to transduce primary human T-cells. Following transduction, the cells were grown for 2 days in IL2, and then divided in half, with half grown in IL2 alone and half in rapamycin alone, as indicated.
Figure 7A:
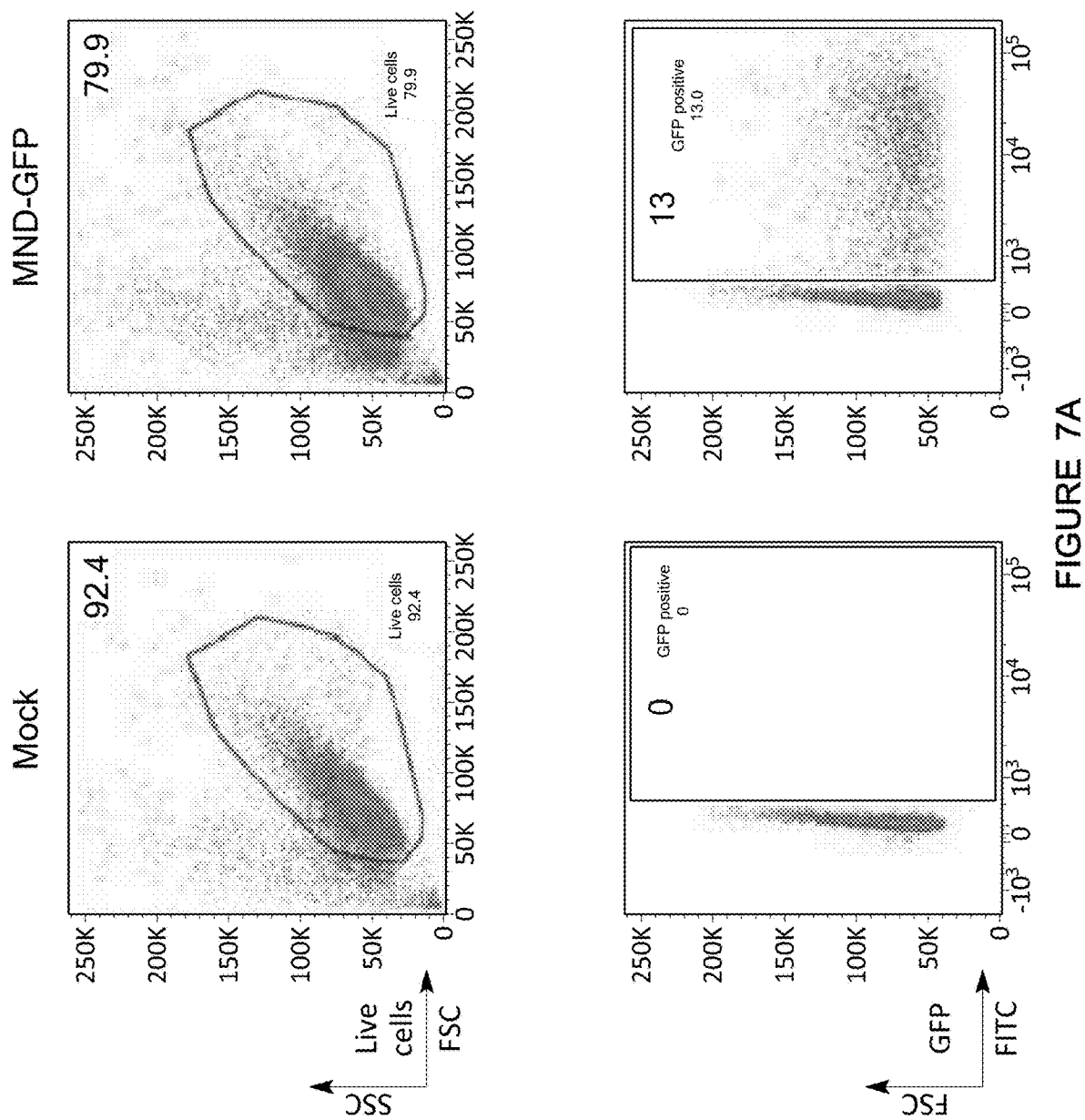
FIG. 7A demonstrates efficient transduction of T-cells using a lentiviral vector driving expression of GFP alone.
Figure 7B:
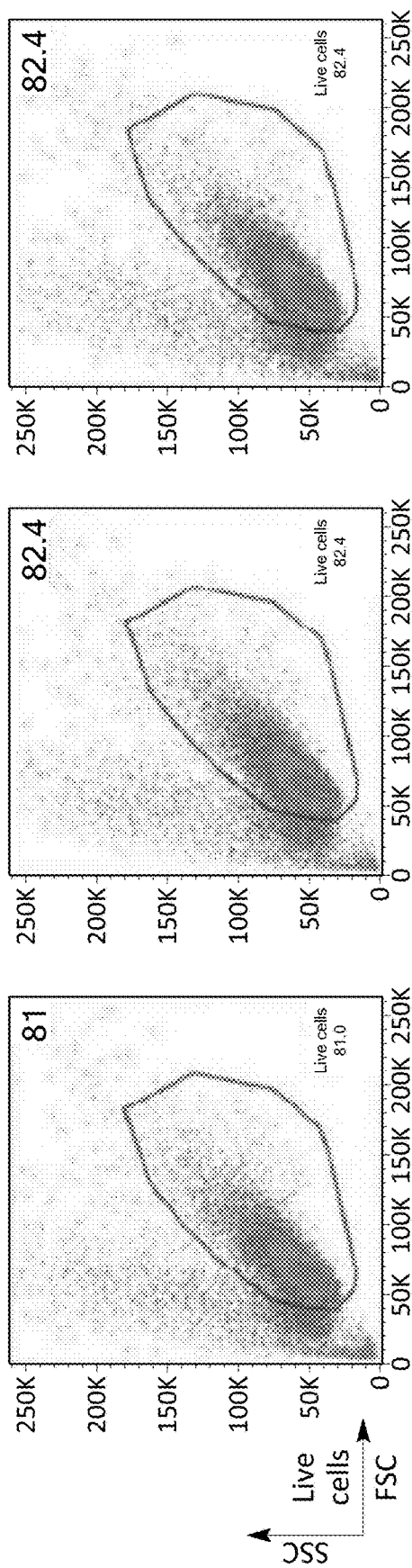
FIG. 7B shows the expression of 1210, 1211, and 1233 expressed using a vector outlined at the bottom of FIG. 3—MND-IL2Rb-CISC-2A-IL2Rg-CISC-2A-GFP, as compared to mock and MND-GFP retroviral vector. T cells were activated for 48 hours and then incubated for 28 hours. T cells were plated with IL-2/7/15. Lentiviral transduction included IL2-CISC of MND-GFP control with protamine sulfate. Transduced cells were incubated at 37° C. for 24 hours with cytokine (IL-2, 50 ng/mL; IL-5, 5 ng/mL; IL-17, 5 ng/mL). IL2-CISC expression was determined by GFP expression using flow cytometry.

FIG. 6 provides an exemplary method for the selective expansion of a cell population, such as a population of mammalian cells. As shown in FIG. 6, a CISC including IL2R was prepared. Each architecture of IL2R-CISC (i.e. 1210, 1211, and 1233) was cis-linked together with GFP using 2A sequences, and placed under the control of an MND promoter in a lentiviral expression cassette.

Lentiviral particles from each IL2R-CISC architecture were generated and used to transduce primary human T-cells. CD4+ T cells were activated for 60 hours. The cells were then plated in a 24-well dish by plating 1 million cells per well in 1 mL medium with IL2/7/15. Lentivirus was transduced with or without beads, using 15 µL of IL2R-CISC and 3 µL of MND-GFP control with protamine sulfate at 4 µg/mL (0.5 mL medium) in a 24-well dish. The cells were then spinoculated at 800 g for 30 minutes at 33° C. followed by the addition of 1.5 mL medium after 4 hours of incubation. The transduced T cells were incubated at 37° C. for 48 hours with cytokines, including 50 ng/mL IL2, 5 ng/mL of IL5, and 5 ng/mL of IL17. The GFP signal was determined and the IL2R-CISC level of transduced T cells was determined. The transduction efficiency was from 10-30% for IL2R-CISC and about 80% for MND-GFP.

Figure 8:
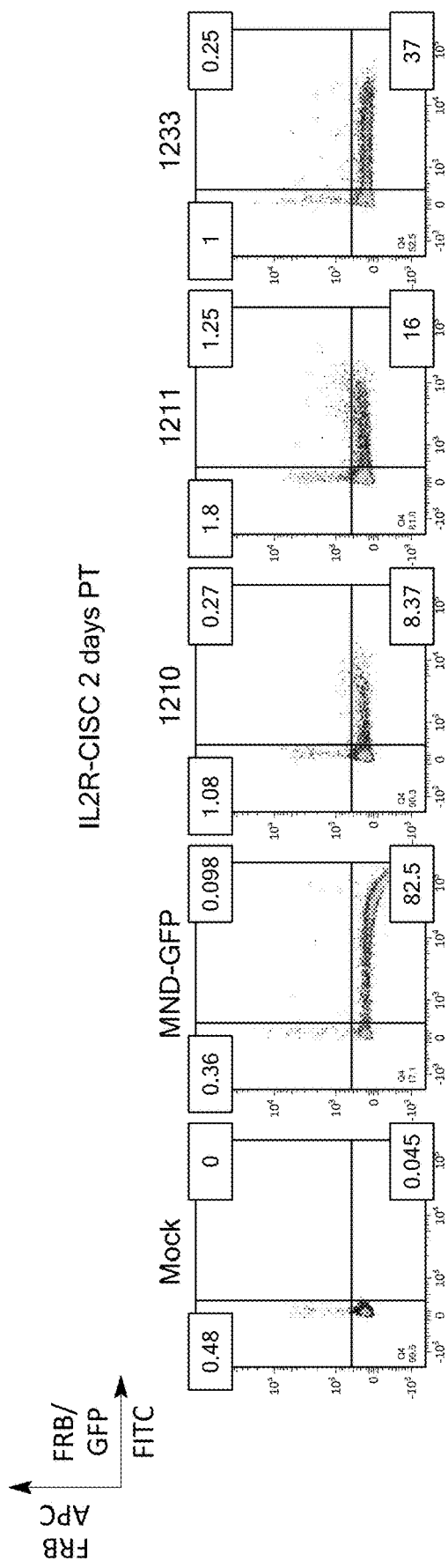
FIG. 8 shows flow analysis of cells. Top flow panels show Flow Analysis of cells for GFP expression (X-axis) and FRB expression (the extracellular domain of the IL2Rg-CISC component, Y-axis) at 2 days (just prior to placing cells into IL2 or rapamycin cultures). Bottom two flow panels show Flow Analysis of cells for GFP expression (X-axis) and FRB expression 4 days post transduction, 2 days following division into culture in IL2 alone (top panels), or rapamycin (bottom panel). Note that in particular for 1233 (bottom right flow panel), cells cultured in rapamycin alone are beginning to enrich for IL2R-CISC expression as read out by the cis-linked GFP marker.
Figure 9:
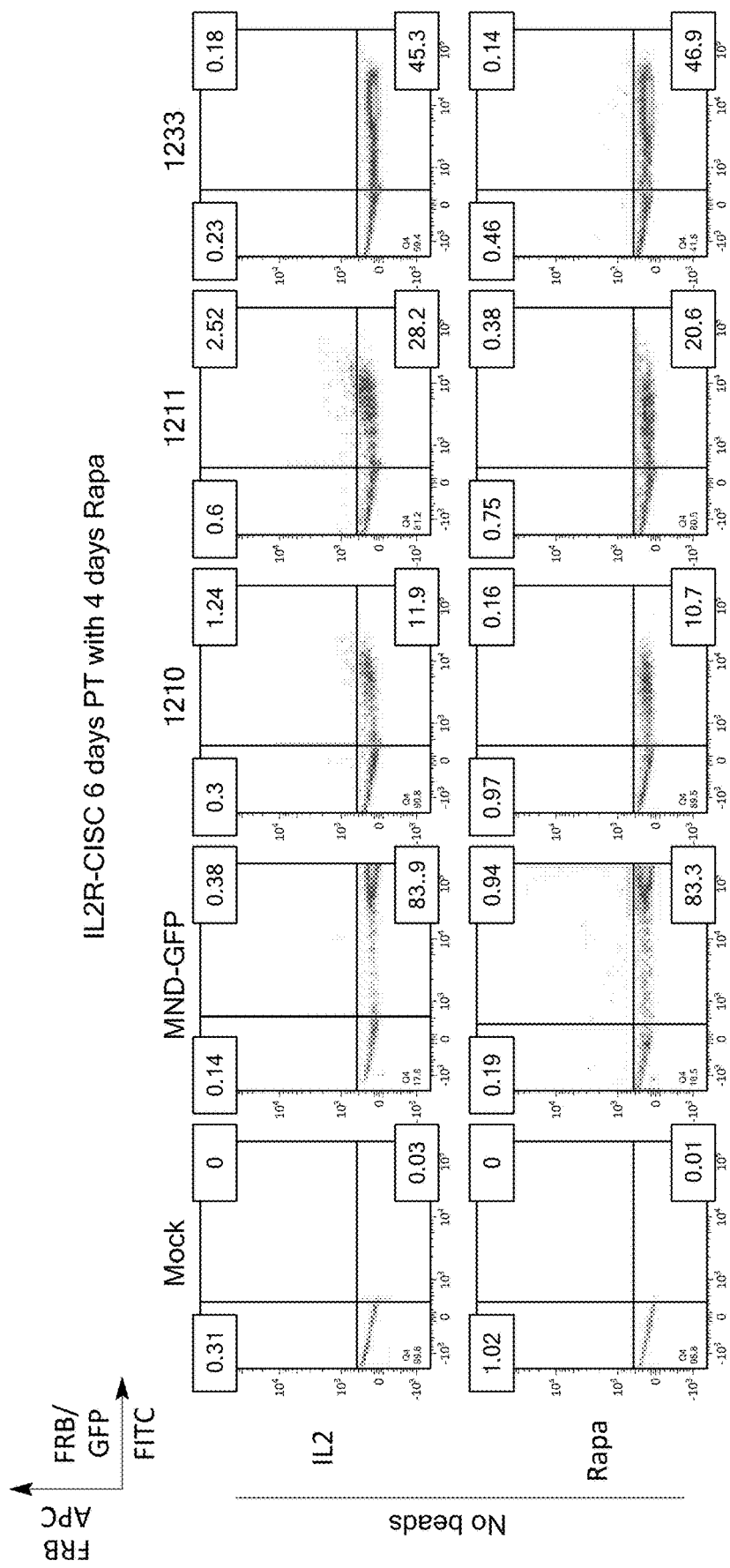
FIG. 9 shows flow analysis of cells. Top two flow panels show Flow Analysis of cells for GFP expression (X-axis) and FRB expression 6 days post transduction, 4 days following division into culture in IL2 alone (top panels), or rapamycin (bottom panel). Note the further enrichment of the GFP marker for 1233. Bottom two flow panels show Flow Analysis of cells for GFP expression (X-axis) and FRB expression 9 days post transduction, 7 days following division into culture in IL2 alone (top panels), or rapamycin (bottom panel). Note the further enrichment of the 1233 GFP+ cells.
Figure 10:
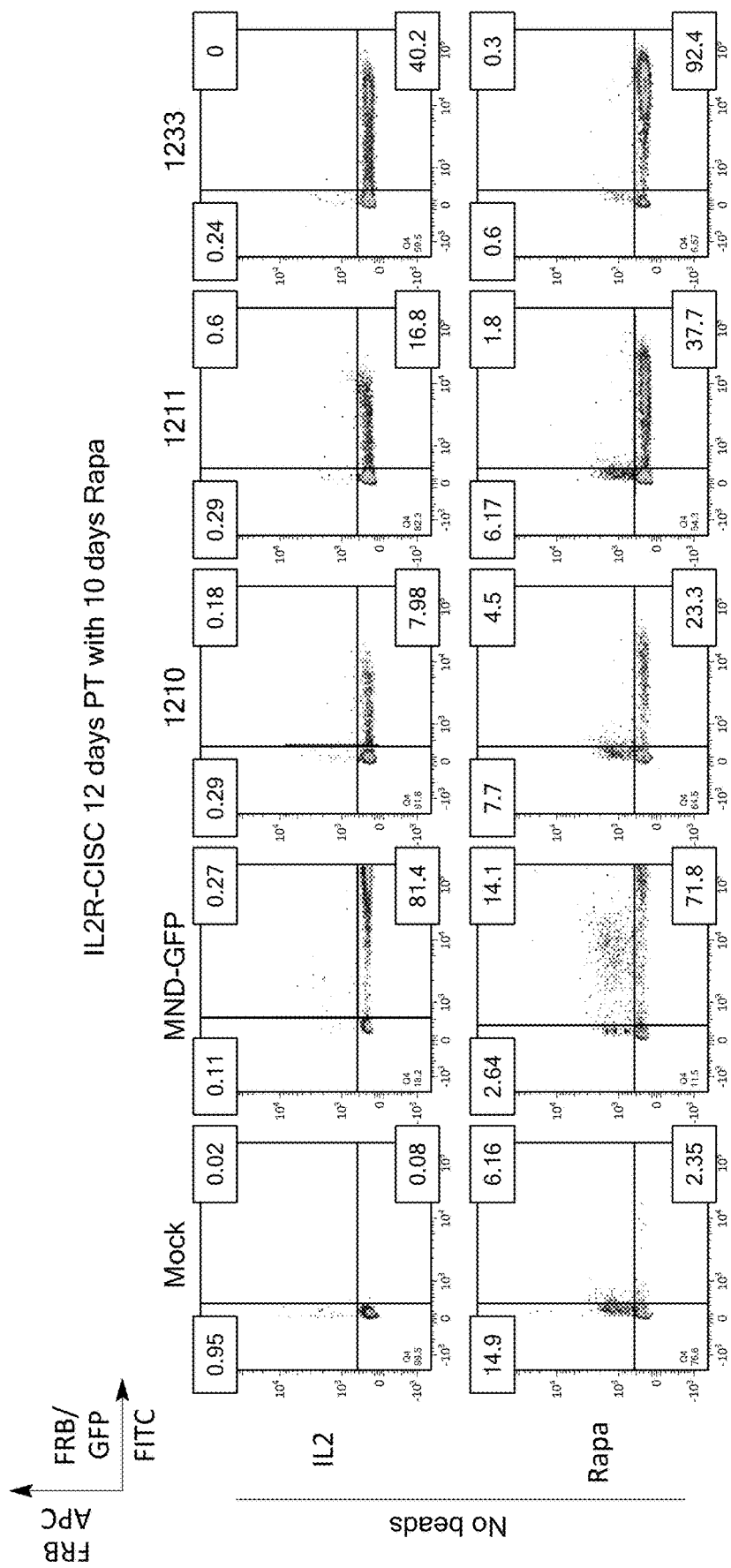
FIG. 10 shows flow analysis of cells. Top two flow panels show Flow Analysis of cells for GFP expression (X-axis) and FRB expression 12 days post transduction, 10 days following division of culture in IL2 alone (top panels), or rapamycin (bottom panel). Bottom two flow panels show Flow Analysis of cells for GFP expression (X-axis) and FRB expression 17 days post transduction, 15 days following dividing into culture in IL2 alone (top panels), or rapamycin (bottom panel). Cells expressing the 1233 IL2R-CISC are now enriched to 97% of the cell population (far bottom right flow panel).
Figure 11:
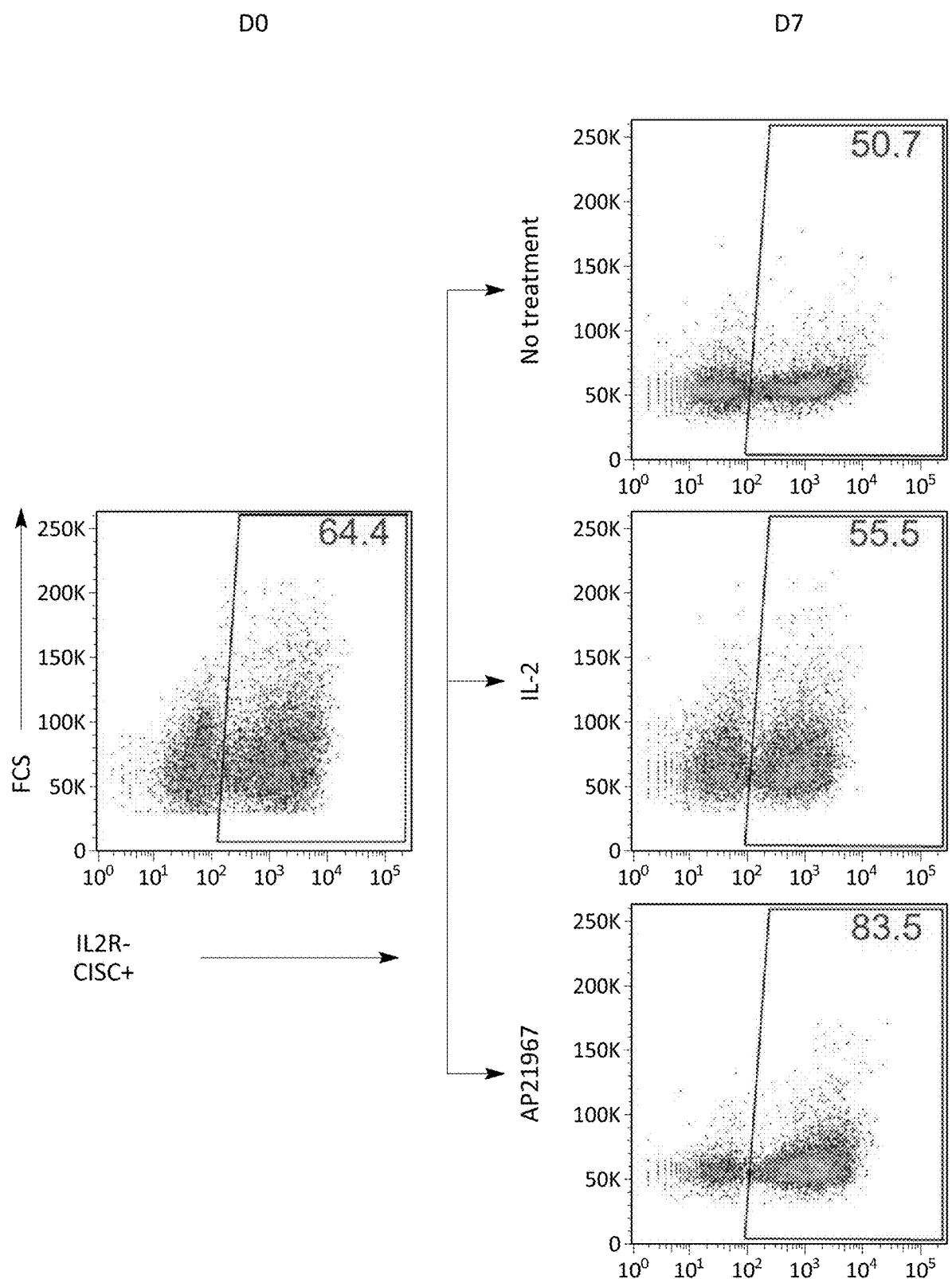
FIG. 11 demonstrates the enrichment of IL2R-CISC V3 expressing cells over the course of 15 days of an experiment as outlined in FIG. 6, but carried out for 25 days. The leftmost single panel represents the cells at the start of rapamycin treatment. Each row of panels represents a different treatment. As can be seen in the bottom row, by 15 days, the IL2R-CISC V3 cells had enriched from a starting transduced population of 64% mCherry positive to >93% mCherry positive when cultured in rapamycin. In contrast, mock IL-2 treatments resulted in a gradual reduction in mCherry positive cells.

Following transduction, the cells were grown for 2 days in IL2, and then divided in half, with half grown in IL2 alone and half in rapamycin alone, as indicated. T cells were treated with rapamycin (1 nM) or IL2 for 2 days, and cells were plated at 1 million cells/well in a 24-well dish with 2 mL medium. The T cell viability was determined and the expression of GFP+ population and IL2R-CISC expression was determined by using anti-FRB antibody and a secondary APC antibody. FIGS. 7A-7B, and 8-11 show the flow cytometry results of the expression of GFP and FRB in the respective populations. As shown in FIG. 8, for the 1233 architecture, cells cultured in rapamycin alone are enriched for IL2R-CISC expression as read out by the cis-linked GFP marker.

Figure 12:
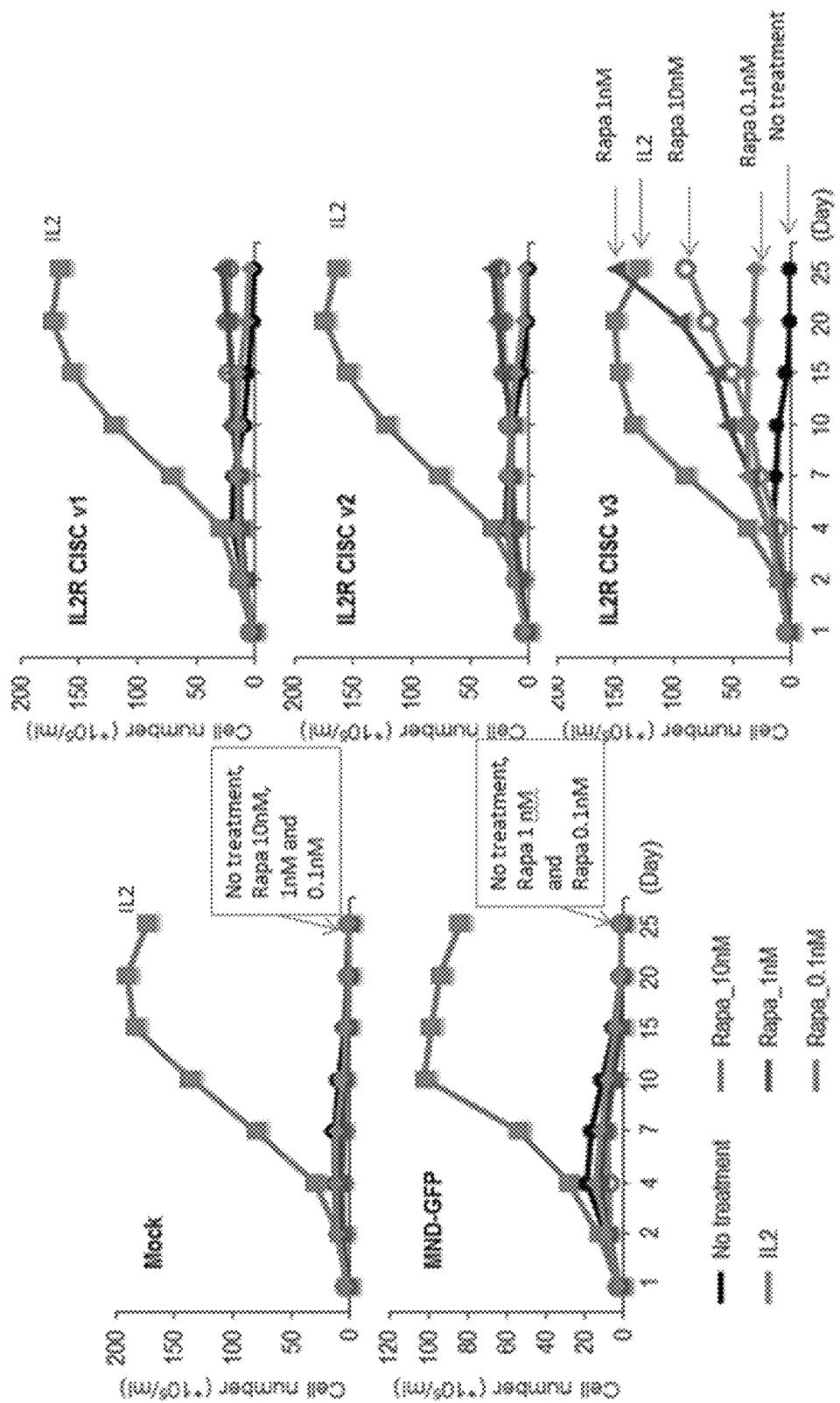
FIG. 12 shows expansion of mCherry positive cell numbers, using the same experimental paradigm as outlined in FIG. 6, but carried out for 25 days. The cell type is indicated in bold in the upper left corner of each panel. Each curve indicated by different symbols delineates a different treatment/culture condition maintained for the 25 days.
Figure 13:
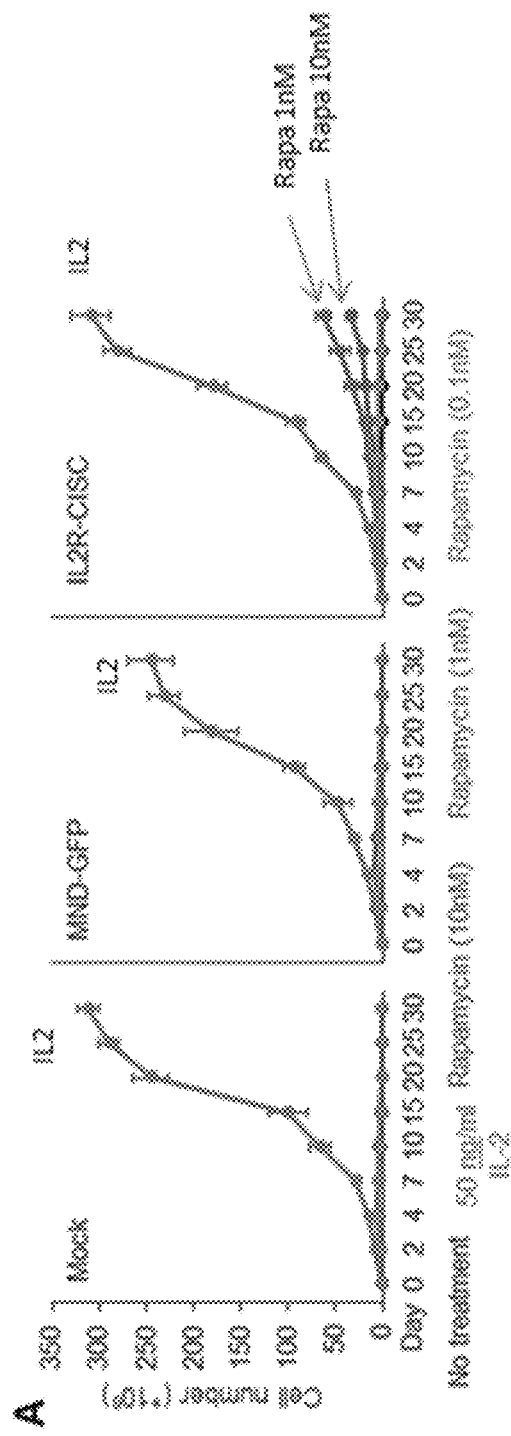
FIG. 13 shows expansion of mock, GFP, or IL2R-CISC V3 expressing cells, using the same experimental paradigm as outlined in FIG. 6, but carried out for 30 days, and utilizing two different rapamycin doses, 1 nM and 10 nM. The cell type is indicated in bold in the upper left corner of each panel. Each curve indicated by different symbols delineates a different treatment/culture condition maintained over the course of the experiment.

FIG. 12 graphically shows the increase in cell proliferation in the presence of rapamycin for the CISC constructs depicted in FIG. 3. V3 is the most efficient architecture for proliferation. FIG. 13 graphically depicts that IL2R-CISC V3 supports human CD4+ T cell proliferation in response to rapamycin treatment.

Figure 14:
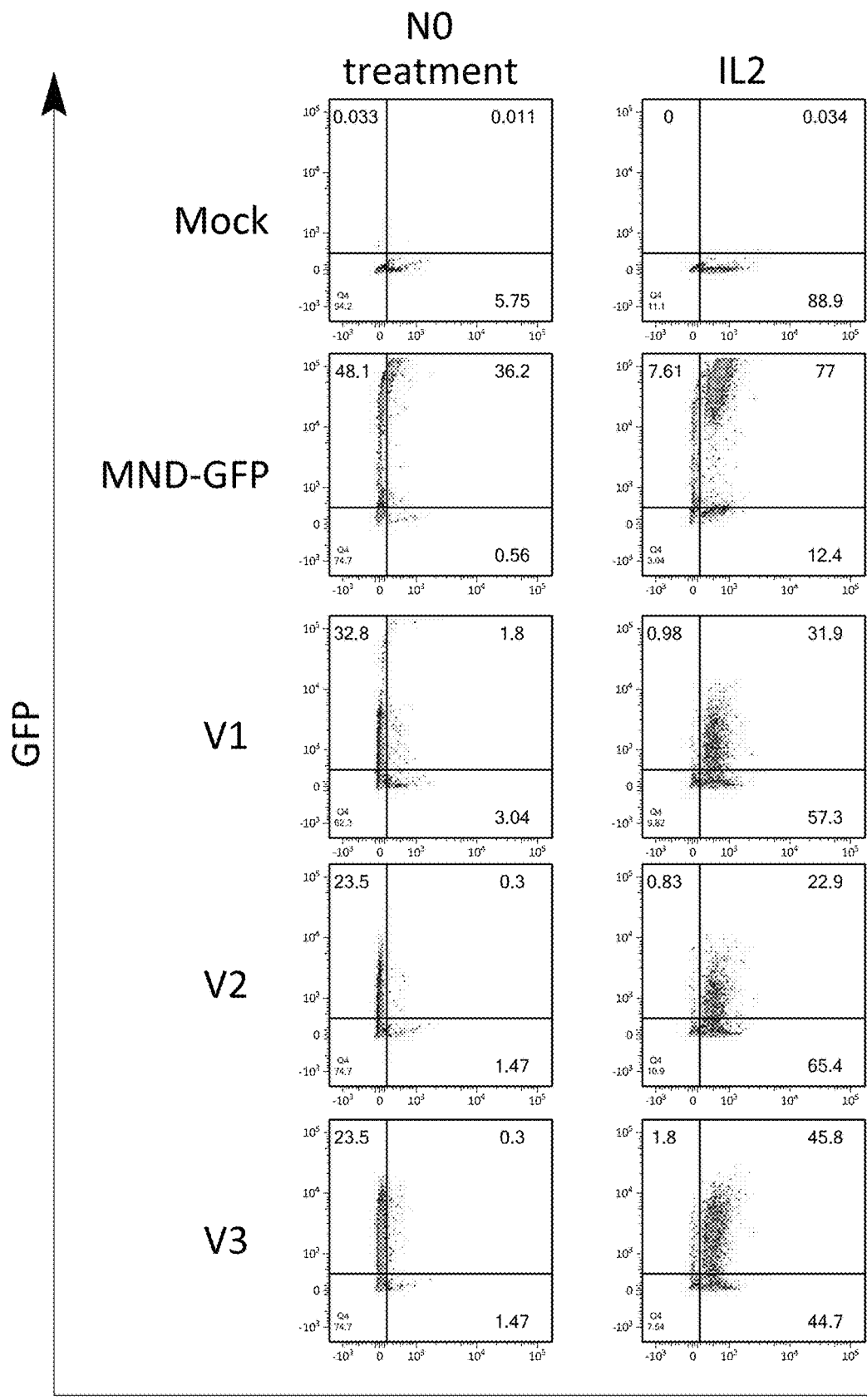
FIG. 14 shows analysis of phosphor-STAT5 signaling in response to the treatments indicated at the top of each column, for the cell types indicated for each row (after 20 days of culture in the indicated condition). As can be seen, cells that received "mock" treatment (row 1) are no longer responsive, as essentially no cells are alive after 20 days. In contrast, while all other cells respond robustly to IL-2 treatment, only IL2R-CISC expressing cells respond to rapamycin with phosphorylation of STAT5, and IL2R-CISC V3 expressing cells respond most robustly, confirming that the V3 architecture signals most effectively.

Using the method as described above also showed that 1L2R-CISC expressing T cells induce STAT5 pathway in the presence of rapamycin. As shown by the flow cell data in FIG. 14, the V3 construct is the most efficient architecture for STAT5 pathway signaling.

Figure 15:
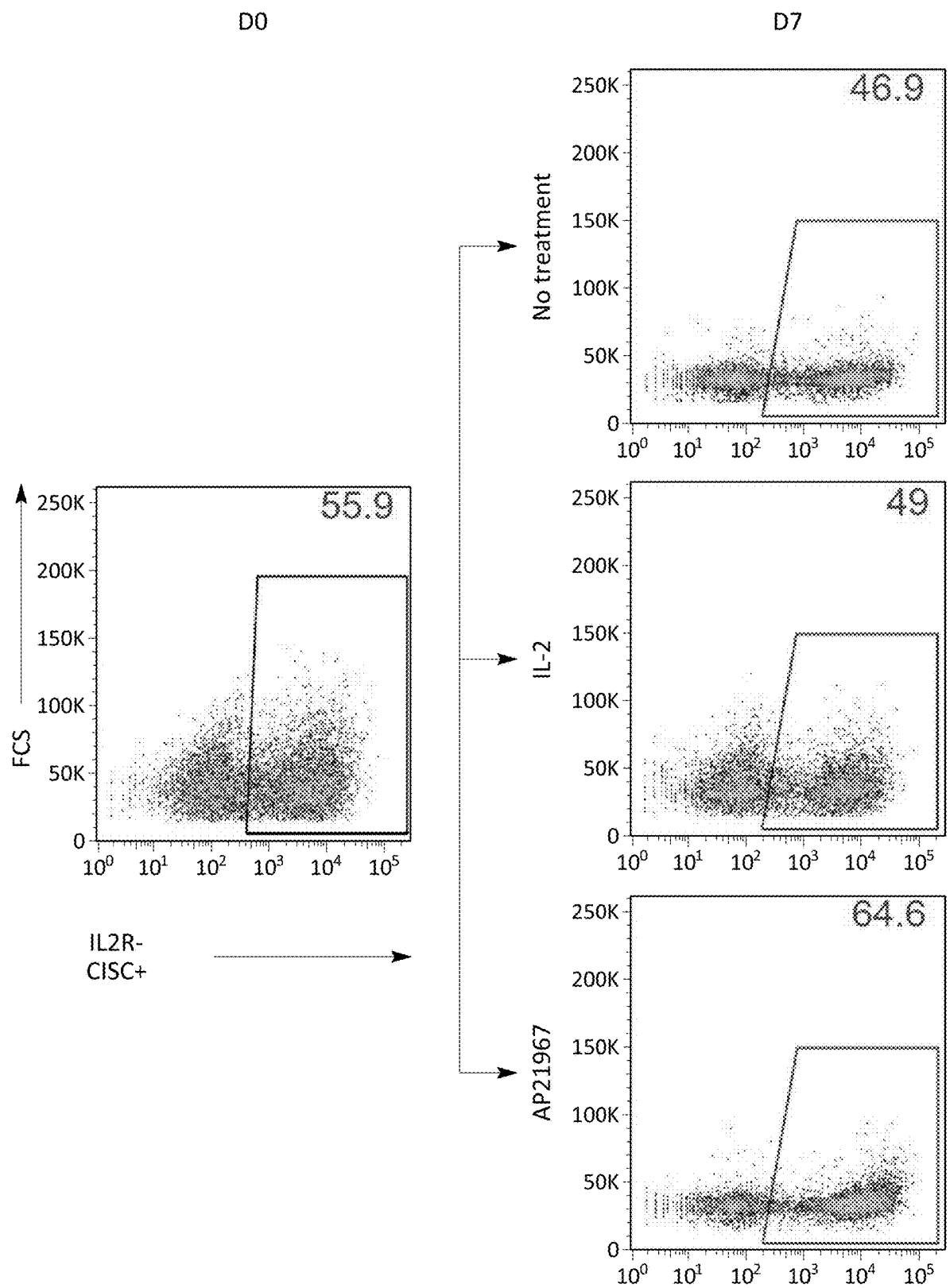
FIG. 15 demonstrates the enrichment of IL2R-CISC V3 expressing cells over the course of 15 days of an experiment identical to that in FIG. 11, except that AP21967 was used as the IL2R-CISC activating ligand. The leftmost single panel represents the cells at the start of AP21967 treatment. Each row of panels represents a different treatment. As can be seen in the bottom row, by 15 days, the IL2R-CISC V3 cells had enriched from a starting transduced population of 64% mCherry positive to >93% mCherry positive when cultured in AP21967. In contrast, mock IL-2 treatments resulted in a gradual reduction in mCherry positive cells.
Figure 16:
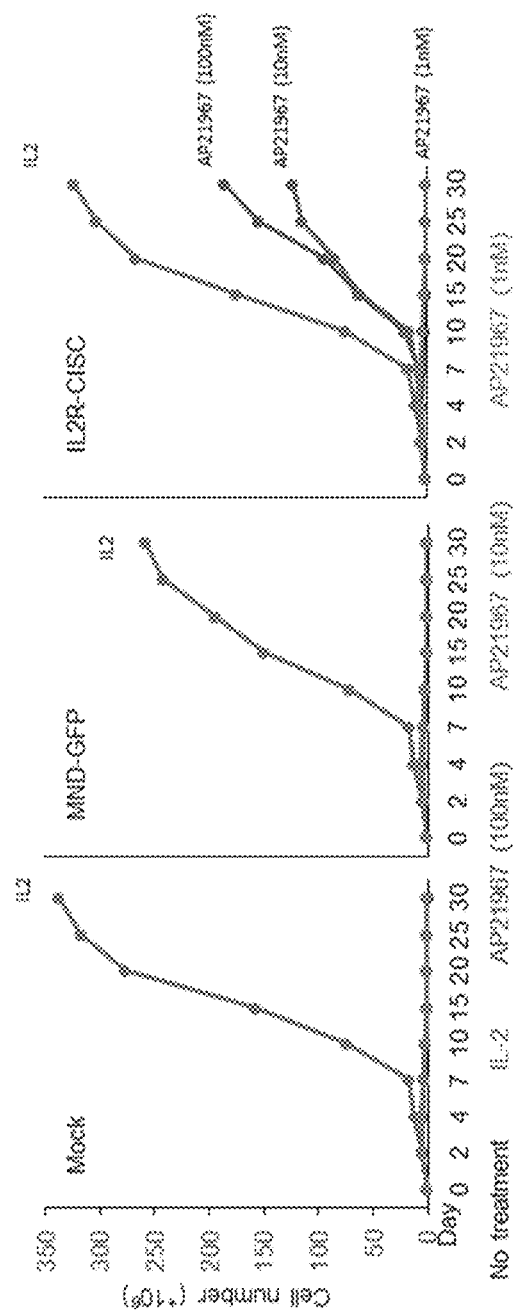
FIG. 16 shows expansion of mock, GFP, or IL2R-CISC V3 expressing cells, using the same experimental paradigm as outlined in FIG. 6, but carried out for 30 days, and utilizing two different AP21967 doses, 10 nM and 100 nM. The cell type is indicated in bold in the upper left corner of each panel. Each curve indicated by different symbols delineates a different treatment/culture condition maintained over the course of the experiment.
Figure 17:
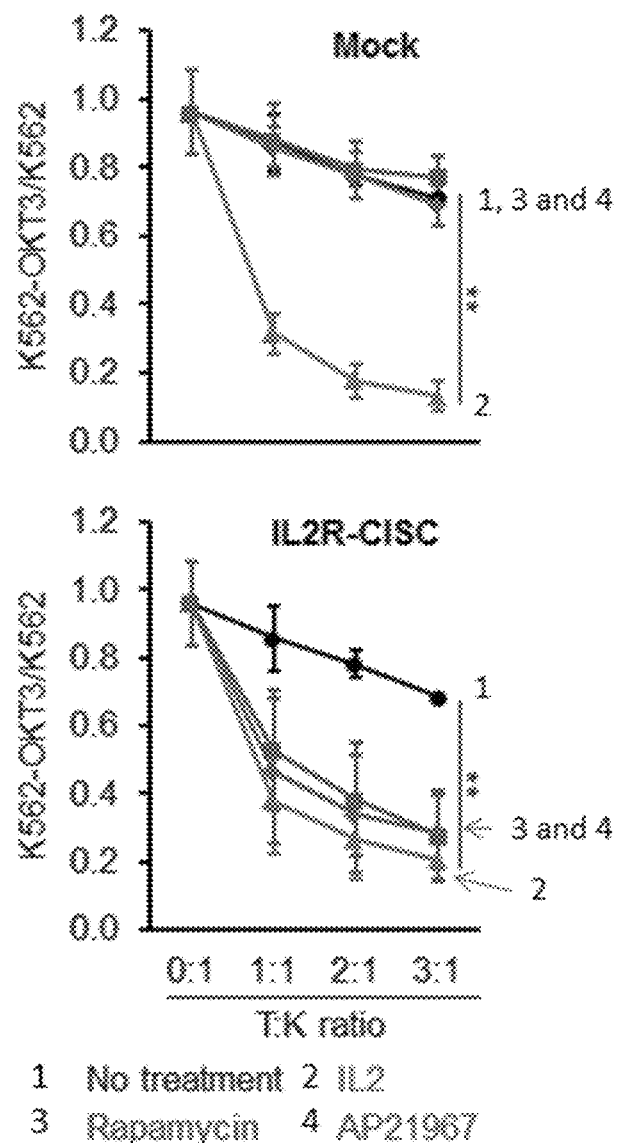
FIG. 17 shows cytolytic activity following expansion of IL2R-CISC V3 expressing cells in the indicated conditions for 15 days, using the experimental setup in FIG. 6, cells were transduced with IL2R-CISC V3 lentivirus, and expanded for 15 days. Cells were then incubated with K562 cells expressing anti-CD3. The expression of anti-CD3 by the target K562 cells causes clustering of CD3 on the T-cells upon contact with the K562 cell, resulting in cytolytic killing of the K562 cells. The IL2R-CISC V3 expressing T-cells expanded in the indicated condition were incubated at different target to killer ratios, and cytolysis was assessed by percent survival of the K562 target cells. Cells expanded through IL2R-CISC exhibited cytolytic activity that was statistically indistinguishable from cells expanded in IL-2.

Similar methods as described herein may be performed using additional rapamycin analogues. For example, the methods described herein were performed using AP21967. In response to AP21967, IL2R-CISC V3 construct promotes human CD4+ T cell survival, as shown in the flow cell data of FIG. 15. In addition, IL2R-CISC promotes CD4+ T cell proliferation in response to AP21967 treatment, as graphically depicted in FIG. 16. FIG. 17 shows the cytotoxicity of IL2R-CISC expanded CD4+ T cells with various treatments, including rapamycin and analogues thereof, indicating normal toxicity after long-term expansion.

Figure 18:
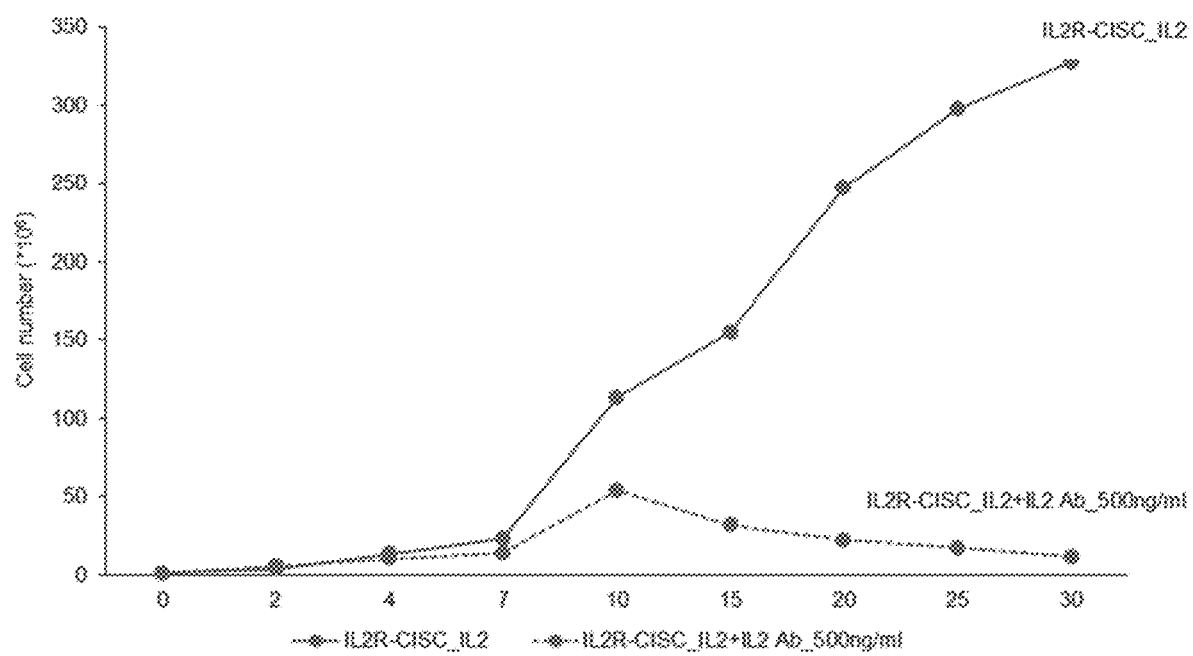
FIG. 18 shows that 500 ng/mL of anti-TL2 neutralizing antibody abrogates expansion of T-cells in IL-2. In this experiment, peripheral blood T-cells were activated using anti-CD3/CD28 beads, and expanded in IL-2 or in IL-2 plus anti-IL2 antibody. Use of the anti-IL2 antibody markedly inhibits expansion of the T-cells.
Figure 19:
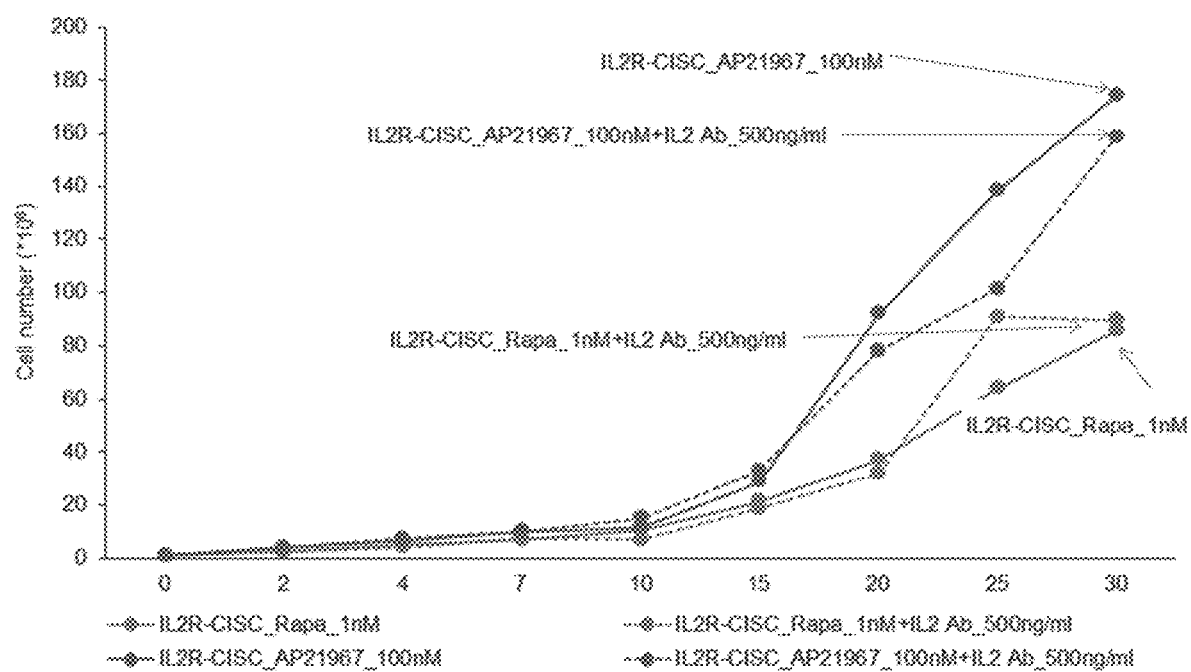
FIG. 19 shows that 500 ng/mL of anti-IL2 neutralizing antibody is unable to block the expansion of IL2R-CISC expressing T-cells cultured in an IL2R-CISC ligand (either rapamycin or AP21967). Peripheral blood T-cells were activated using anti-CD3/CD28 beads, transduced with IL2R-CISC V3 lentivirus, and expanded in the indicated IL2R-CISC ligand plus anti-TL2 antibody. Use of the anti-TL2 antibody did not inhibit expansion of the T-cells, demonstrating that the IL2R-CISC acts cell autonomously to provide a growth signal.

The IL2R-CISC cells were exposed to an IL-2 neutralizing antibody, which neutralized the growth and proliferation of cells (FIGS. 18 and 19). This indicates that the CISC-induced expansion is not due to autocrine or paracrine stimulation.

Figure 20:
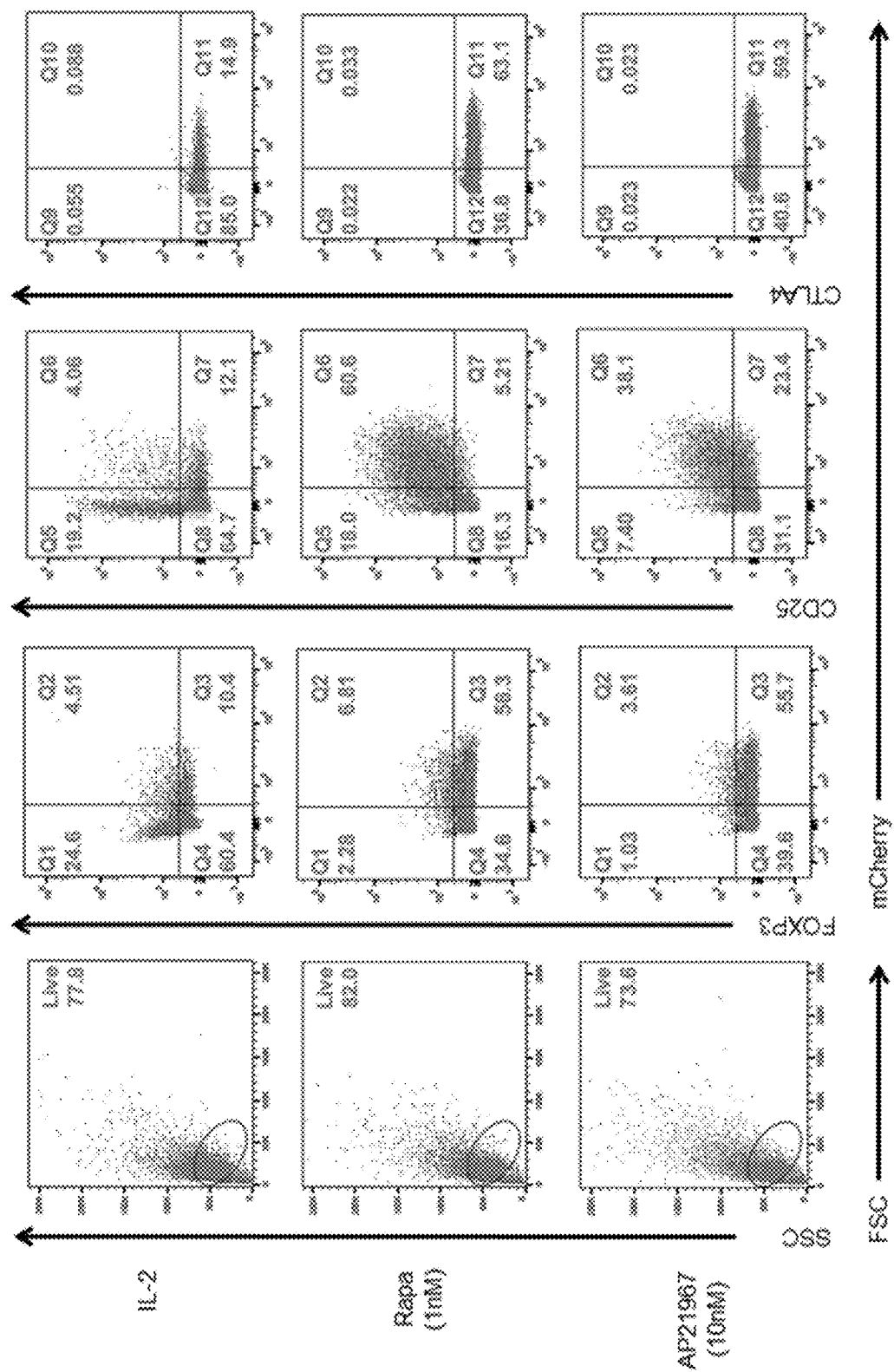
FIG. 20 shows a FACS assay that is a T-cell marker analysis for CISC V3 expanded cells. Peripheral blood T-cells were activated using anti-CD3/CD28 beads transduced with IL2R-CISC V3 lentivirus, expanded in IL-2 or the indicated IL2R-CISC ligand for 15 days. Cells expanded in IL-2 have generally low expression of CD25, the IL2R alpha subunit, reflecting TL2R turnover in response to IL-2. In contrast, cells expanded through their IL2R-CISC receptors have high CD25 expression, as low media IL-2 promotes minimal turnover of native IL2R.

The IL2-CISC induced signaling pathways were analyzed to determine whether the magnitude of the signaling pathway is sufficient to produce clinically relevant activity. A T-Cell marker analysis for CISC V3 expanded cells was performed, as shown in the flow cell data of FIG. 20.

Figure 21:
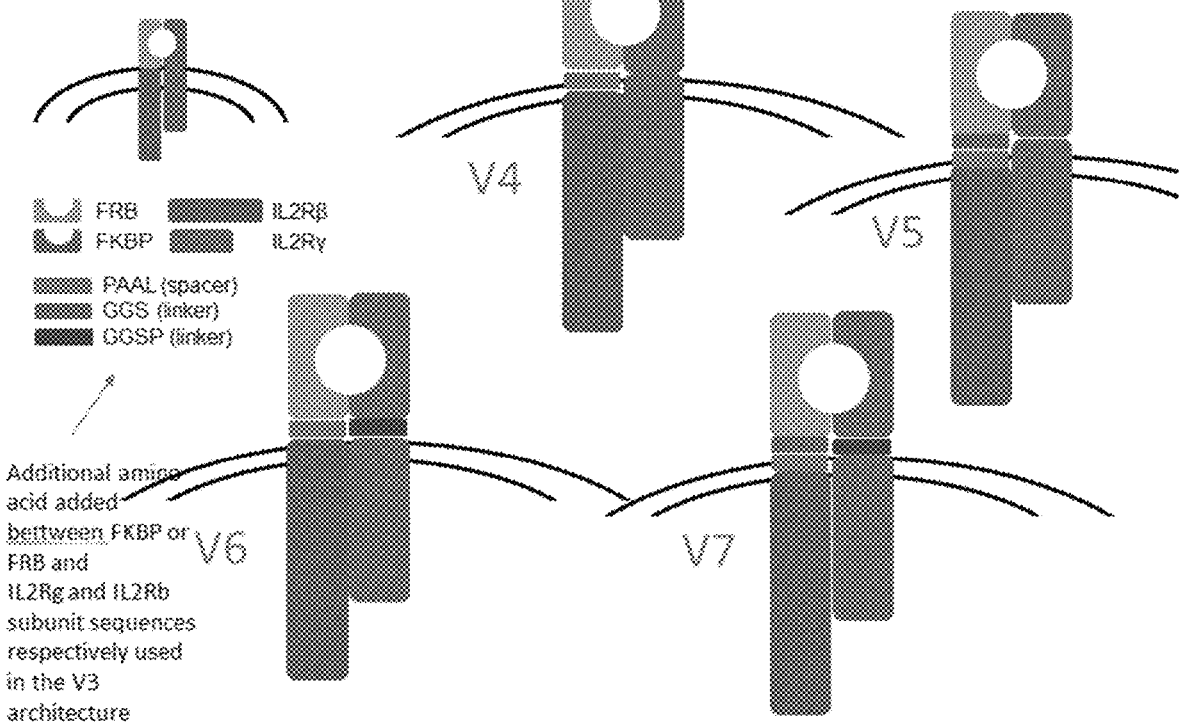
FIG. 21 shows a schematic of testing of additional CISC architectures with longer segments between IL2R components and chemical dimerizing domains (FRB, FKBP).
Figure 22:
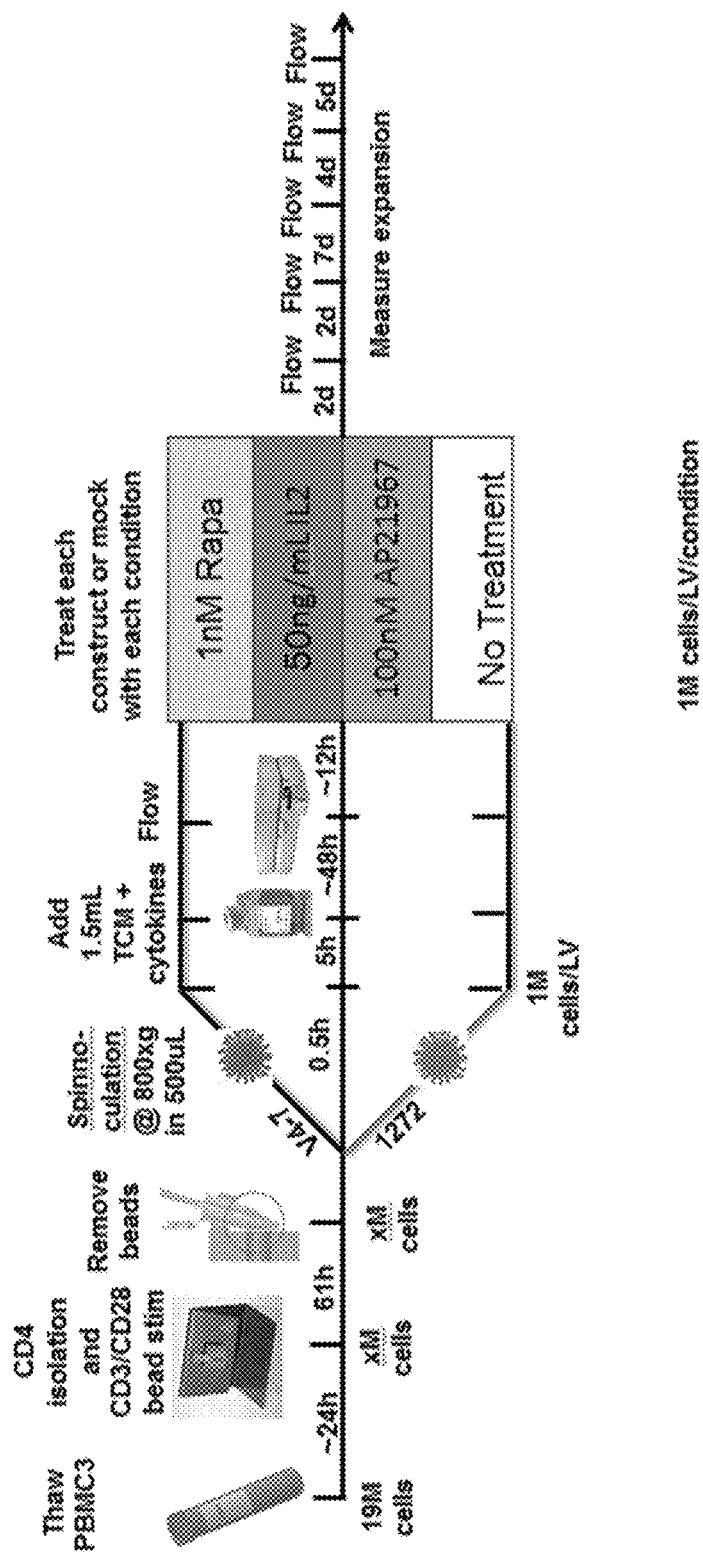
FIG. 22 shows the timeline and experimental design for treating the cells transduced by the lentiviral stock with longer IL2R-CISC linker architectures V4-V7.
Figure 23:
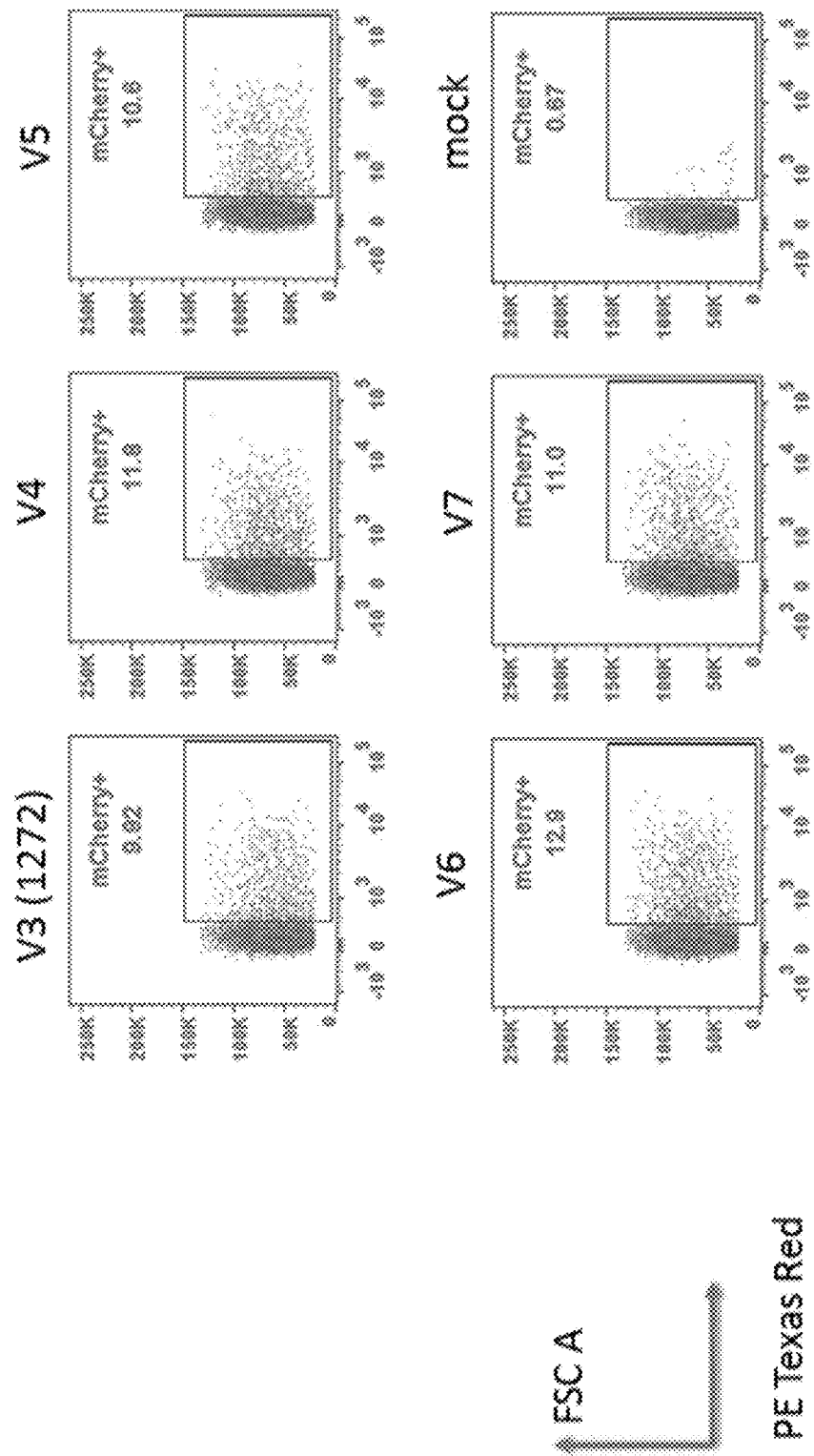
FIG. 23 shows the transduction efficiency of the lentiviral stock with longer IL2R-CISC linker architectures V4-V7 from FIG. 22.
Figure 24:
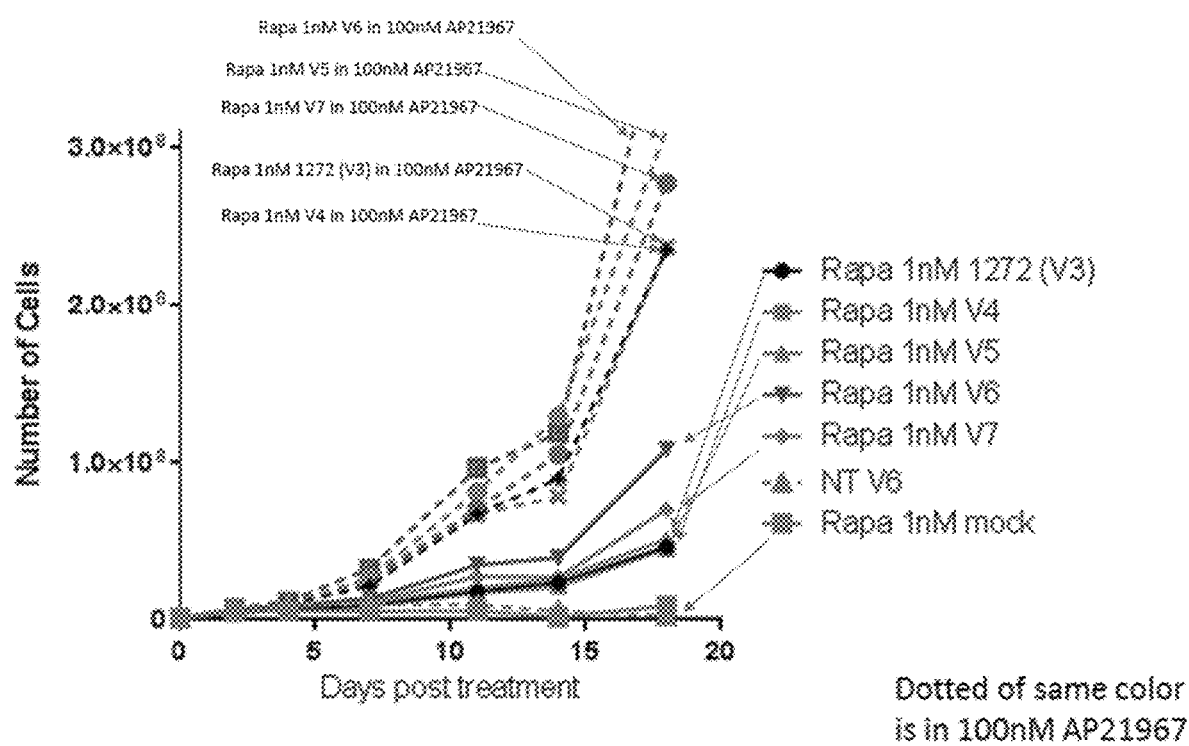
FIG. 24 shows that rapamycin-induced expansion is similar for all CISC architectures with expanded EC-domain to TM linkers. Peripheral blood T-cells were activated using anti-CD3/CD28 beads, transduced with IL2R-CISC V3-V7 lentivirus respectively, and expanded in the indicated IL2R-CISC ligand. The V3-V7 IL2R-CISC architectures were all able to induce T-cell expansion of comparable magnitude.

It is to be understood by those of skill in the art that the architectures and/or constructs described herein are not intended to be limiting. Thus, in addition to the V1, V2, and V3 constructs described herein, and other architectures and/or constructs described herein, additional architectures and/or may be used. For example, as shown in FIG. 21, additional constructs termed V4, V5, V6, and V7 were used, which included various spacers and linkers placed in the FKBP and/or FRB and IL2Rg and IL2Rb subunit sequences. The experimental protocol and design for using these comparative architectures is outlined in FIG. 22. Briefly, the method includes thawing a PBMC3 feeder cells, and CD4+ cells were isolated in the presence of anti-CD3/CD28 beads. The beads were removed, and spinoculated with one of V4, V5, V6, or V7 at 800×g in 500 µL. Following spinoculation, 1.5 mL TCM+ cytokines were added. Each construct was then treated with various conditions, including: no treatment, 100 nM AP21967, 1 nM rapamycin, or 50 ng/mL IL-2. The expansion of the cells having each construct was then measured. The expansion of the cells is shown in the flow cell data presented in FIG. 23. FIG. 24 graphically depicts the expansion of cells having the various constructs, and shows that rapamycin-induced expansion is similar for all CISC architectures tested with expanded EC-domain to TM linkers.

Figure 25:
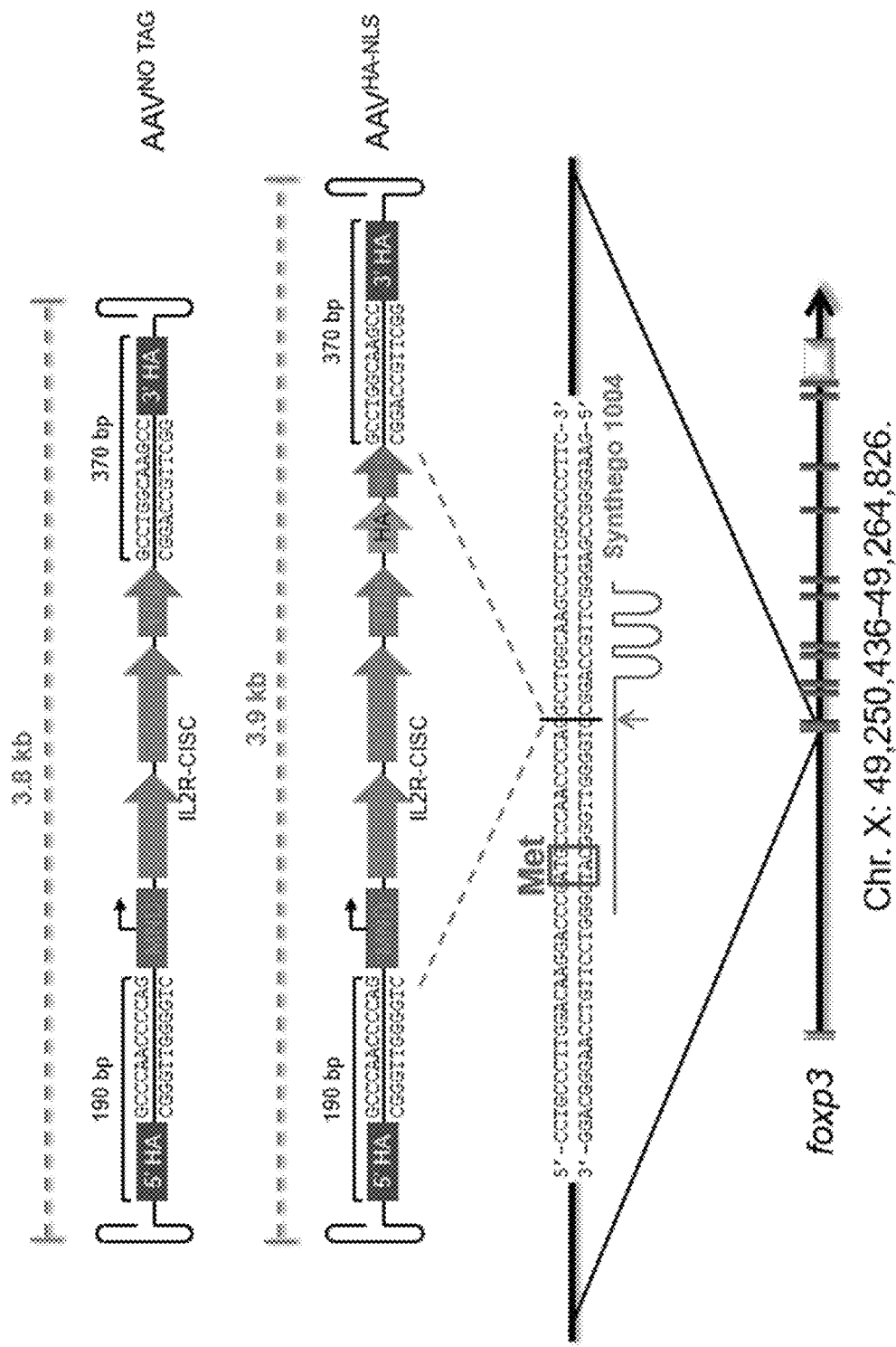
FIG. 25 shows a schematic of the Targeted knock-in of an MND promoter and CISC to enrich/expand gene targeted T-cells. The described targeting approach integrates a promoter and both components of an IL2R-CISC V3 into the FOXP3 locus in line with a GFP fusion to the native FOXP3 gene. This architecture is intended to allow for ligand-induced selection of cells which have undergone an accurate gene targeting event.
Figure 26:
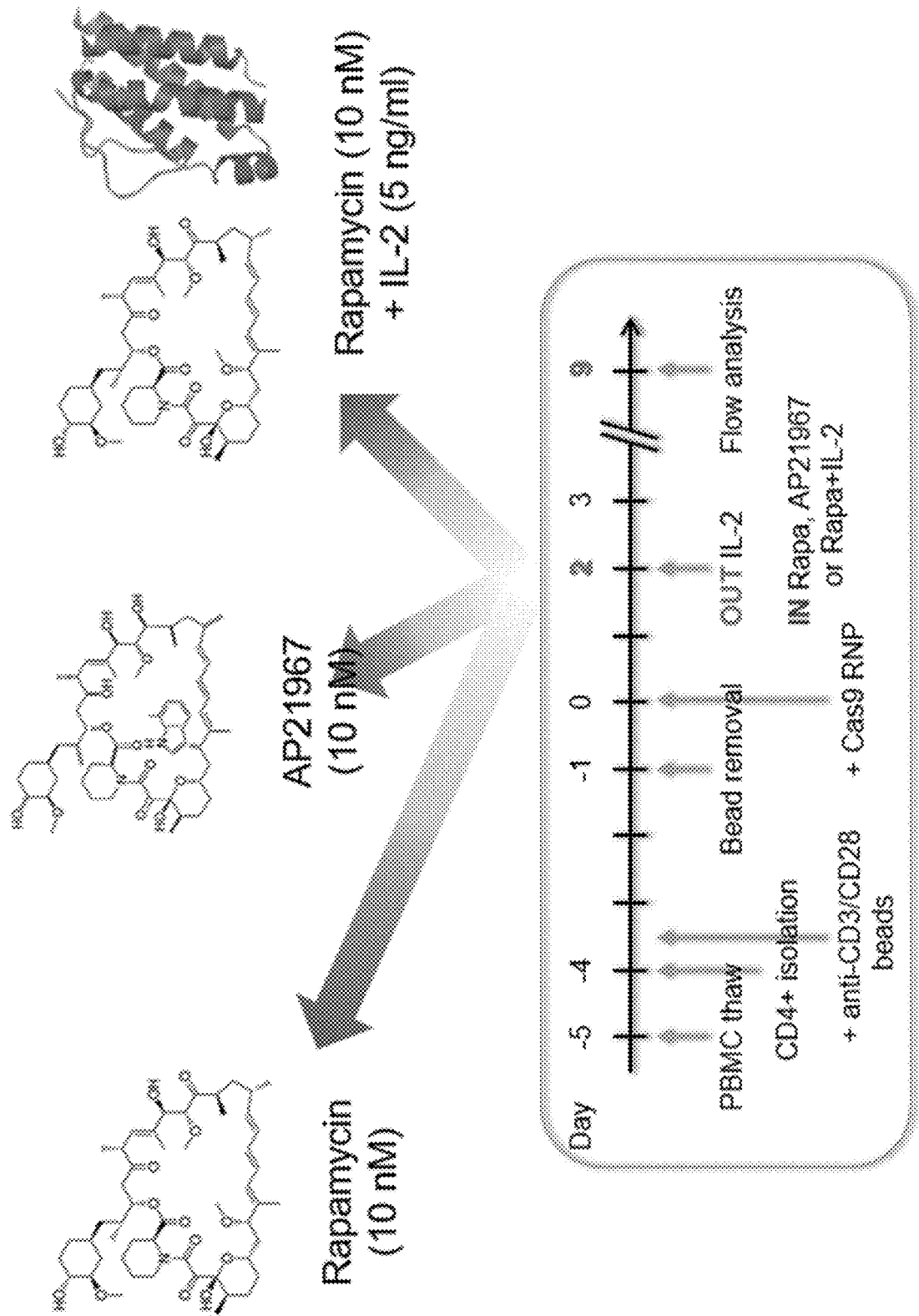
FIG. 26 depicts a schematic diagram showing an experimental design of targeted knock-in of MND promoter and CISC. This represents an experimental schematic of how a CRISP/Cas9 nuclease is used to induce targeted integration of the cassettes from FIG. 25 into the FOXP3 locus, followed by expansion of the gene targeted cells in the indicated IL2R-CISC ligand.
Figure 27:
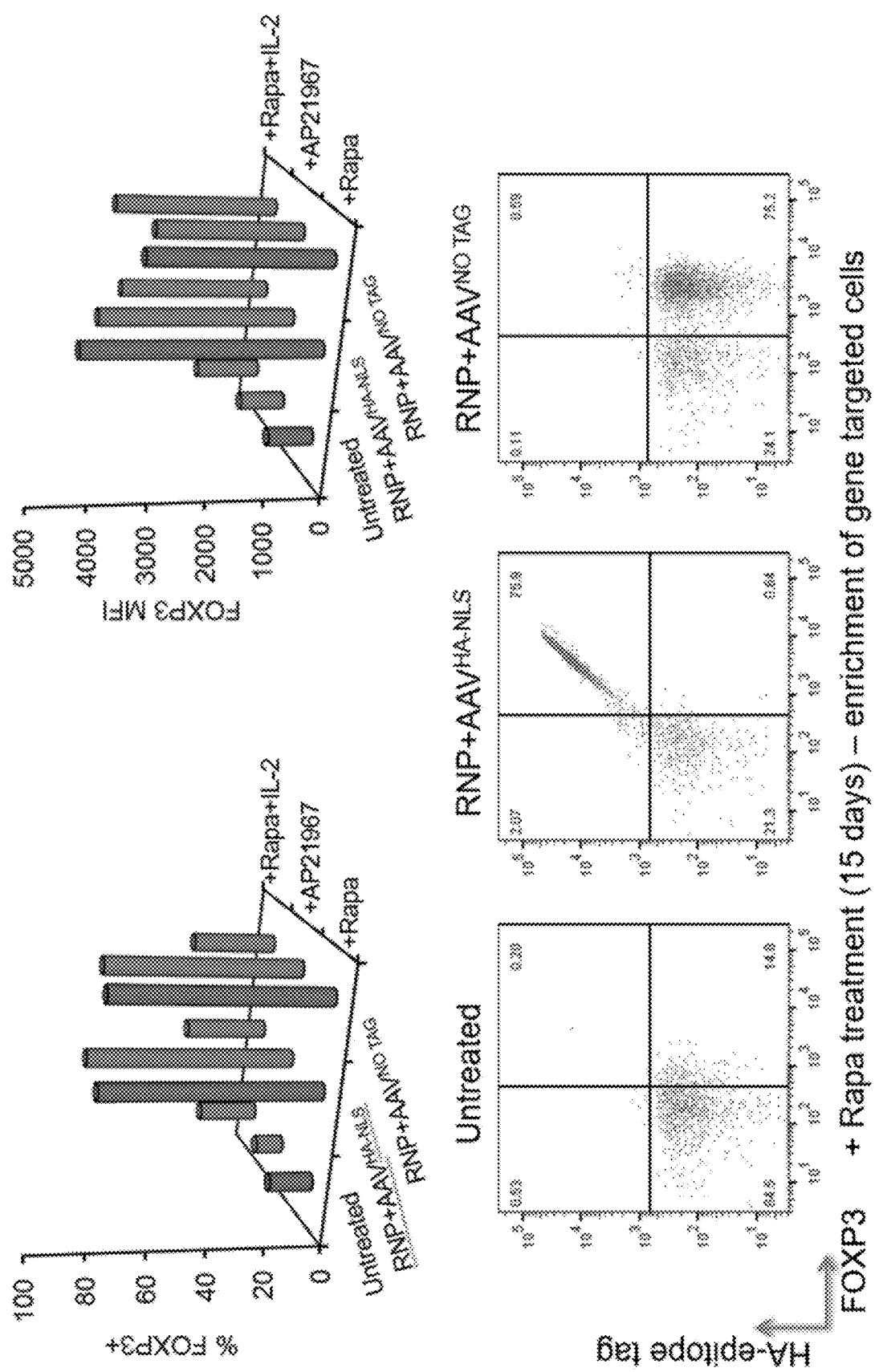
FIG. 27 shows results for targeted knock-in of MND promoter and CISC with rapamycin contact for 15 days, leading to enrichment of gene targeted cells. Following targeted integration into the FOXP3 locus utilizing the indicated approaches (no targeting, or RNP plus each of the cassettes described in FIG. 25), cells were cultured in the indicated conditions for 15 days, and then analyzed by flow cytometry for GFP-FOXP3 expression. Expansion in rapamycin or AP21967 resulted in substantial enrichment of FOXP3 expressing cells, indicating that the IL2R-CISC are able to drive ligand-induced enrichment of gene targeted cell populations, including those in which FOXP3 is overexpressed. Flow panels are representative of IL2R-CISC GFP-FOXP3 expression by cells cultured in rapamycin.
Figure 28:
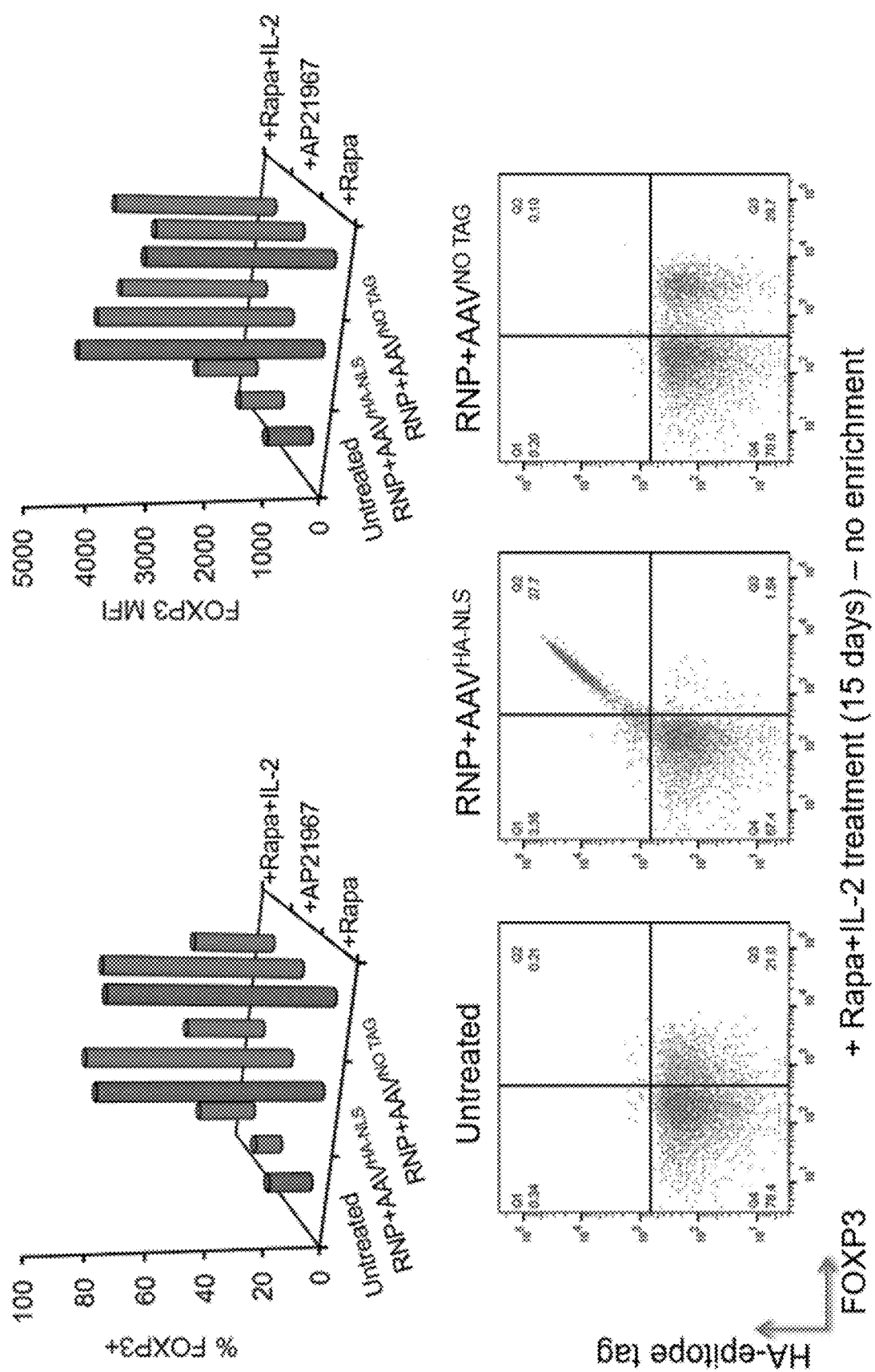
FIG. 28 shows results for targeted knock-in of MND promoter and CISC, with rapamycin+IL-2 contact for 15 days, resulting in no enrichment of gene targeted cells. Following targeted integration into the FOXP3 locus utilizing the indicated approaches, cells were cultured in the indicated conditions for 15 days, and then analyzed by flow cytometry for GFP-FOXP3 expression. Expansion in rapamycin+IL2 resulted in no detectable enrichment or loss of FOXP3 expressing cells vs untreated cells, indicating that the IL2R-CISC does not detrimentally affect the function of FOXP3 overexpressing cells. Flow panels are representative of IL2R-CISC GFP-FOXP3 expression by cells cultured in IL-2+rapamycin.

In addition, the targeted knock-in of MND promoter and CISC was tested to enrich and/or expand gene targeted T cells. FIG. 25 shows the gene constructs for the targeted knock-in of the MND promoter, and FIG. 26 graphically depicts one embodiment of the method protocol used for the targeted knock-in. Briefly, PBMC feeder cells were thawed and CD4+ cells were isolated in the presence of anti-CD3/CD28 beads. The beads were removed and Cas9/gRNA ribonucleoproteins (RNPs) were added. The construct was then treated with various conditions, including: no treatment, 10 nM AP21967, 10 nM rapamycin, or 10 nM rapamycin+5 ng/mL IL-2. As shown in FIGS. 27 and 28, contact with rapamycin resulted in enrichment of gene targeted cells, whereas contact with rapamycin and IL-2 showed no enrichment.

The present disclosure has been described above with reference to specific alternatives. However, other alternatives than the above described are equally possible within the scope of the disclosure. Different method steps than those described above, may be provided within the scope of the disclosure. The different features and steps described herein may be combined in other combinations than those described.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those of skill within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

In addition, where features or aspects of the disclosure are described in terms of Markush groups, those skilled in the art will recognize that the disclosure is also thereby described in terms of any individual member or subgroup of members of the Markush group.

Any of the features of an alternative of the first through eleventh aspects is applicable to all aspects and alternatives identified herein. Moreover, any of the features of an alternative of the first through eleventh aspects is independently combinable, partly or wholly with other alternatives described herein in any way, e.g., one, two, or three or more alternatives may be combinable in whole or in part. Further, any of the features of an alternative of the first through eleventh aspects may be made optional to other aspects or alternatives. Although described above in terms of various example alternatives and implementations, it should be understood that the various features, aspects and functionality described in one or more of the individual alternatives are not limited in their applicability to the particular alternative with which they are described, but instead may be applied, alone or in various combinations, to one or more of the other alternatives of the present application, whether or not such alternatives are described and whether or not such features are presented as being a part of a described alternative. Thus, the breadth and scope of the present application should not be limited by any of the above-described example alternatives.

All references cited herein are incorporated herein by reference in their entirety. To the extent publications and patents or patent applications incorporated by reference contradict the disclosure contained in the specification, the specification is intended to supersede and/or take precedence over any such contradictory material. To the extent publications and patents or patent applications incorporated by reference herein contradict the disclosure contained in the specification, the specification is intended to supersede and/or take precedence over any such contradictory material.

What is claimed is:

1. A method for making a genetically modified cell, comprising contacting a cell with:
   (i) a first nucleic acid encoding a first chemically inducible signaling complex (CISC) component, wherein the first CISC component comprises in an N-to-C terminal order:
      (a) an extracellular domain comprising an FK506-binding protein (FKBP) domain;
      (b) an IL-2 receptor γ (IL-2Rγ) transmembrane domain; and
      (c) an IL-2Rγ cytoplasmic signaling domain; and
   (ii) a second nucleic acid encoding a second CISC component, wherein the second CISC component comprises in an N-to-C-terminal order:
      (a) an extracellular domain comprising an FKBP-rapamycin-binding (FRB) domain;
      (b) an IL-2 receptor β (IL-2Rβ) transmembrane domain; and
      (c) an IL-2Rβ cytoplasmic signaling domain.

2. The method of claim 1, wherein the first CISC component comprises an amino acid sequence having at least 95% sequence identity to any one of:
   (1) amino acids 21-251 of SEQ ID NO: 1;
   (2) amino acids 21-352 of SEQ ID NO: 3;
   (3) amino acids 21-349 of SEQ ID NO: 5; or
   (4) amino acids 21-251 of SEQ ID NO: 7.

3. The method of claim 1, wherein the second CISC component comprises an amino acid sequence having at least 95% sequence identity to any one of:
   (1) amino acids 22-429 of SEQ ID NO: 2;
   (2) amino acids 22-544 of SEQ ID NO: 4;
   (3) amino acids 22-541 of SEQ ID NO: 6; or
   (4) amino acids 22-379 of SEQ ID NO: 8.

4. The method of claim 1, wherein the first CISC component comprises an amino acid sequence of any one of:
   (1) amino acids 21-251 of SEQ ID NO: 1;
   (2) amino acids 21-352 of SEQ ID NO: 3;
   (3) amino acids 21-349 of SEQ ID NO: 5; or
   (4) amino acids 21-251 of SEQ ID NO: 7.

5. The method of claim 1, wherein the second CISC component comprises an amino acid sequence of any one of:
   (1) amino acids 22-429 of SEQ ID NO: 2;
   (2) amino acids 22-544 of SEQ ID NO: 4;
   (3) amino acids 22-541 of SEQ ID NO: 6; or
   (4) amino acids 22-379 of SEQ ID NO: 8.

6. The method of claim 1, wherein the first CISC component comprises an amino acid sequence having at least 95% sequence identity to amino acids 21-251 of SEQ ID NO: 1.

7. The method of claim 1, wherein the second CISC component comprises an amino acid sequence having at least 95% sequence identity to amino acids 22-429 of SEQ ID NO: 2.

8. The method of claim 1, wherein the first CISC component comprises amino acids 21-251 of SEQ ID NO: 1.

9. The method of claim 1, wherein the first CISC component comprises amino acids 22-429 of SEQ ID NO: 2.

10. The method of claim 1, wherein the first CISC component comprises an amino acid sequence having at least 95% sequence identity to amino acids 21-251 of SEQ ID NO: 1, and the second CISC component comprises an amino acid sequence having at least 95% sequence identity to amino acids 22-429 of SEQ ID NO: 2.

11. The method of claim 1, wherein the cell is a T cell.

12. The method of claim 1, wherein the first nucleic acid and the second nucleic acid are comprised in one or more viral vectors.

13. The method of claim 12, wherein the one or more viral vectors are adenovirus-associated viral (AAV) vectors.

14. The method of claim 12, wherein the one or more viral vectors are lentiviral vectors.

15. The method of claim 12, wherein the first nucleic acid and the second nucleic acid are comprised in separate viral vectors.

16. The method of claim 1, further comprising contacting the cell with a ligand, thereby causing the first and second CISC components to dimerize.

17. The method of claim 16, wherein the cell is selectively expanded from a heterogenous population of cells.

18. The method of claim 16, wherein the ligand is rapamycin.

19. The method of claim 16, wherein the ligand is a rapalog selected from the group consisting of everolimus, CCI-779, C20-methallylrapamycin, C16-(S)-3-methylindol-erapamycin, C16-iRap, AP21967, sodium mycophenolic acid, benidipine hydrochloride, AP1903, AP23573, and metabolites, derivatives, and/or combinations thereof.

20. The method of claim 16, wherein the ligand is present in an amount from 0.05 nM to 10 nM.

* * * * *

UNITED STATES PATENT AND TRADEMARK OFFICE
CERTIFICATE OF CORRECTION

| | | |
|---|---|---|
| PATENT NO. | : 12,358,970 B2 | Page 1 of 3 |
| APPLICATION NO. | : 18/446018 | |
| DATED | : July 15, 2025 | |
| INVENTOR(S) | : Andrew M. Scharenberg | |

It is certified that error appears in the above-identified patent and that said Letters Patent is hereby corrected as shown below:

On the Title Page

On Page 3, Column 2, Line 33, item (56) under Other Publications, delete "2015, OncBac 2.0:" and insert --2015, OneBac 2.0:--.

On Page 3, Column 2, Line 45, item (56) under Other Publications, delete "methyl-oligoribonucelotides into" and insert --methyl-oligoribonucleotides into--.

On Page 3, Column 2, Line 68, item (56) under Other Publications, delete "2014, CRPSPR-Cas" and insert --2014, CRISPR-Cas--.

On Page 4, Column 1, Line 28, item (56) under Other Publications, delete "novel classs of" and insert --novel class of--.

On Page 4, Column 2, Line 4, item (56) under Other Publications, delete "FKBP12-reapamycin-binding" and insert --FKBP12-rapamycin-binding--.

On Page 4, Column 2, Line 5, item (56) under Other Publications, delete "for FSBP12-rapamycin" and insert --for FKBP12-rapamycin--.

In the Specification

In Column 3, Line 38, delete "nM, 0.5, nM," and insert --nM, 0.5 nM,--.

In Column 6, Line 21, delete "nM, 0.5, nM," and insert --nM, 0.5 nM,--.

In Column 13, Line 32, delete "FRB-CD250 (transmembrane" and insert --FRB-CD25β (transmembrane--.

In Column 16, Line 18, delete "anti-TL2 neutralizing" and insert --anti-IL2 neutralizing--.

Signed and Sealed this
Ninth Day of September, 2025

Coke Morgan Stewart
*Acting Director of the United States Patent and Trademark Office*

CERTIFICATE OF CORRECTION (continued)　　　　　　　　　　　　　　　　　　Page 2 of 3
U.S. Pat. No. 12,358,970 B2

In Column 16, Line 30, delete "anti-TL2 antibody." and insert --anti-IL2 antibody.--.

In Column 16, Line 30, delete "anti-TL2 antibody" and insert --anti-IL2 antibody--.

In Column 16, Line 40, delete "reflecting TL2R turnover" and insert --reflecting IL2R turnover--.

In Column 17, Line 53, delete "of 20% or" and insert --of ±20% or--.

In Column 17, Line 54, delete "preferably +5%, even" and insert --preferably ±5%, even--.

In Column 17, Line 54, delete "preferably +1%, and" and insert --preferably ±1%, and--.

In Column 17, Line 55, delete "preferably +0.1% from" and insert --preferably ±0.1% from--.

In Column 18, Line 29, delete "phosphorodiselenoate, phosphoroanilothioate, phosphoranilidate," and insert --phosphorodiselenoate, phosphoroamidothioate, phosphoranilidate,--.

In Column 19, Line 54, delete "constitutive promoter" and insert --constitutive promoter.--.

In Column 23, Line 44, delete "gamma (IL2Ry or" and insert --gamma (IL2Rγ or--.

In Column 23, Line 46, delete "beta (IL2RP or" and insert --beta (IL2Rβ or--.

In Column 23, Line 56, delete "or "IL2R β" refers" and insert --or "IL2Rβ" refers--.

In Column 23, Line 58, delete "or IL2Rγ" refers" and insert --or "IL2Rγ" refers--.

In Column 24, Line 13-14, delete "a heterodimizeration pair," and insert --a heterodimerization pair,--.

In Column 25, Line 28, delete "O-(oxetan-3" and insert --O-(oxetane-3--.

In Column 25, Line 64, delete "18,19, 24,25," and insert --18,19,24,25,--.

In Column 26, Line 7, delete "19E,215,23S," and insert --19E,21S,23S,--.

In Column 26, Line 60, delete "via ent-kauren, including" and insert --via ent-kaurene, including--.

In Column 26, Lines 60-61, delete "including gibberelling 1" and insert --including gibberellin 1--.

In Column 28, Line 41, delete "cells (TM cells)" and insert --cells ($T_M$ cells)--.

In Column 28, Line 55, delete "(or "TEM") as" and insert --(or "$T_{EM}$") as--.

In Column 30, Line 50, delete "T-cells" or" and insert --"T-cells" or--.

CERTIFICATE OF CORRECTION (continued)
U.S. Pat. No. 12,358,970 B2

In Column 33, Line 27, delete "LWWH" and insert --LWH--.

In Column 35, Line 14, delete "an IL2Ra complex." and insert --an IL2Rα complex.--.

In Column 35, Line 20, delete "HLLLV" and insert --HLLV--.

In Column 55, Line 30, delete "effector TE are" and insert --effector $T_E$ are--.

In Column 59, Line 1, delete "PI3K, INK, ERK," and insert --PI3K, JNK, ERK,--.

In Column 61, Line 11, delete "that 1L2R-CISC" and insert --that IL2R-CISC--.

In the Claims

In Column 81, Claim 1, Line 59, delete "an IL-2Rγ cytoplasmic" and insert --an IL-2Rγ cytoplasmic--.